(12) United States Patent
Chakravarty et al.

(10) Patent No.: US 12,077,450 B2
(45) Date of Patent: Sep. 3, 2024

(54) TANTALUM OXIDE NANOPARTICLE CONTRAST AGENTS

(71) Applicant: Board of Trustees of Michigan State University, East Lansing, MI (US)

(72) Inventors: Shatadru Chakravarty, Rolla, MO (US); Erik M. Shapiro, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 450 days.

(21) Appl. No.: 17/367,919

(22) Filed: Jul. 6, 2021

(65) Prior Publication Data
US 2022/0048788 A1    Feb. 17, 2022

Related U.S. Application Data

(60) Provisional application No. 63/066,029, filed on Aug. 14, 2020.

(51) Int. Cl.
| | |
|---|---|
| *C01G 35/00* | (2006.01) |
| *A61K 47/69* | (2017.01) |
| *A61K 49/04* | (2006.01) |
| *B82Y 30/00* | (2011.01) |
| *B82Y 40/00* | (2011.01) |
| *G01N 23/046* | (2018.01) |

(52) U.S. Cl.
CPC .......... *C01G 35/00* (2013.01); *A61K 47/6923* (2017.08); *A61K 47/6929* (2017.08); *A61K 49/0428* (2013.01); *B82Y 30/00* (2013.01); *B82Y 40/00* (2013.01); *C01P 2004/64* (2013.01); *C01P 2004/84* (2013.01); *G01N 23/046* (2013.01)

(58) Field of Classification Search
None
See application file for complete search history.

(56) References Cited

U.S. PATENT DOCUMENTS

| | | | |
|---|---|---|---|
| 8,871,310 B2 | 10/2014 | Hyeon et al. | |
| 2013/0065995 A1* | 3/2013 | Hyeon | B82Y 5/00 424/9.42 |

OTHER PUBLICATIONS

Munaz, Ahmed, et al. "Three-dimensional printing of biological matters." Journal of Science: Advanced Materials and Devices 1.1 (2016): 1-17.

(Continued)

*Primary Examiner* — Jeffrey D Washville
(74) *Attorney, Agent, or Firm* — Harness, Dickey & Pierce, PLC

(57) ABSTRACT

A nanoparticle composition is provided. The nanoparticle composition includes a plurality of nanoparticles, each nanoparticle of the plurality having a core including tantalum oxide, and a covalent coating covalently bound to the core. The covalent coating includes a surface modifier selected from the group consisting of (3-aminopropyl)trimethoxy silane (APTMS), (3-aminopropyl)triethoxy silane (APTES), APTMS-methoxy-poly(ethylene-glycol)-succinimidyl glutarate (APTMS-m-PEG-glutarate), APTES-methoxy-poly (ethylene-glycol)-succinimidyl glutarate (APTES-m-PEG-glutarate), 2-[methoxy (polyethyleneoxy)-9-12-propyl] trimethoxysilane (PEG-Silane), hexadecyltriethoxy silane, and combinations thereof. Methods of synthesizing and using the nanoparticle composition are also provided.

24 Claims, 76 Drawing Sheets

(56) References Cited

OTHER PUBLICATIONS

Gao, Fei, et al. "Monodispersed mesoporous silica nanoparticles with very large pores for enhanced adsorption and release of DNA." The journal of physical chemistry B 113.6 (2009): 1796-1804.

* cited by examiner

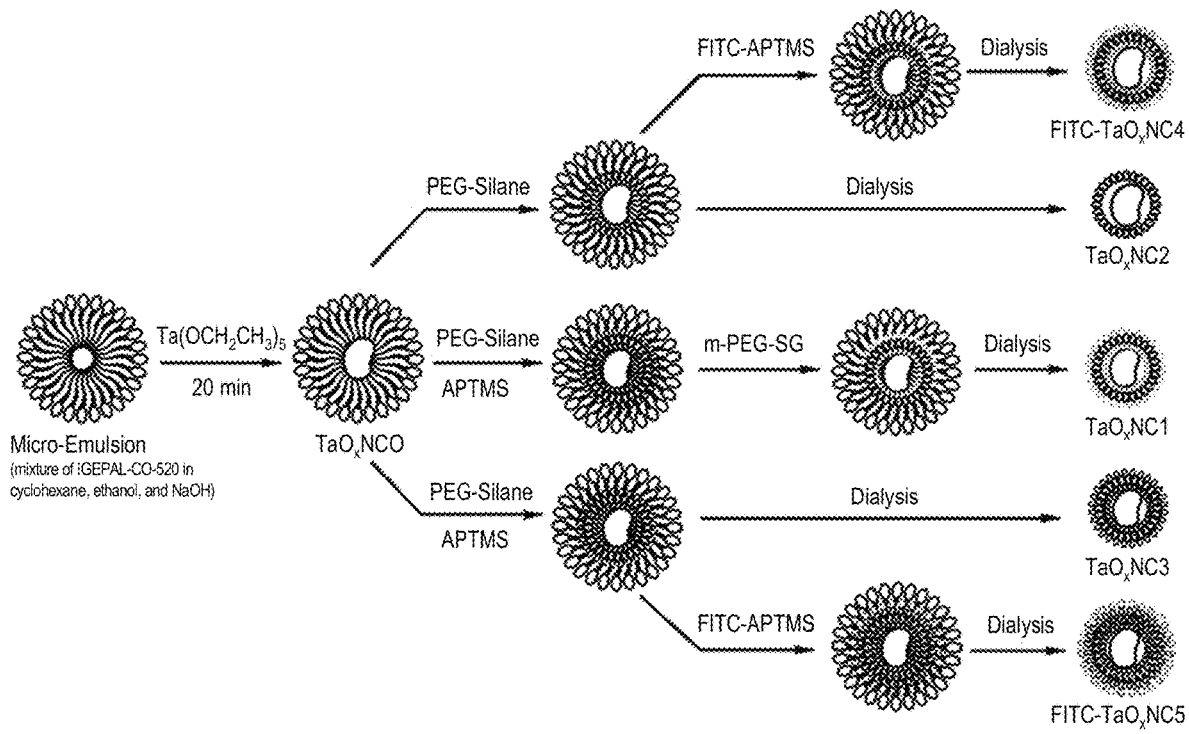
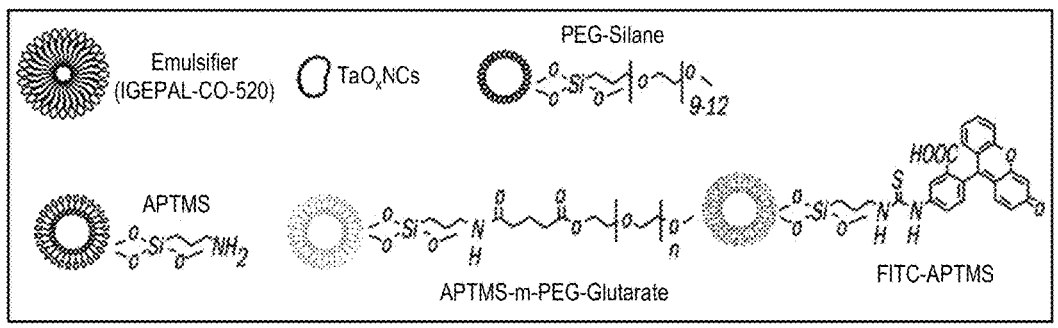
Fig. 4A

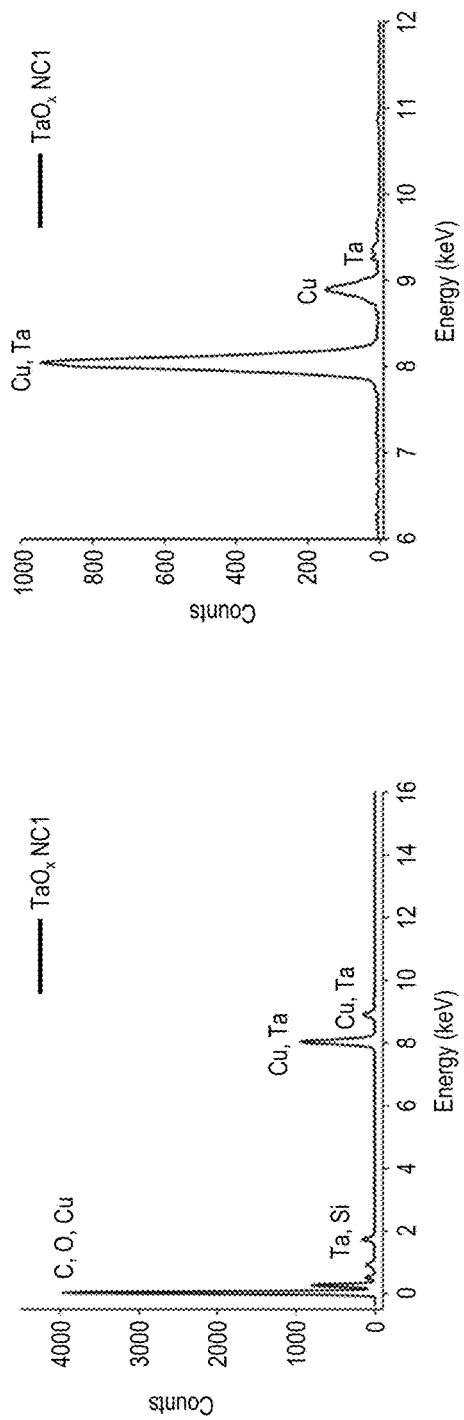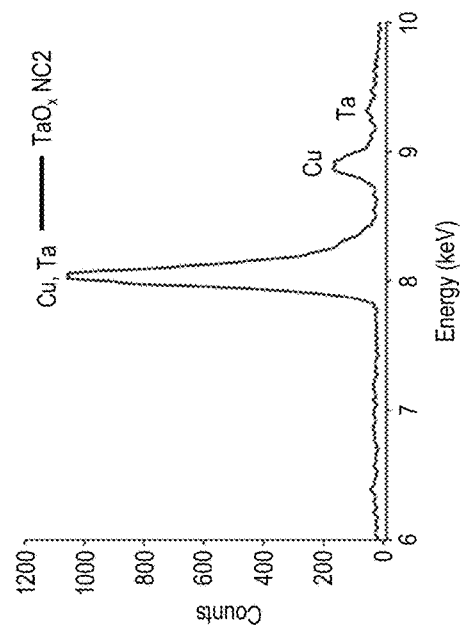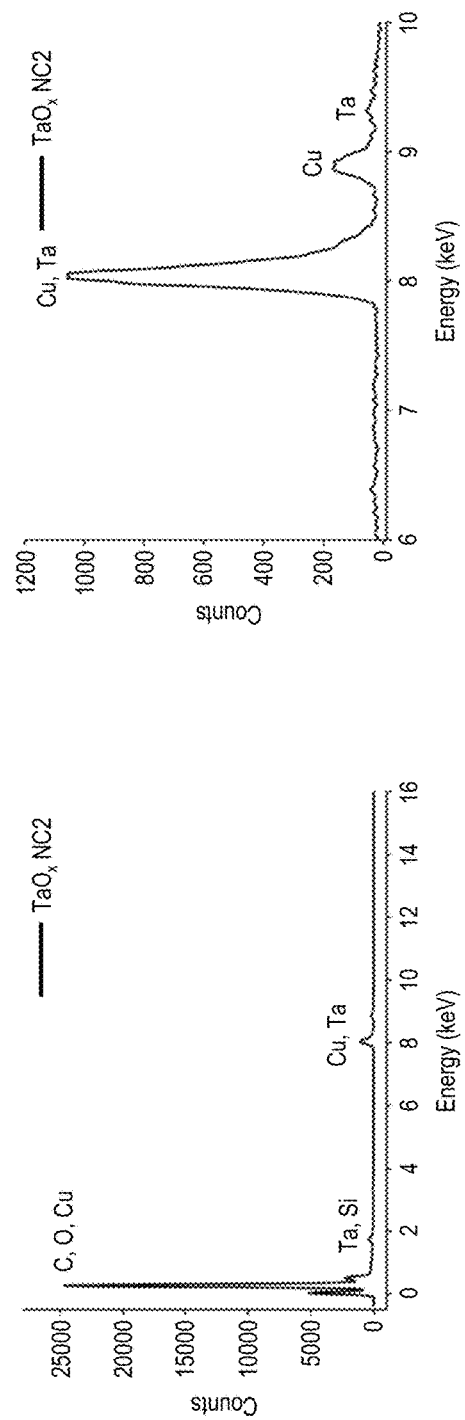

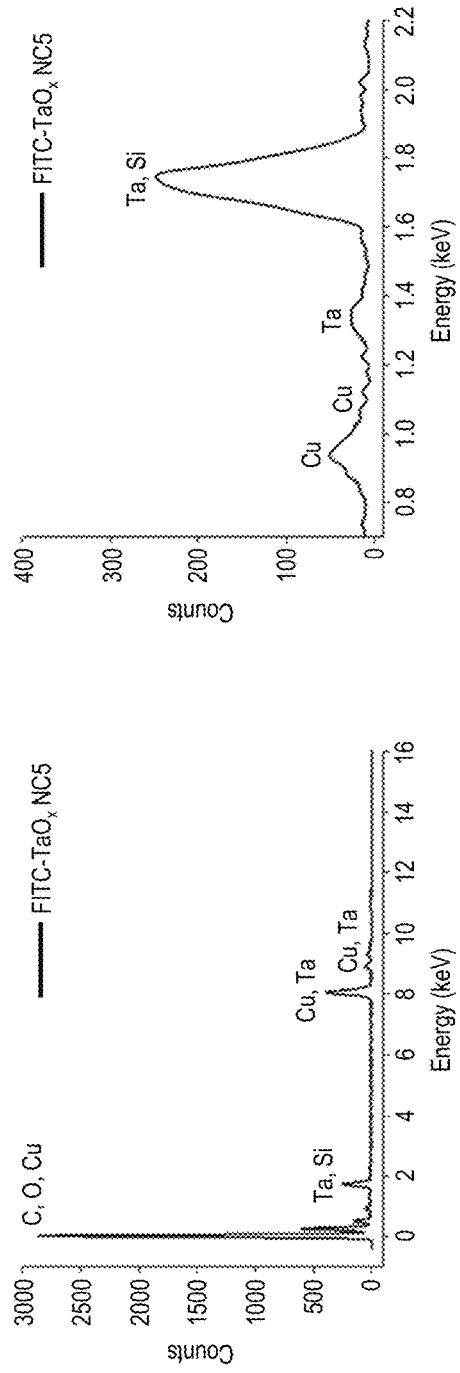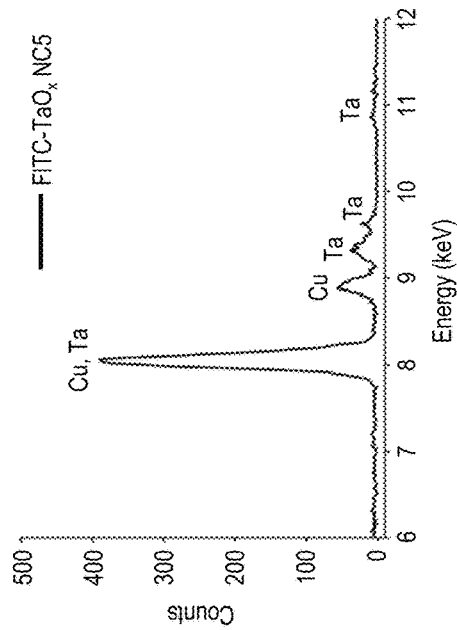

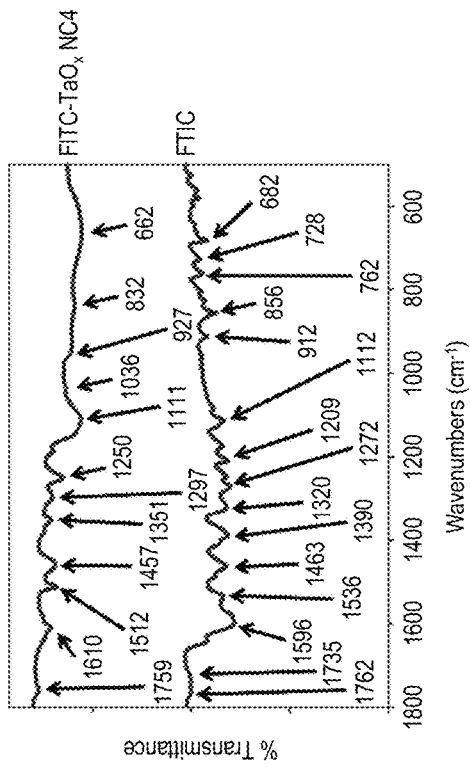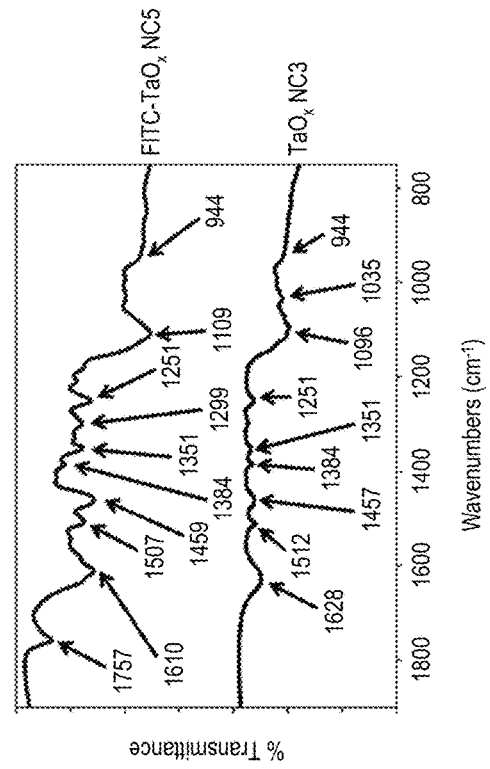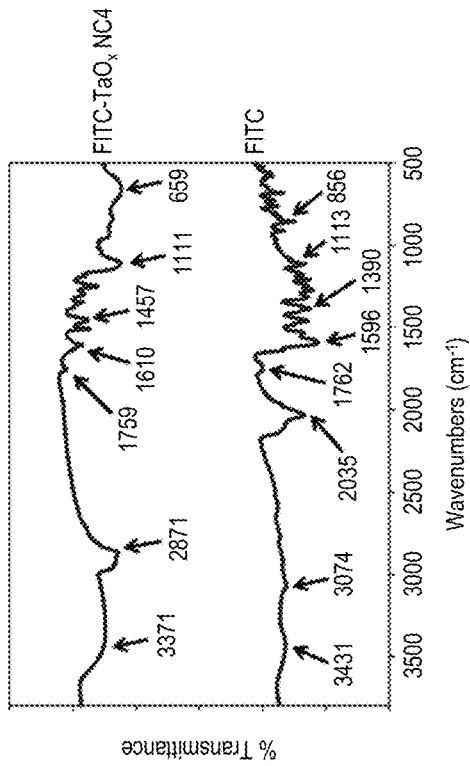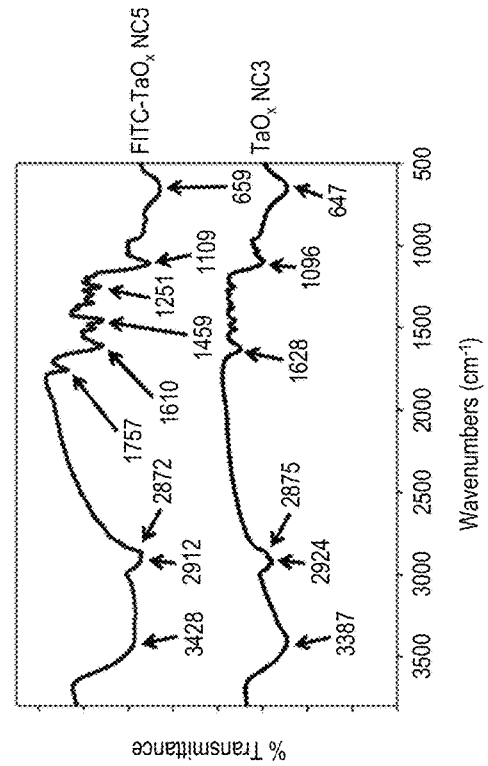

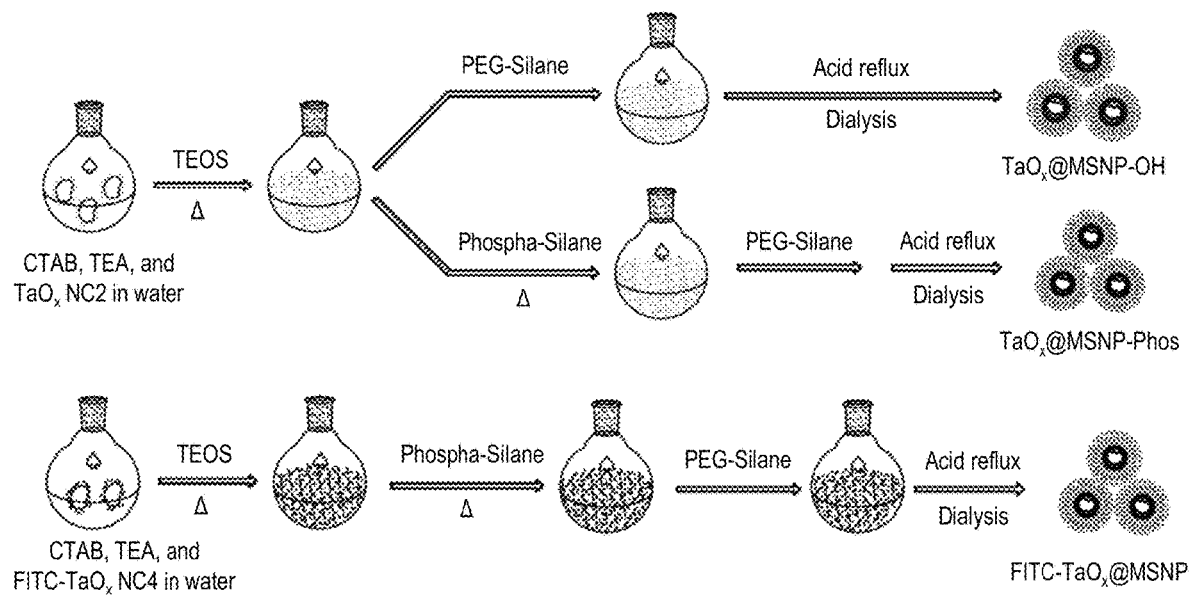
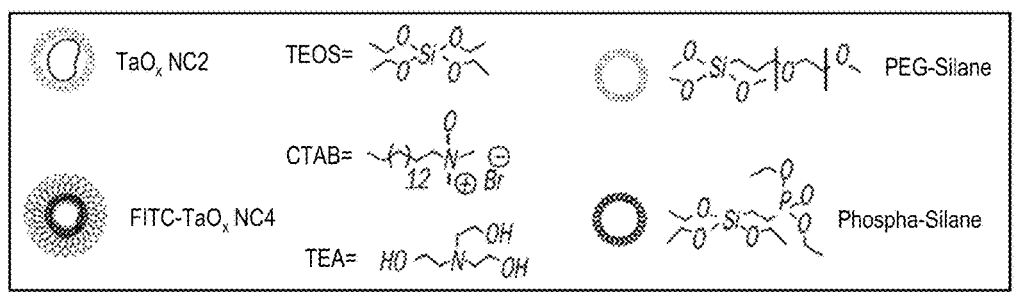
Fig. 54

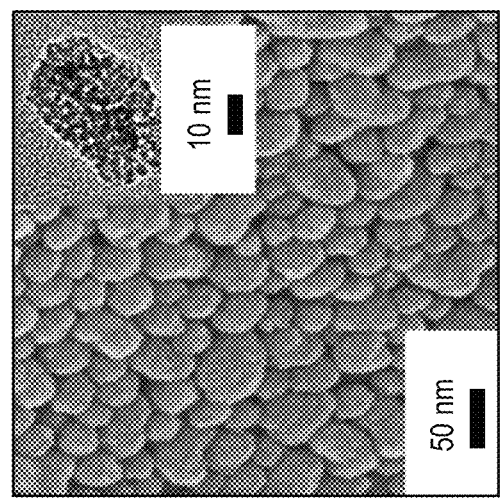
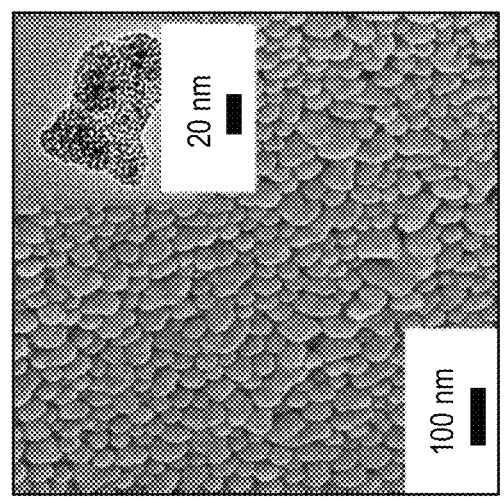
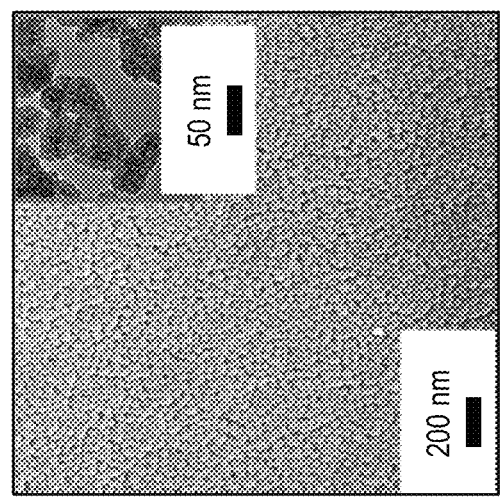
Fig. 63C
Fig. 63B
Fig. 63A

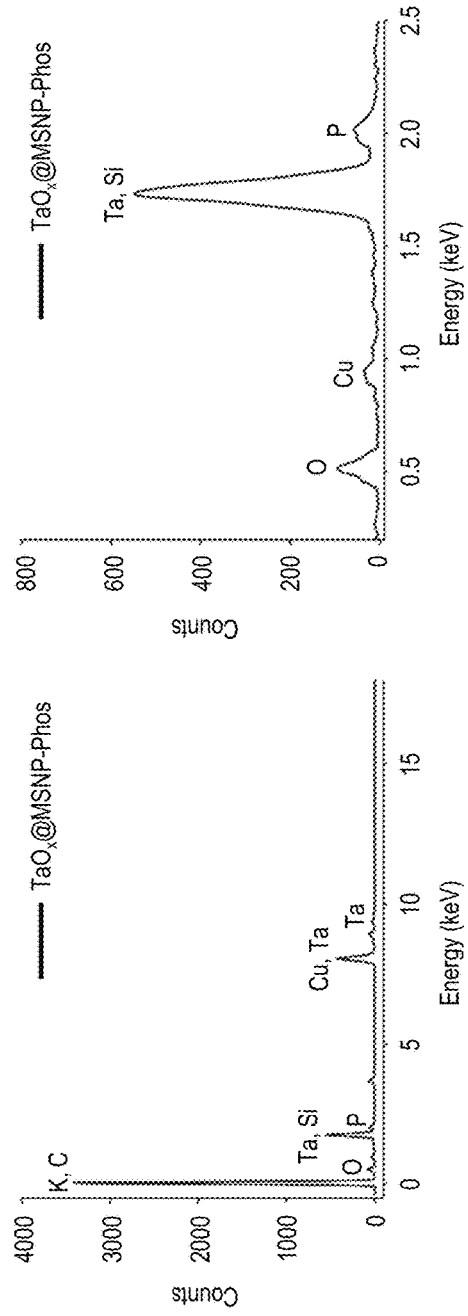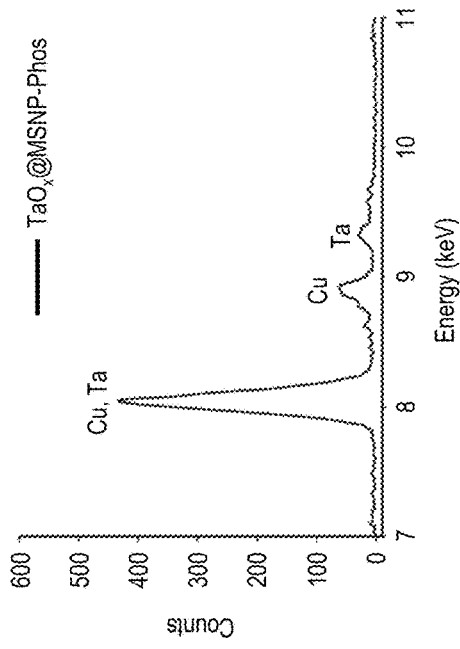
Fig. 66A
Fig. 66B
Fig. 66C

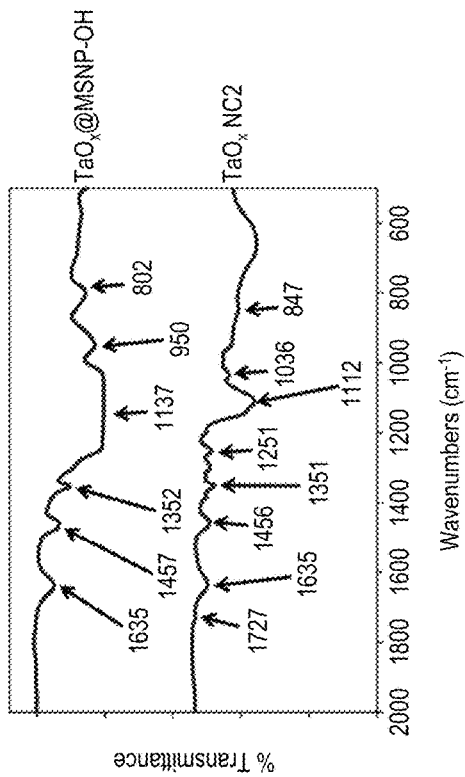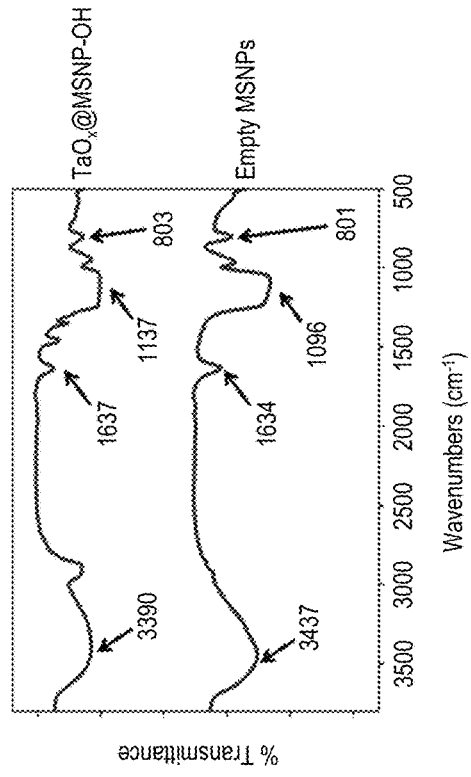
Fig. 70A
Fig. 70B
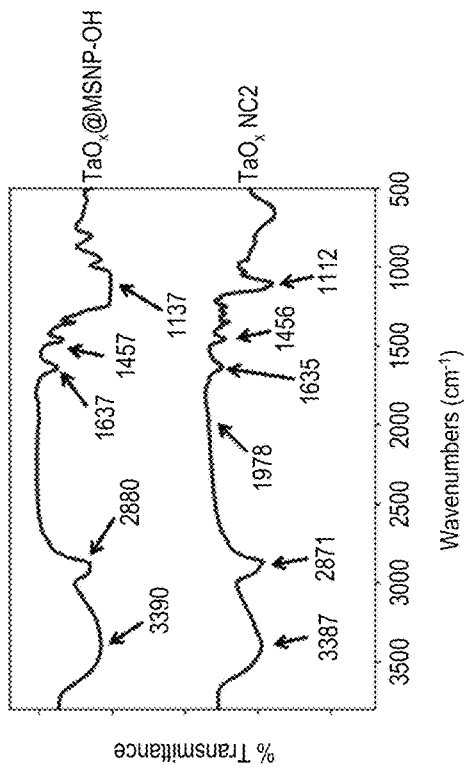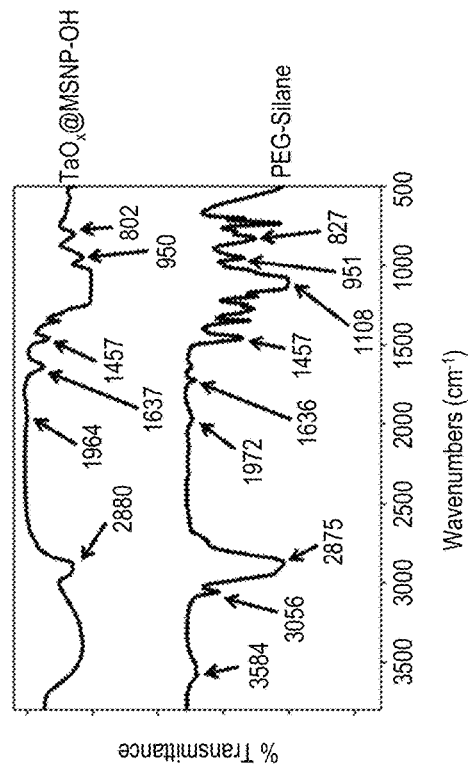
Fig. 70C
Fig. 70D

TANTALUM OXIDE NANOPARTICLE CONTRAST AGENTS

CROSS-REFERENCE TO RELATED APPLICATION

This application claims the benefit of U.S. provisional patent application Ser. No. 63/066,029, filed on Aug. 14, 2020, which is incorporated by reference herein.

GOVERNMENT RIGHTS

This invention was made with government support under CA185163, EB017881, and CA226579 awarded by the National Institutes of Health. The government has certain rights in the invention.

FIELD

The present disclosure relates to tantalum oxide nanoparticles and their use as contrast agents for X-ray computed tomography.

BACKGROUND

This section provides background information related to the present disclosure which is not necessarily prior art.

X-ray computed tomography, or CT, has matured into an important molecular imaging tool, propelled forward by innovations in contrast agents (CAs), imaging systems, image acquisition schemes, and image analysis strategies. CT CAs enable molecular imaging by attenuating X-rays at their location, giving rise to signal in CT images. Iodine (Z=53) is the most used element clinically and is the imageable component in a number of FDA-approved CT CAs. CT CAs containing barium (Z=56) are also used clinically. These chemical elements have uniquely varying X-ray attenuation as a function of X-ray energy, which can be exploited for multiple molecular imaging approaches, including dual energy CT material decomposition and spectral photon counting CT.

CT molecular imaging requires the preparation of new CAs incorporating these elements, and numerous reports have detailed experimental CT CAs incorporating silver (Ag, Z=47), gadolinium (Gd, Z=64), ytterbium (Yb, Z=70), tantalum (Ta, Z=73), platinum (Pt, Z=78), gold (Au, Z=79), and bismuth (Bi, Z=83), among others. Due to the inherent low sensitivity of CT for these contrast media, requiring 10's millimolar for detection, these new contrast media are most often nanoparticles (NPs), enabling the efficient packaging of X-ray attenuating elements within a compact volume.

With its K edge at 67 keV, Ta has high attenuation of X-rays used in clinical CT systems today (80-140 kVp) and produces more CT contrast w/w than Au or 1. Synthetic schemes for Ta nanocrystals (NCs), $Ta_2O_5$ and $TaO_x$, are well described and repeatable, and analytical methodologies are straightforward. Further, multiple reports have established that Ta-based nanomaterials exhibit low toxicity in biomedical milieu. Lastly, Ta is a relatively inexpensive material, which is an important consideration long term for commercialization.

Generally, surface-protected Ta NPs have been formulated as very small NPs for use as injectable CAs. As an example, zwitterionic, sub-10 nm $Ta_2O_5$ NPs have been prepared by the hydrolysis and condensation of a mixture of silane surface ligands on isobutyric acid stabilized $Ta_2O_5$ cores. These have been demonstrated as a safe and effective CT CA, with increased effectiveness versus I in clinical CT scenarios, especially in large adults. In a separate study, 5-10 nm $Ta_2O_5$ NPs have also been used for imaging cartilage via interactions with the charged cartilage matrix. The overall Ta content in all these reported NPs is about 30-41%.

Given the importance of CT CA molar concentration for detection, $TaO_x$ may be a better choice than $Ta_2O_5$ NPs. The mass percent of Ta in $Ta_2O_5$ is 82%, while in $TaO_x$, it is between 92% (x=1) and 85% (x=2). Further, the density of $Ta_2O_5$ is 8.2-8.4 g $cm^{-3}$, while it is 10.5 g $cm^{-3}$ for $TaO_x$. The product of the increased mass percent and the higher density results in $TaO_x$ having 32-43% higher Ta than $Ta_2O_5$ for a given volume depending on the value for 'x' in $TaO_x$. The synthesis of $TaO_x$ NCs involves a base-catalyzed sol-gel reaction with a tantalum (V) ethoxide precursor. The $TaO_x$ NP surface has a high propensity for reacting with silanes, and this was used for consequent surface modification to generate hydrophilic well-dispersed NPs. This fundamental, easy to replicate procedure has been adopted by multiple groups to design and fabricate $TaO_x$ NPs for drug delivery, imaging, and radiotherapy. However, none of these reports indicate the Ta concentration within the NP construct. A high Ta concentration is a prerequisite to generate a robust contrast agent for CT and is essential to augment the development of CT as a molecular imaging tool.

Conventional $TaO_x$ NPs have a low Ta concentration and a limited solubility. These issues negatively affect the effectiveness of the $TaO_x$ NPs for clinical purposes. Accordingly, $TaO_x$ NPs that have a high Ta concentration and are highly soluble are desired.

SUMMARY

This section provides a general summary of the disclosure, and is not a comprehensive disclosure of its full scope or all of its features.

The present disclosure relates to tantalum oxide nanoparticle contrast agents. In various aspects, the current technology provides a nanoparticle composition including a plurality of nanoparticles, each nanoparticle of the plurality having a core including tantalum oxide, and a covalent coating covalently bound to the core, the covalent coating including a surface modifier selected from the group consisting of (3-aminopropyl)trimethoxy silane (APTMS), (3-aminopropyl)triethoxy silane (APTES), APTMS-methoxy-poly(ethylene-glycol)-succinimidyl glutarate (APTMS-m-PEG-glutarate), APTES-methoxy-poly(ethylene-glycol)-succinimidyl glutarate (APTES-m-PEG-glutarate), 2-[methoxy (polyethyleneoxy)-9-12-propyl] trimethoxysilane (PEG-Silane), fluorescein isothiocyanate (FITC)-APTMS, FITC-APTES, hexadecyltriethoxy silane, and combinations thereof.

In one aspect, the nanoparticle composition is in the form of a lyophilized powder. In one aspect, the tantalum oxide includes $TaO_x$, where $0<x\leq2.5$, $Ta_2O_5$, or combinations thereof. In one aspect, the tantalum oxide includes TaO, $TaO_2$, $Ta_2O_5$, or combinations thereof.

In one aspect, the surface modifier includes the PEG-Silane, the APTMS, and the APTMS-m-PEG-glutarate and the plurality of nanoparticles are hydrophilic. In one aspect, the surface modifier includes the PEG-Silane and the plurality of nanoparticles are hydrophilic. In one aspect, the surface modifier includes the PEG-Silane, and the APTMS and the plurality of nanoparticles are hydrophobic. In one aspect, the surface modifier includes the PEG-Silane and the FITC-APTMS and the plurality of nanoparticles are hydrophilic. In one aspect, the surface modifier includes the PEG-Silane, the APTMS, and the FITC-APTMS and the plurality of nanoparticles are hydrophobic.

In one aspect, the surface modifier includes the PEG-Silane and the hexadecyltriethoxy silane. In one aspect, the nanoparticle composition further includes a non-covalent coating non-covalently associated with the hexadecyltriethoxy silane, the non-covalent coating including a hydrophobic polymer. In one aspect, the plurality of nanoparticles are non-covalently embedded within the hydrophobic polymer.

In one aspect, each nanoparticle of the plurality includes at least one core including tantalum oxide, the covalent coating, and a mesoporous silica nanoparticle (MSNP), wherein the at least one core having the covalent coating is embedded within the MSNP. In one aspect, the nanoparticle composition further includes a pharmaceutically acceptable carrier, wherein the nanoparticle composition is configured to provide contrast for computed tomography (CT). In one aspect, the plurality of nanoparticles are embedded within a polymer having a predetermined shape, wherein the nanoparticle composition is configured as a biological scaffold.

In one aspect, the nanoparticle composition further includes a polymer, wherein the plurality of nanoparticles are either dissolved in the polymer or suspended in the polymer, and wherein the nanoparticle composition is configured to solidify into a three-dimensional shape during a three-dimensional printing process. In one aspect, the nanoparticle composition further includes a therapeutic agent coupled to the covalent coating. In various aspects, the current technology also provides a method of fabricating a biological scaffold, the method includes three-dimensional printing the biological scaffold with a bio-ink including the nanoparticle composition.

In various aspects, the current technology further provides a method of fabricating a biological scaffold, the method including disposing a polymer about a mask having a predetermined shape and solidifying the polymer, wherein the polymer includes the nanoparticle. In various aspects, the current technology yet further provides a nanoparticle composition including a plurality of nanoparticles, each nanoparticle of the plurality including a core including tantalum oxide, and a coating including hexadecyltriethoxy silane covalently bound to the core, and a polymer, wherein the plurality of nanoparticles are non-covalently embedded within the polymer. In one aspect, the polymer includes poly(lactic-co-glycolic acid) (PLGA).

In various aspects, the current technology yet further provides a method of synthesizing a nanoparticle composition, the method including combining an organic solvent with an aqueous solution to form a water-in-oil micro-emulsion; adding a compound including tantalum to the micro-emulsion to form uncoated tantalum nanoparticles; and covalently binding a surface modifier to the uncoated tantalum nanoparticles, the surface modifier being selected from the group consisting of an emulsifier, (3-aminopropyl) triethoxy silane (APTMS), APTMS-methoxy-poly(ethylene-glycol)-succinimidyl glutarate (APTMS-m-PEG-glutarate), 2-[methoxy (polyethyleneoxy)-9-12-propyl] trimethoxysilane (PEG-Silane), fluorescein isothiocyanate-APTMS (FITC-APTMS), hexadecyltriethoxy silane, and combinations thereof to form the nanoparticle composition, wherein the nanoparticle composition includes a plurality of nanoparticles, each nanoparticle of the plurality having a core including tantalum oxide, and a covalent coating, the covalent coating including the surface modifier covalently bound to the core. In one aspect, the method further includes embedding the plurality of nanoparticles within a polymer.

In one aspect, the method further includes dialyzing the plurality of nanoparticles in water and lyophilizing the plurality of nanoparticles to generate a lyophilized powder including the plurality of nanoparticles.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 4A-4F are a schematic representations of the syntheses of $TaO_x$ NC formulations in accordance with various aspects of the current technology. An overall scheme is shown in FIG. 4A, and FIGS. 4B-4F show scheme for $TaO_x$ NC1, $TaO_x$ NC2, $TaO_x$ NC3, FITC-$TaO_x$ NC4, and FITC-$TaO_x$ NC5, respectively.

Figure 6C:
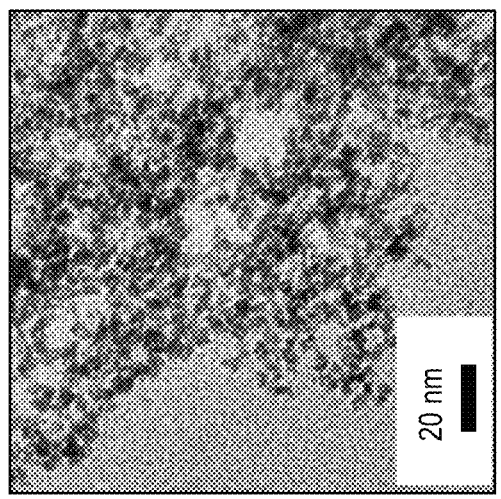
Figure 6B:
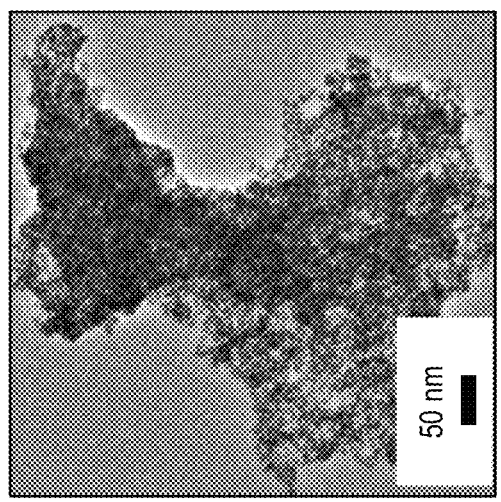
Figure 6A:
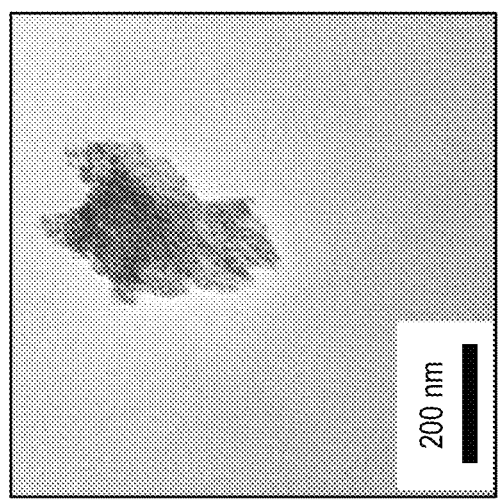

FIGS. 6A-6C are TEM images of bare $TaO_x$ NCs synthesized using APTMS as a singular surface coating agent in accordance with various aspects of the current technology. No PEG-Silane was used. The agglomeration of the resulting NCs signifies the exclusivity of a PEG-based agent required to form a well dispersed collection of $TaO_x$ NCs.

Figure 7A:
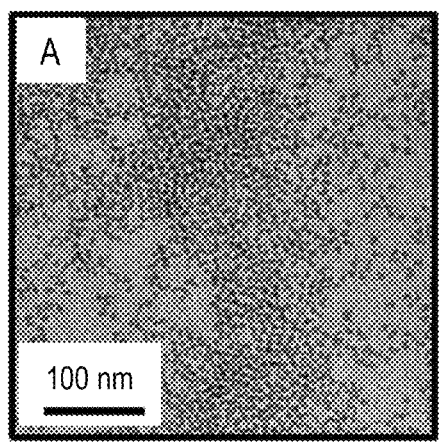
Figure 7B:
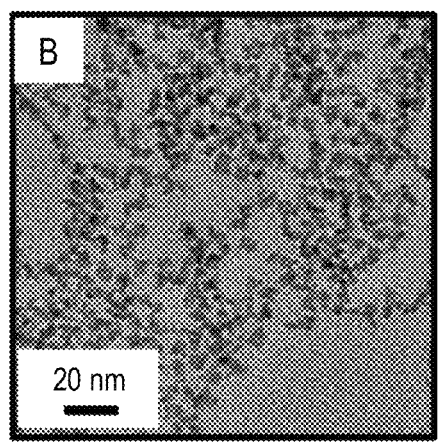
Figure 7C:
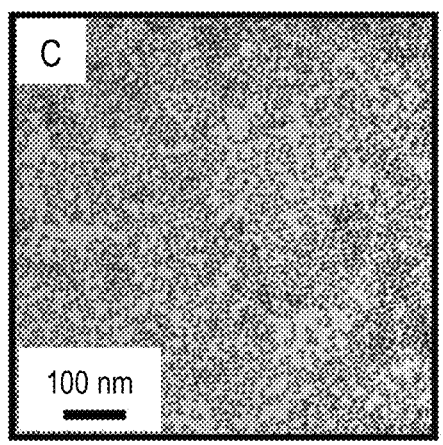
Figure 7D:
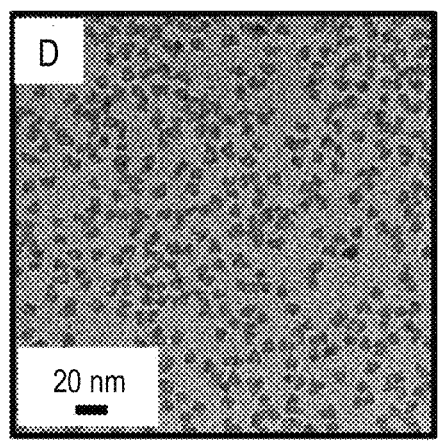
Figure 7E:
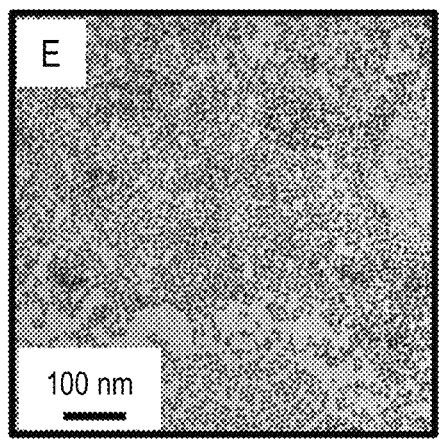
Figure 7F:
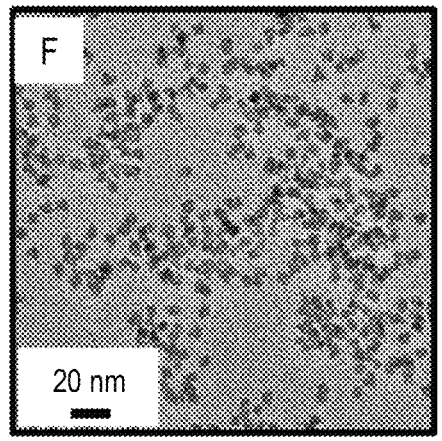
Figure 7G:
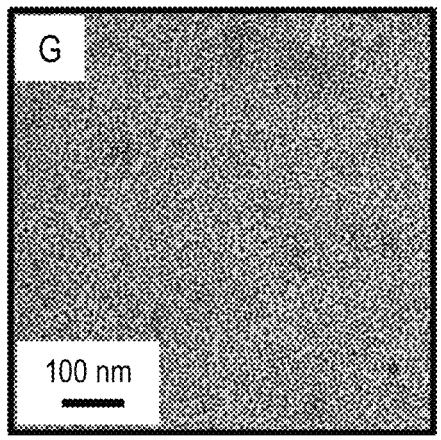
Figure 7H:
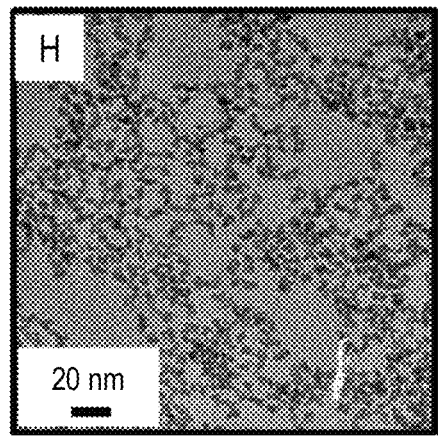
Figure 7I:
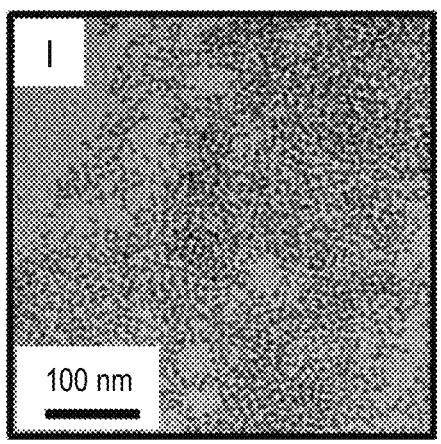
Figure 7J:
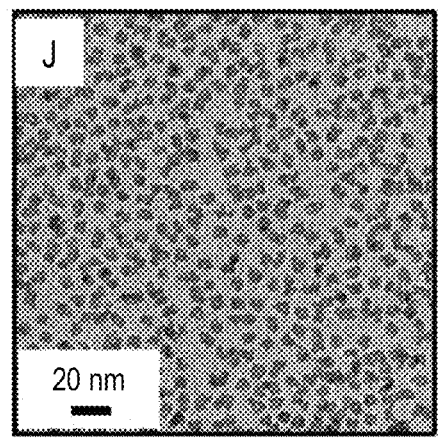

FIGS. 7A-7J are TEM images of nanoparticles prepared in accordance with various aspects of the current technology. FIGS. 7A-7B show $TaO_x$ NC1, FIGS. 7C-7D show $TaO_x$ NC2, FIGS. 7E-7F show $TaO_x$ NC3, FIGS. 7G-7H show $TaO_x$ NC4, and FIGS. 7I-7J show $TaO_x$ NC5.

Figure 8C:
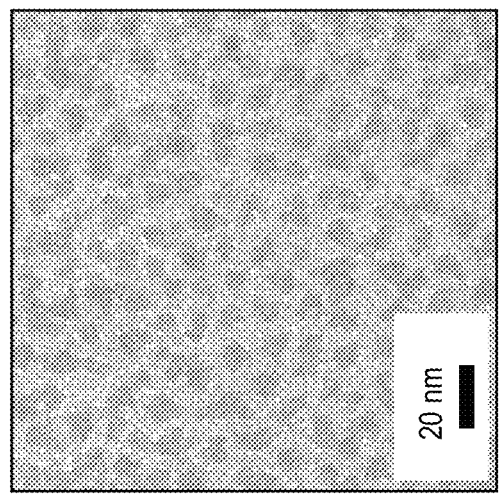
Figure 8B:
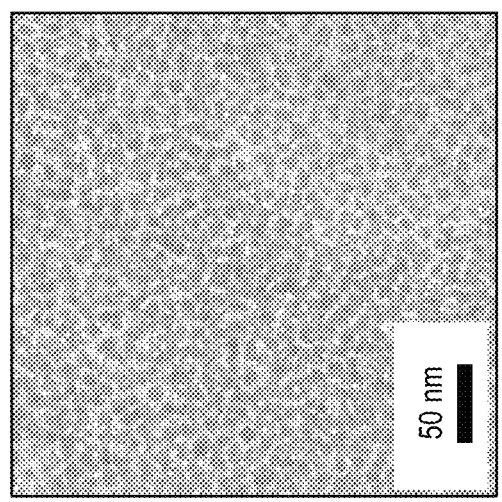
Figure 8A:
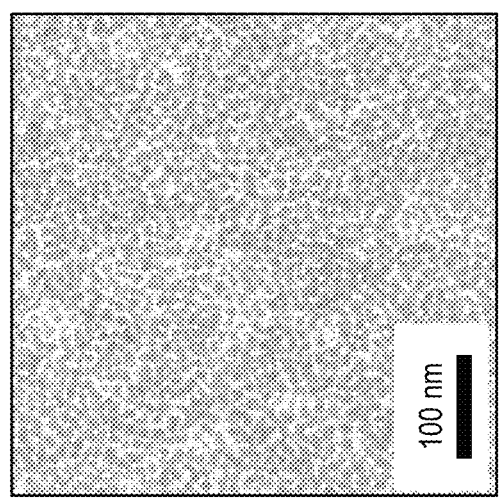

FIGS. 8A-8C are TEM images of $TaO_x$ NC1 prepared in accordance with various aspects of the current technology. FIGS. 8A, 8B, and 8C respectively correspond to $TaO_x$ NC1 obtained from three different batches and show excellent homogeneity in size and morphology.

Figure 9C:
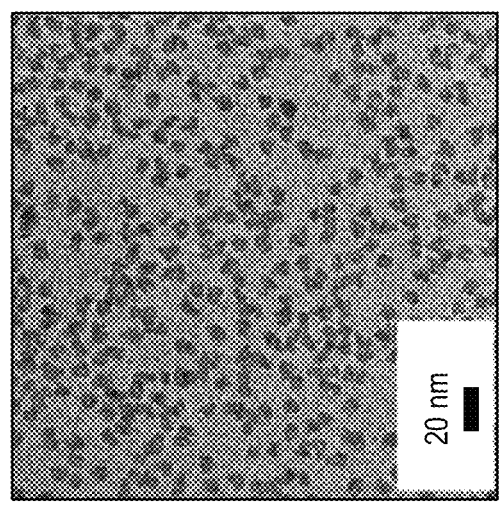
Figure 9B:
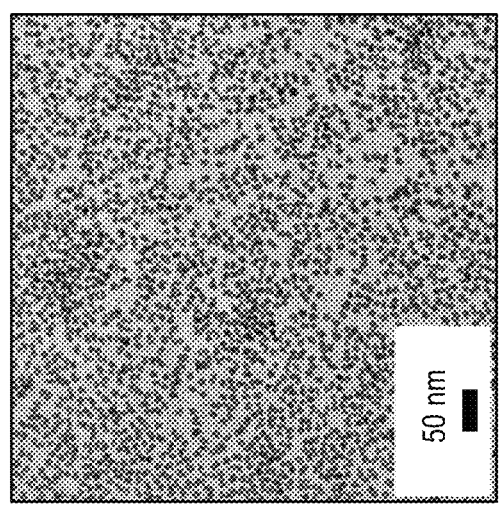
Figure 9A:
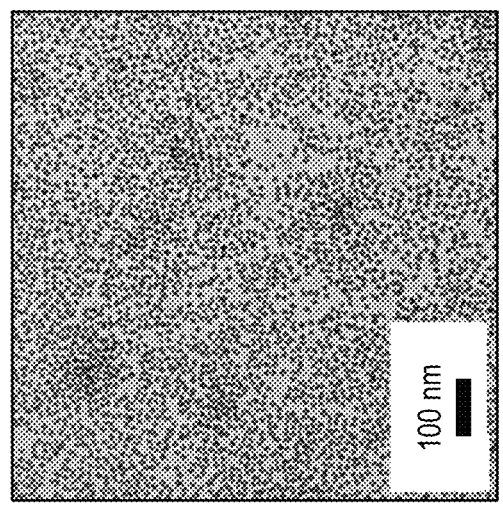

FIGS. 9A-9C are TEM images of $TaO_x$ NC2 prepared in accordance with various aspects of the current technology. FIGS. 9A, 9B, and 9C respectively correspond to $TaO_x$ NC2 obtained from three different batches and show excellent homogeneity in size and morphology.

Figure 10A:
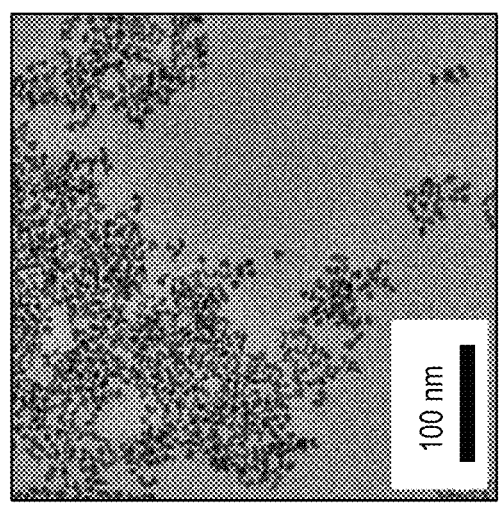
Figure 10B:
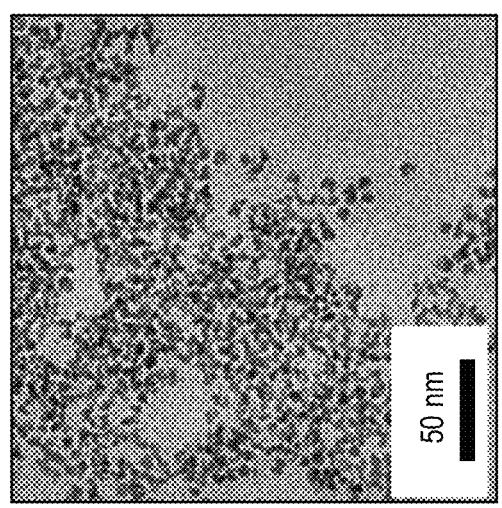
Figure 10C:
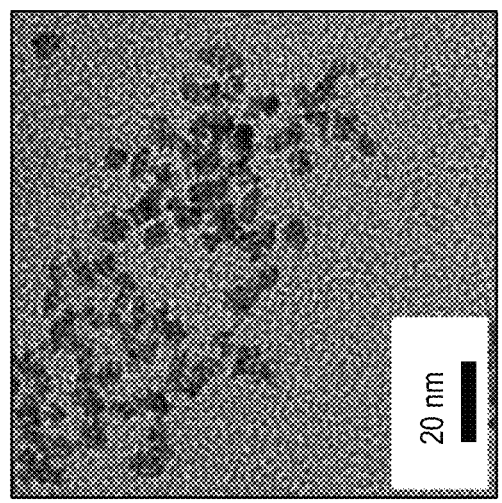

FIGS. 10A-10C are TEM images of $TaO_x$ NC3 prepared in accordance with various aspects of the current technology. FIGS. 10A, 10B, and 10C respectively correspond to $TaO_x$ NC3 obtained from three different batches and show excellent homogeneity in size and morphology.

Figure 11:
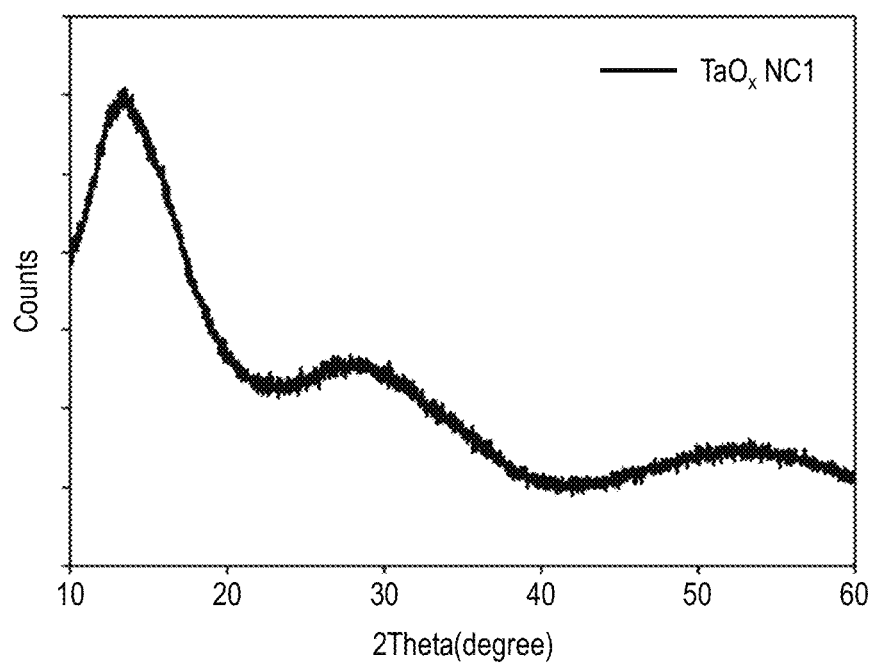

FIG. 11 is an X-ray diffraction (XRD) pattern of $TaO_x$ NC1 prepared in accordance with various aspects of the current technology. XRD patterns were obtained on a Bruker D8 DaVinci diffractometer equipped with Cu X-ray radiation operating at 40 kV and 40 mA. Peak intensities were obtained by counting with the Lynxeye detector every 0.02° at sweep rates of 1.2° 2θ/min. The sample was placed in a PVMA sample holder and rotated at 5 degrees per minute.

Figure 12:
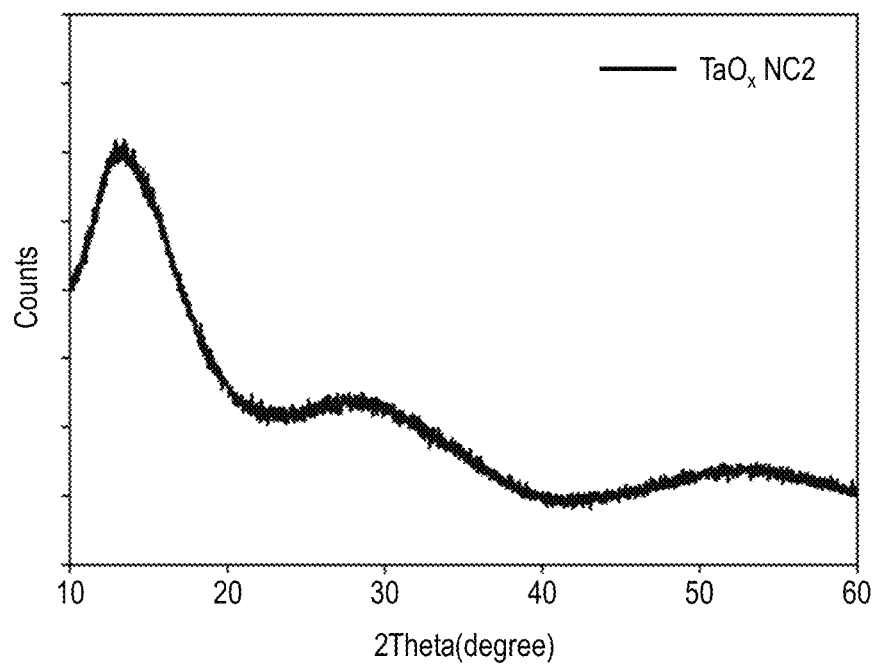

FIG. 12 shows an XRD pattern of TaO$_x$ NC2 prepared in accordance with various aspects of the current technology. XRD patterns were obtained on a Bruker D8 DaVinci diffractometer equipped with Cu X-ray radiation operating at 40 kV and 40 mA. Peak intensities were obtained by counting with the Lynxeye detector every 0.02° at sweep rates of 1.2° 2θ/min. The sample was placed in a PVMA sample holder and rotated at 5 degrees per minute.

Figure 13:
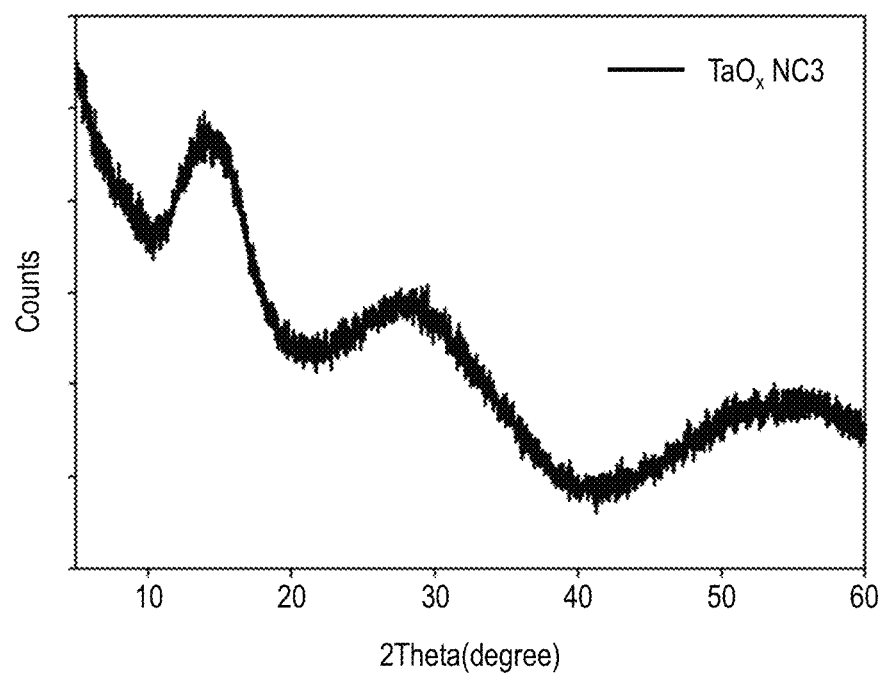

FIG. 13 shows an XRD pattern of TaO$_x$ NC3 prepared in accordance with various aspects of the current technology. XRD patterns were obtained on a Bruker D8 DaVinci diffractometer equipped with Cu X-ray radiation operating at 40 kV and 40 mA. Peak intensities were obtained by counting with the Lynxeye detector every 0.02° at sweep rates of 1.2° 2θ/min. The sample was placed in a PVMA sample holder and rotated at 5 degrees per minute.

FIGS. 14A-14B show energy dispersive spectroscopy (EDS) for TaO$_x$ NC1 prepared in accordance with various aspects of the current technology, showing the presence of Ta and Si in the NCs. The Cu peaks can be ascertained to the grid used for TEM. The peaks for C and Cu in the EDS spectra are attributed to the grid mesh used as a sample holder for TEM imaging.

FIGS. 15A-15B show EDS for TaO$_x$ NC2 prepared in accordance with various aspects of the current technology, showing the presence of Ta and Si in the NCs. The peaks for C and Cu in the EDS spectra are attributed to the grid mesh used as a sample holder for TEM imaging.

Figure 16A:
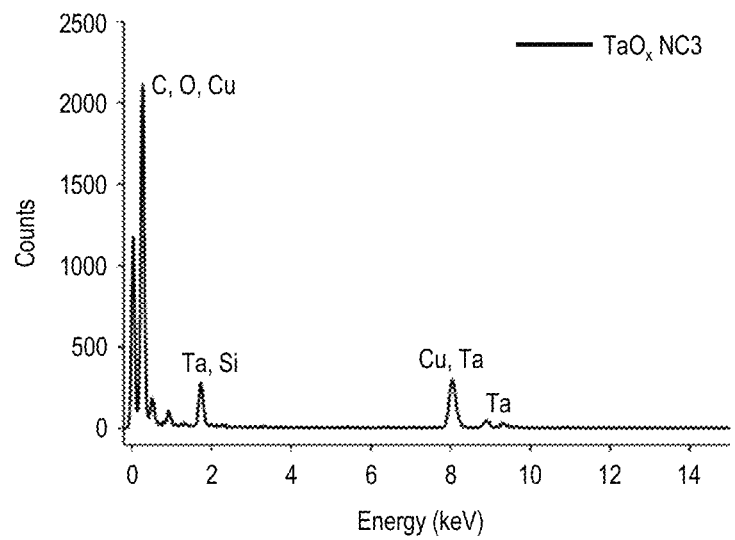
Figure 16B:
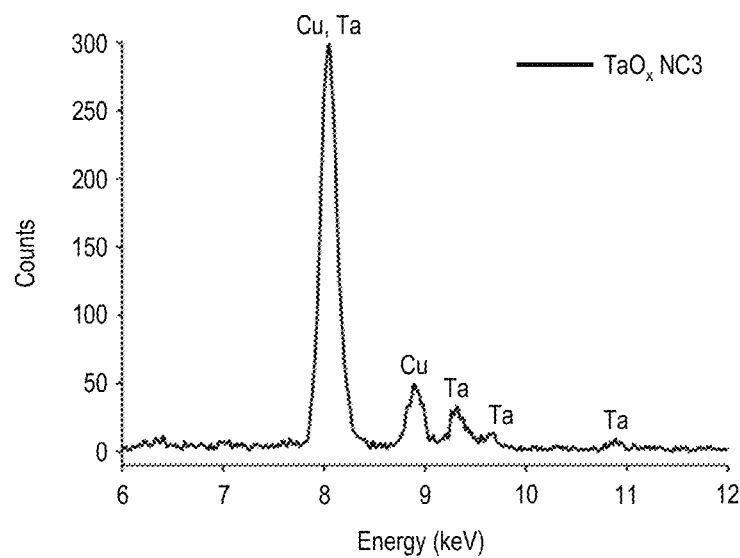

FIGS. 16A-16B show EDS for TaO$_x$ NC3 prepared in accordance with various aspects of the current technology, showing the presence of Ta and Si in the NCs. The peaks for C and Cu in the EDS spectra are attributed to the grid mesh used as a sample holder for TEM imaging.

Figure 17:
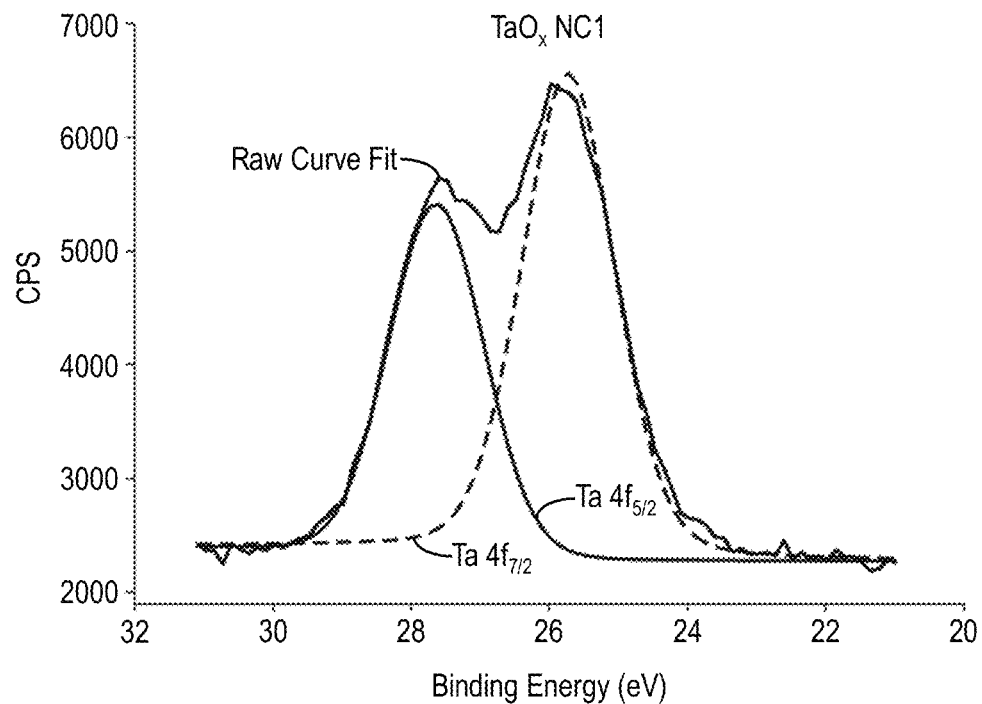

FIG. 17 shows narrow scan X-ray photoelectron spectroscopy (XPS) for TaO$_x$ NC1 prepared in accordance with various aspects of the current technology, showing Ta $4f_{7/2}$ and Ta $4f_{5/2}$ that are close to characteristic Ta$^{2+}$ in TaO, as reported in literature.

Figure 18:
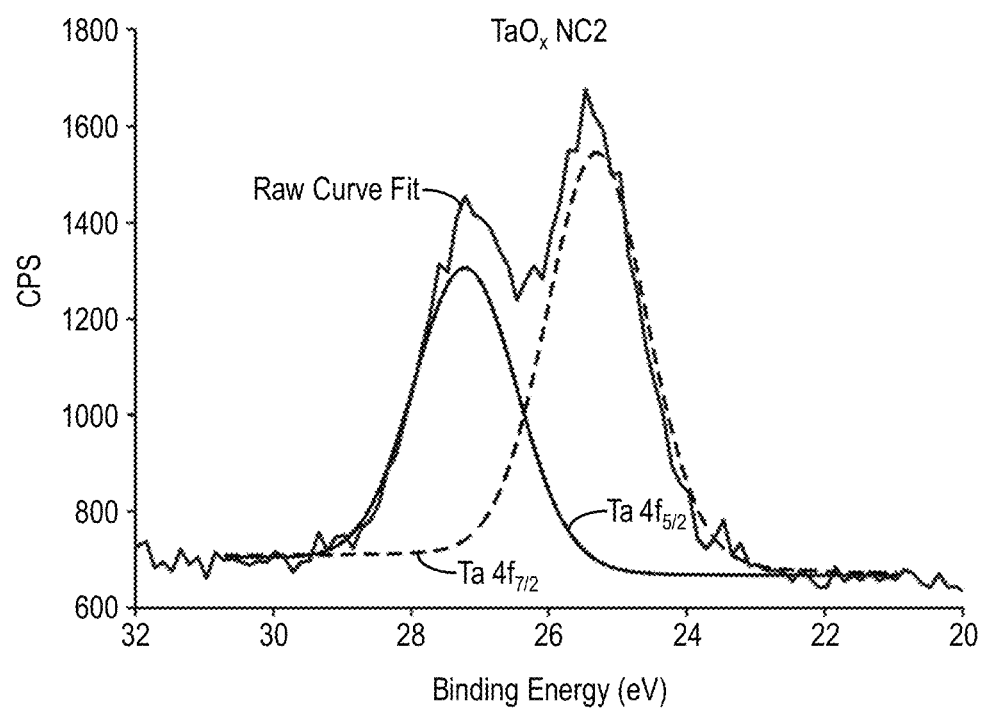

FIG. 18 shows narrow scan XPS for TaO$_x$ NC2 prepared in accordance with various aspects of the current technology, showing Ta $4f_{7/2}$ and Ta $4f_{5/2}$ that are close to characteristic Ta$^{2+}$ in TaO, as reported in literature.

Figure 19:
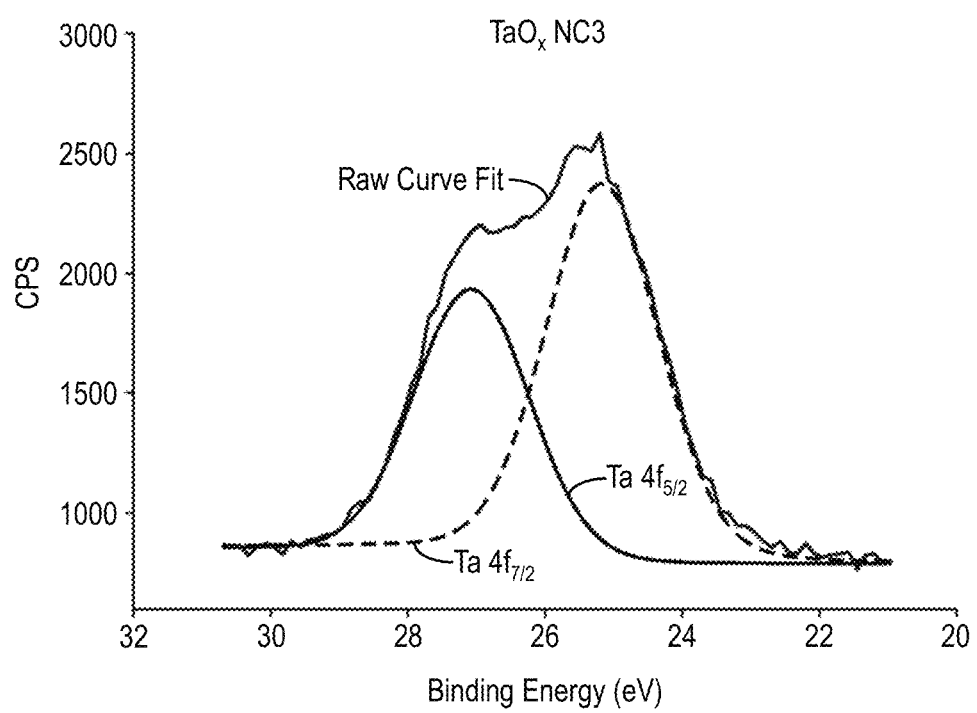
Figure 20A:
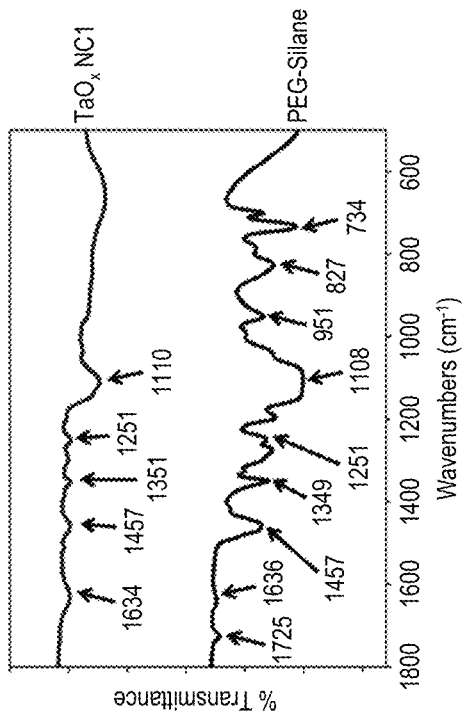
Figure 20B:
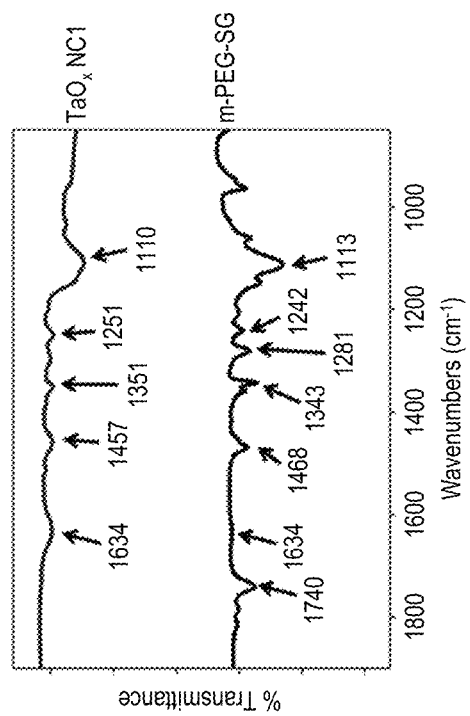
Figure 20C:
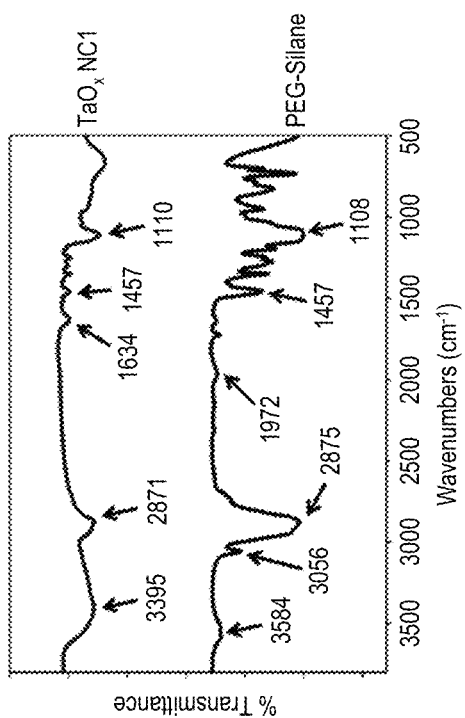
Figure 20D:
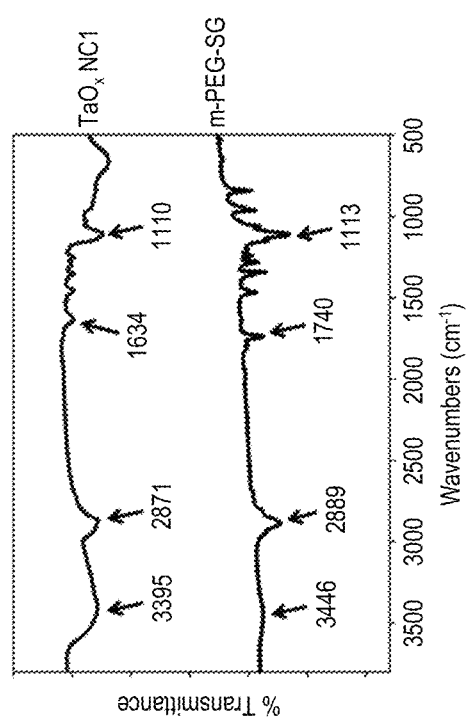

FIG. 19 shows narrow scan XPS for TaO$_x$ NC3 prepared in accordance with various aspects of the current technology, showing Ta $4f_{7/2}$ and Ta $4f_{5/2}$ that are close to characteristic Ta$^{2+}$ in TaO, as reported in literature.

FIGS. 20A-20D show Fourier transform infrared (FTIR) spectra showing the surface coating of PEG-Silane (FIGS. 20A-20B) and methoxy-PEG-succinimidyl glutarate (m-PEG-SG) (FIGS. 20C-20D) on the as-synthesized TaO$_x$ NC1 prepared in accordance with various aspects of the current technology. Prominent and common transmittance peaks are pointed out.

Figure 21A:
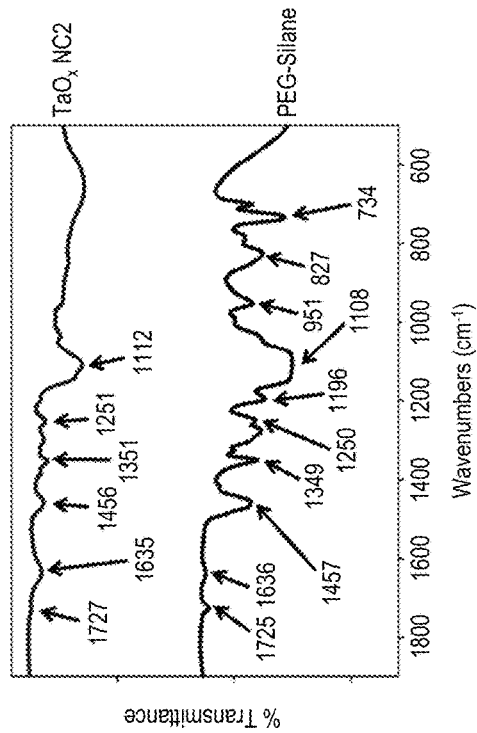
Figure 21B:
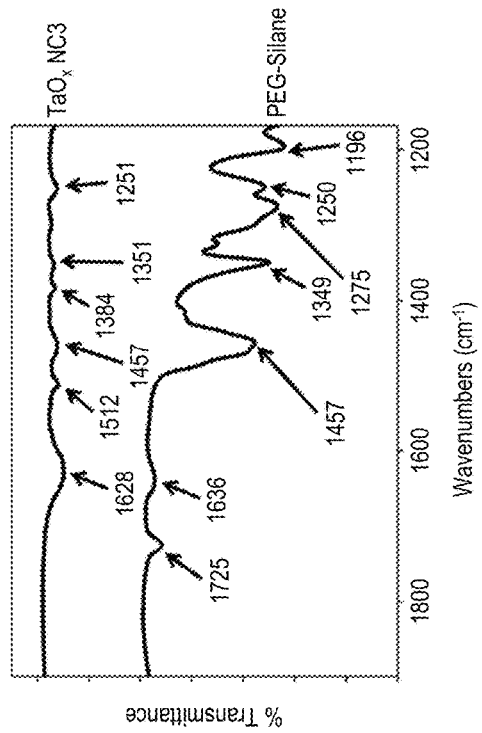

FIGS. 21A-21B show FTIR spectra showing the surface coating of PEG-Silane on the as-synthesized TaO$_x$ NC2 prepared in accordance with various aspects of the current technology. Prominent and common transmittance peaks are pointed out.

Figure 22A:
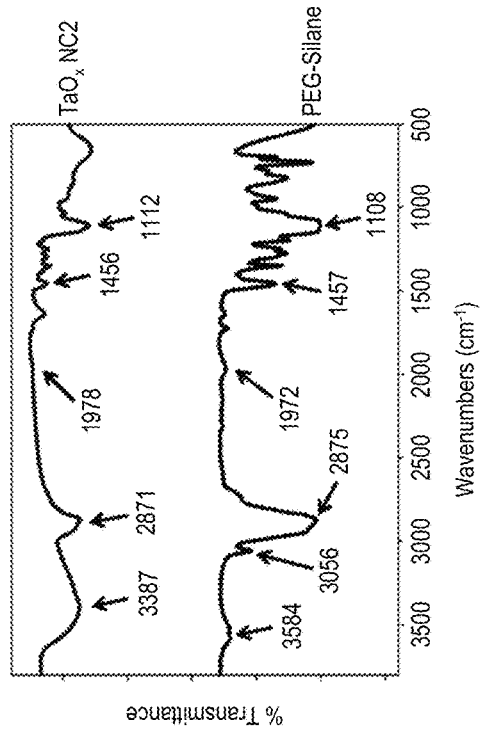
Figure 22B:
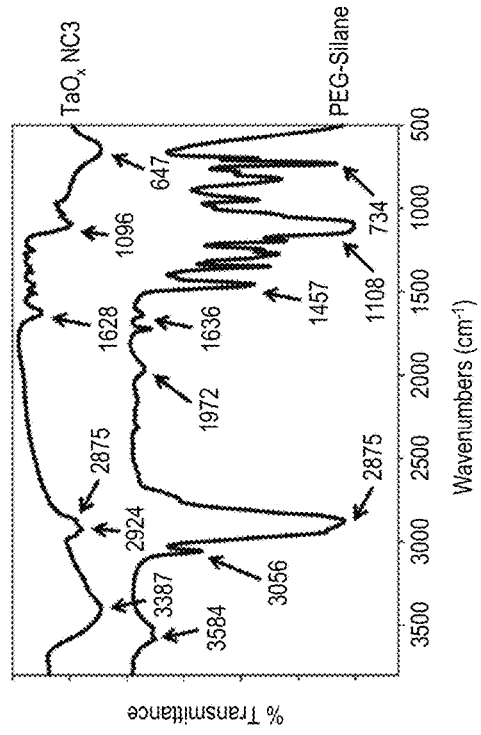

FIGS. 22A-22B show FTIR spectra showing the surface coating of PEG-Silane on the as-synthesized TaO$_x$ NC3 prepared in accordance with various aspects of the current technology. Prominent and common transmittance peaks are pointed out.

Figure 23:
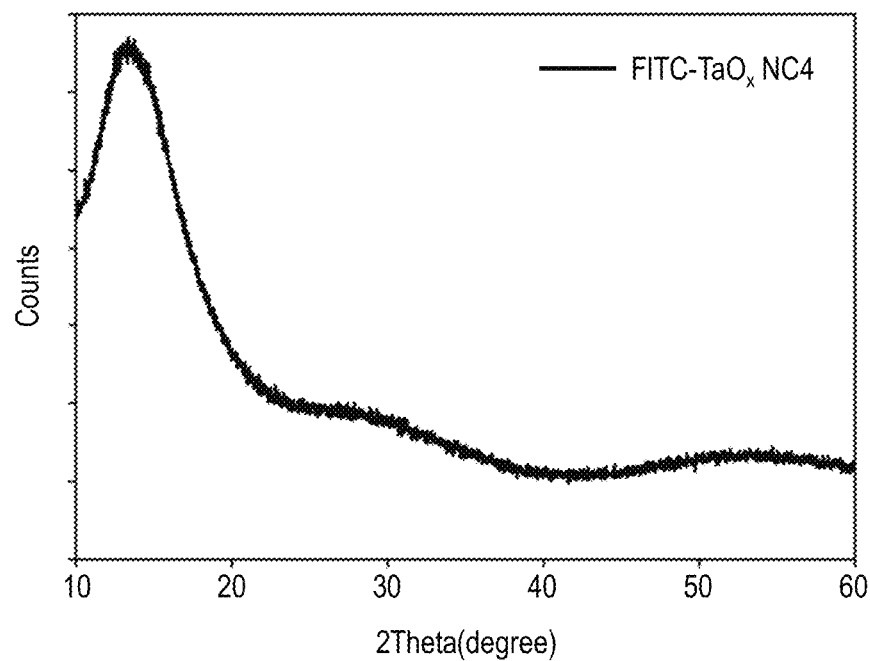

FIG. 23 shows an XRD pattern of TaO$_x$ NC4 prepared in accordance with various aspects of the current technology. XRD patterns were obtained on a Bruker D8 DaVinci diffractometer equipped with Cu X-ray radiation operating at 40 kV and 40 mA. Peak intensities were obtained by counting with the Lynxeye detector every 0.02° at sweep rates of 1.2° 2θ/min. The sample was placed in a PVMA sample holder and rotated at 5 degrees per minute.

Figure 24:
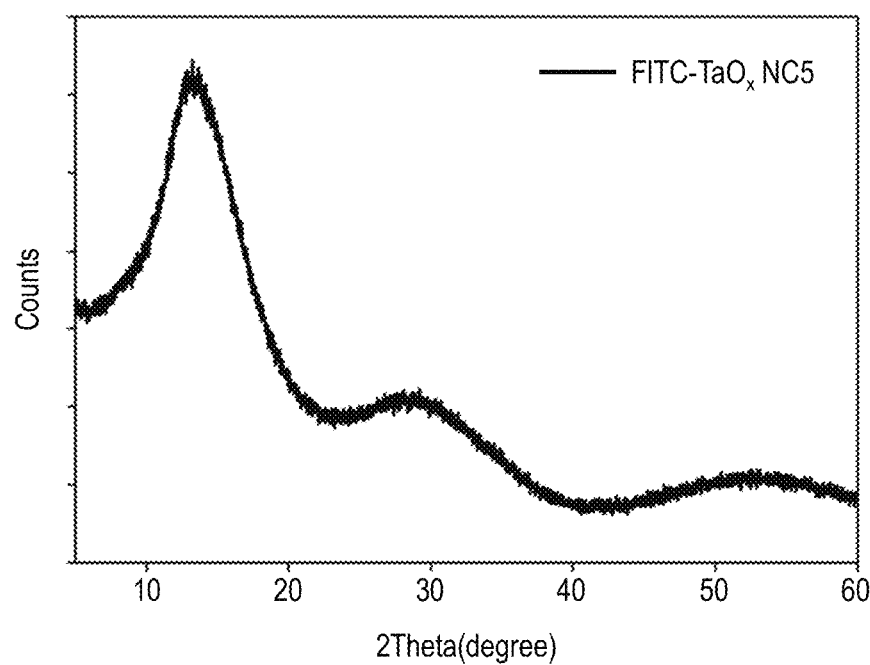

FIG. 24 shows an XRD pattern of TaO$_x$ NC5 prepared in accordance with various aspects of the current technology. XRD patterns were obtained on a Bruker D8 DaVinci diffractometer equipped with Cu X-ray radiation operating at 40 kV and 40 mA. Peak intensities were obtained by counting with the Lynxeye detector every 0.02° at sweep rates of 1.2° 2θ/min. The sample was placed in a PVMA sample holder and rotated at 5 degrees per minute.

Figure 25C:
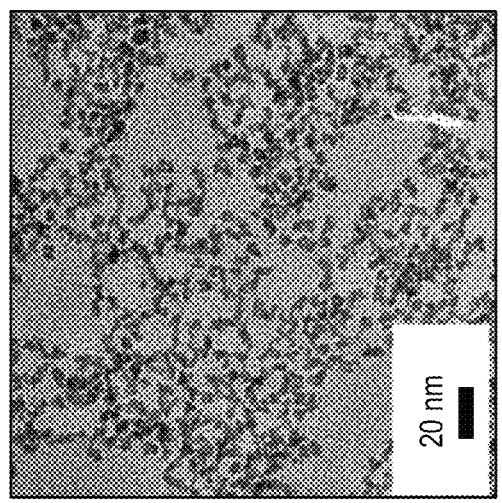
Figure 25B:
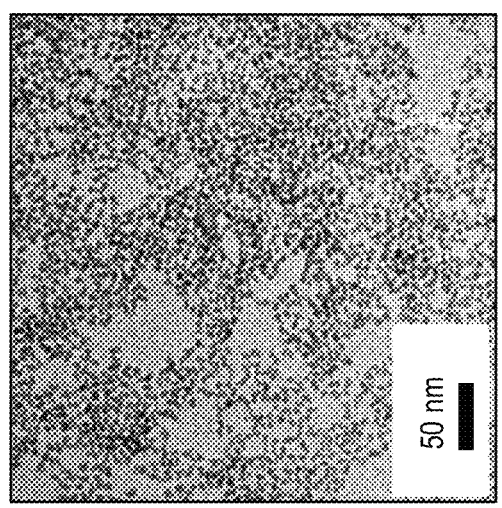
Figure 25A:
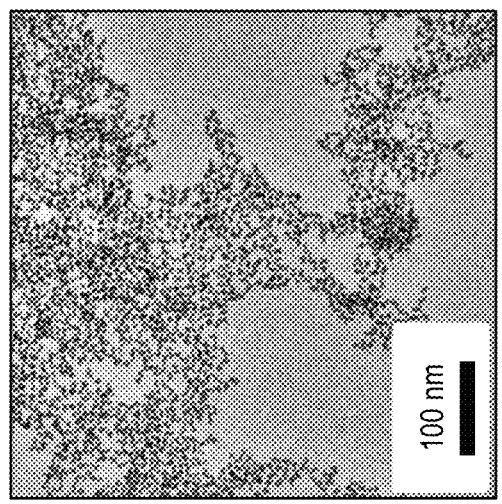

FIGS. 25A-25C are TEM images of FITC-TaO$_x$ NC4 prepared in accordance with various aspects of the current technology. FIGS. 25A, 25B, and 25C respectively correspond to FITC-TaO$_x$ NC4 obtained from three different batches and show excellent homogeneity in size and morphology.

Figure 26C:
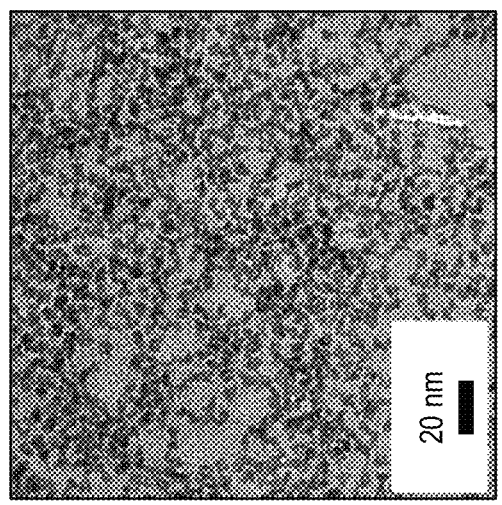
Figure 26B:
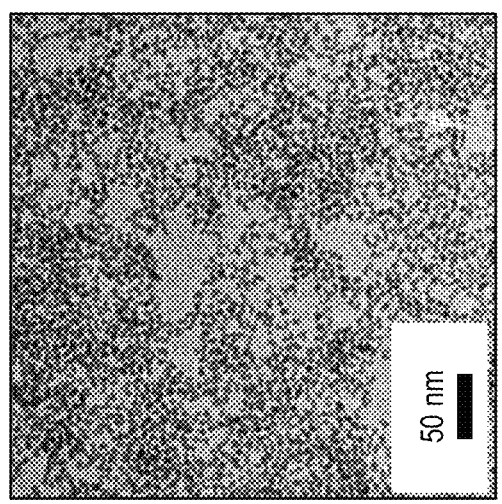
Figure 26A:
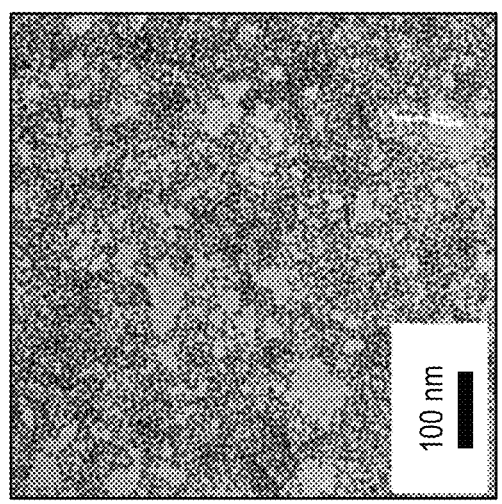
Figure 27B:
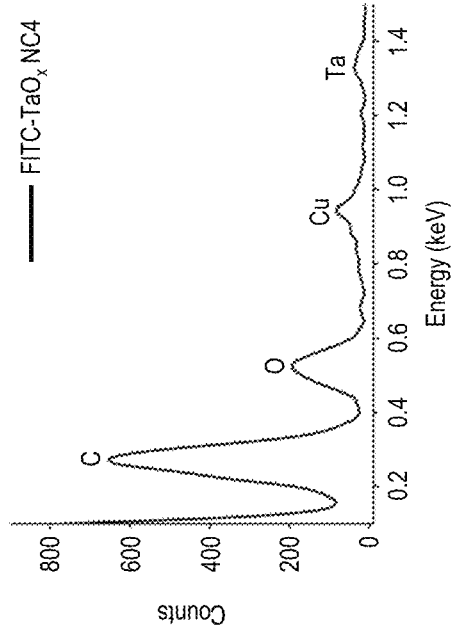
Figure 27D:
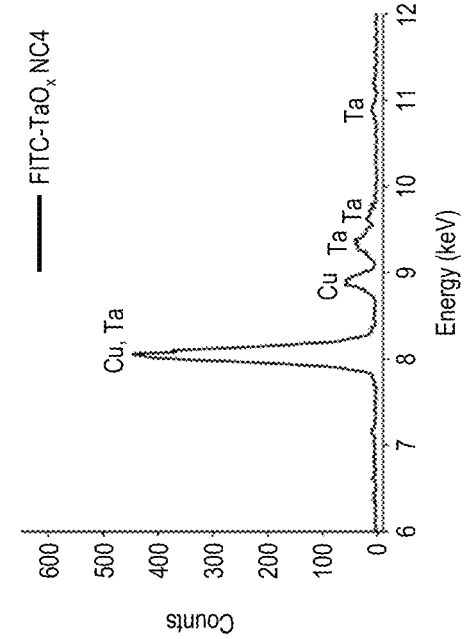
Figure 27A:
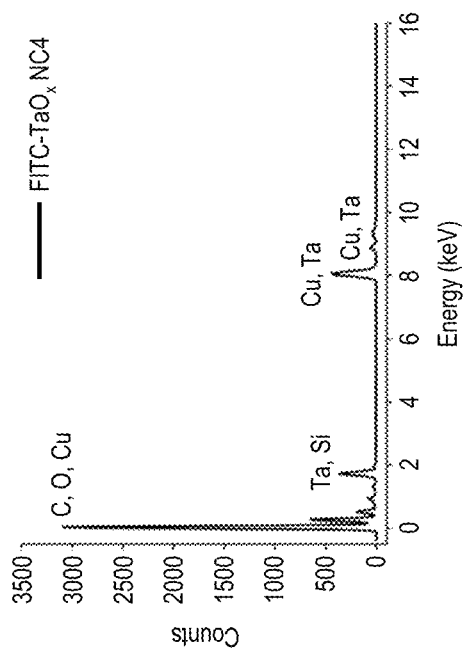
Figure 27C:
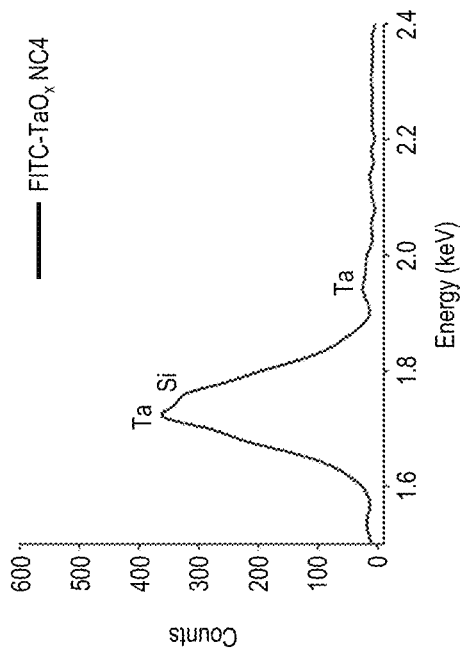

FIGS. 26A-26C are TEM images of FITC-TaO$_x$ NC5 prepared in accordance with various aspects of the current technology. FIGS. 26A, 26B, and 26C respectively correspond to FITC-TaO$_x$ NC5 obtained from three different batches and show excellent homogeneity in size and morphology.

FIGS. 27A-27D show EDS for FITC-TaO$_x$ NC4 prepared in accordance with various aspects of the current technology, showing the presence of Ta and Si in the NCs. The peaks for C and Cu in the EDS spectra are attributed to the grid mesh used as a sample holder for TEM imaging.

FIGS. 28A-28C show EDS for FITC-TaO$_x$ NC5 prepared in accordance with various aspects of the current technology, showing the presence of Ta and Si in the NCs. The peaks for C and Cu in the EDS spectra are attributed to the grid mesh used as a sample holder for TEM imaging.

Figure 29:
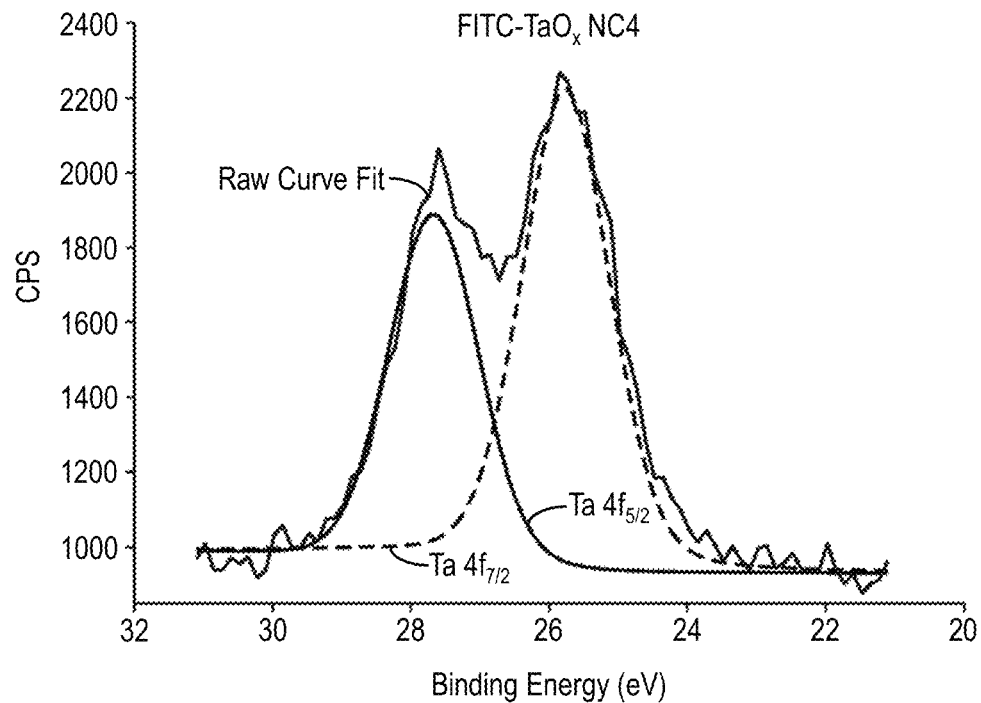

FIG. 29 shows narrow scan XPS for FITC-TaO$_x$ NC4 prepared in accordance with various aspects of the current technology, showing Ta $4f_{7/2}$ and Ta $4f_{5/2}$ that are close to characteristic Ta$^{2+}$ in TaO, as reported in literature.

Figure 30:
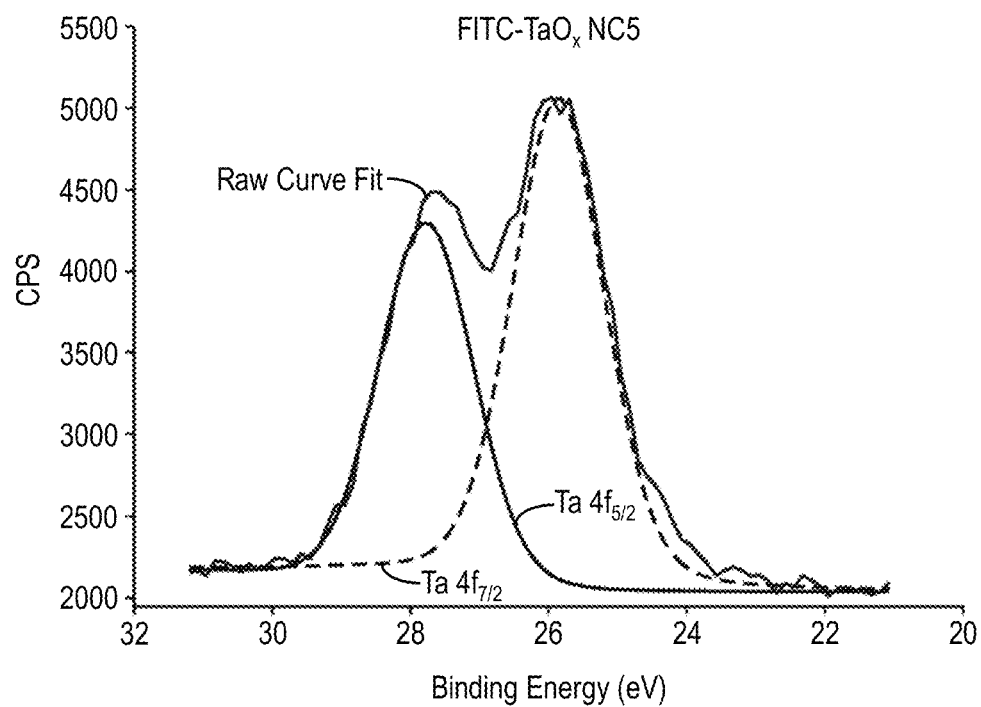
Figure 31A:
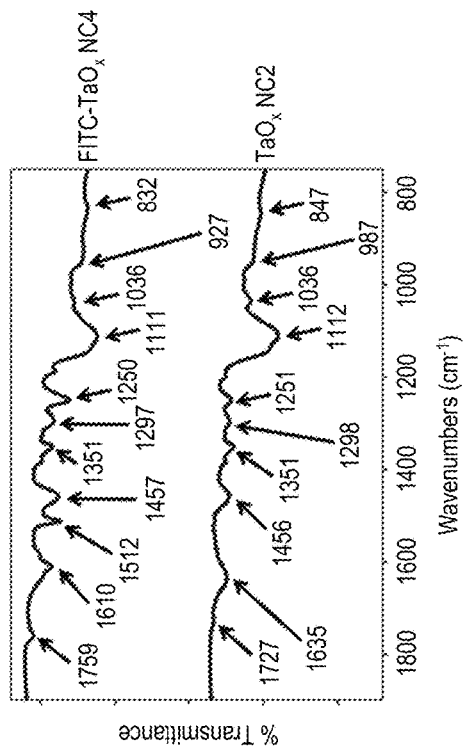
Figure 31B:
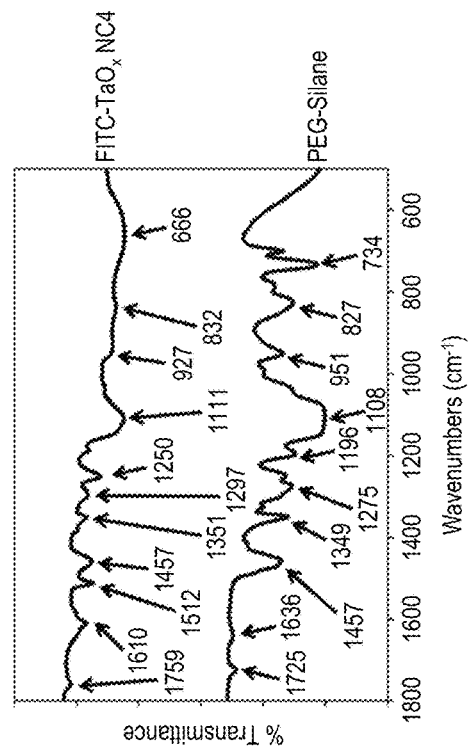
Figure 31C:
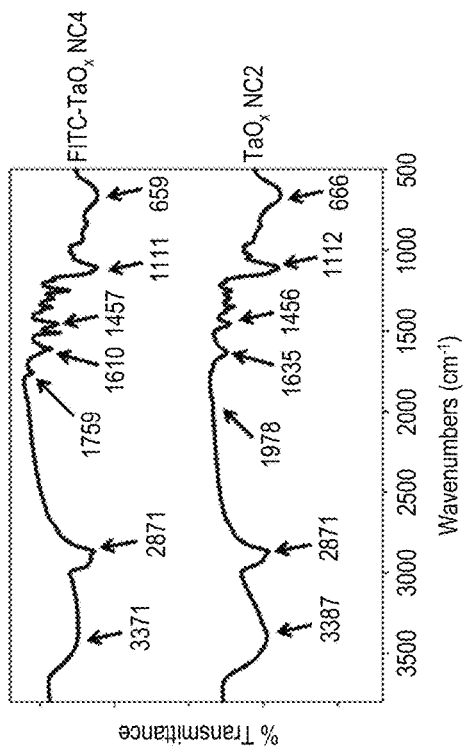
Figure 31D:
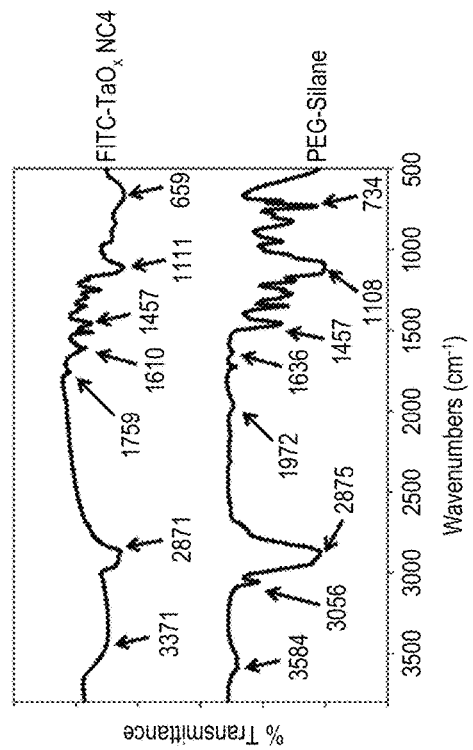

FIG. 30 shows narrow scan XPS for FITC-TaO$_x$ NC5 prepared in accordance with various aspects of the current technology, showing Ta $4f_{7/2}$ and Ta $4f_{5/2}$ that are close to characteristic Ta$^{2+}$ in TaO, as reported in literature.

FIGS. 31A-31D show FTIR spectra comparing the as-synthesized FITC-TaO$_x$ NC4 prepared in accordance with various aspects of the current technology with the starting TaO$_x$ NC2 (FIGS. 31A-31B) and the surface coating of PEG-Silane (FIGS. 31C-31D) on the as-synthesized FITC-TaO$_x$ NC4. Prominent and common transmittance peaks are pointed out.

FIGS. 32A-32B show FTIR spectra comparing the as-synthesized FITC-TaO$_x$ NC4 prepared in accordance with various aspects of the current technology with FITC. The peak at 2035 cm$^{-1}$ in FITC corresponds to the isothiocyanate group that undergoes reaction with APTMS to generate a linker for subsequent reaction with TaO$_x$ NC2 surface silane groups and is consequently absent in the product spectrum. Prominent and common transmittance peaks are pointed out.

FIGS. 33A-33B show FTIR spectra comparing the as-synthesized FITC-TaO$_x$ NC5 prepared in accordance with various aspects of the current technology with the starting TaO$_x$ NC2. Prominent and common transmittance peaks are pointed out.

Figure 34A:
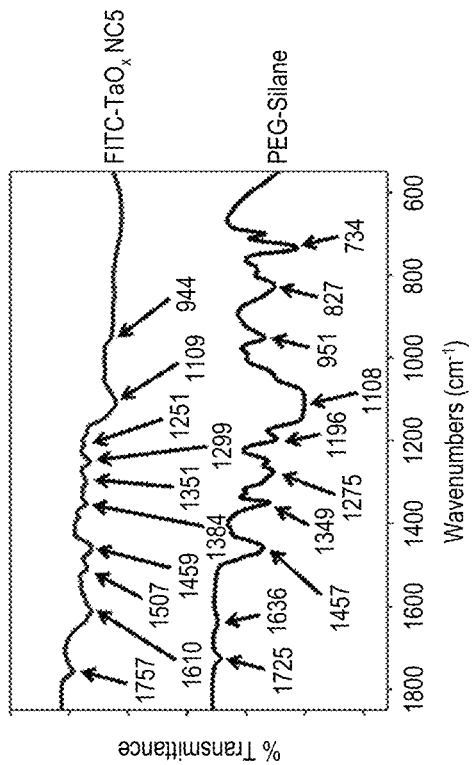
Figure 34B:
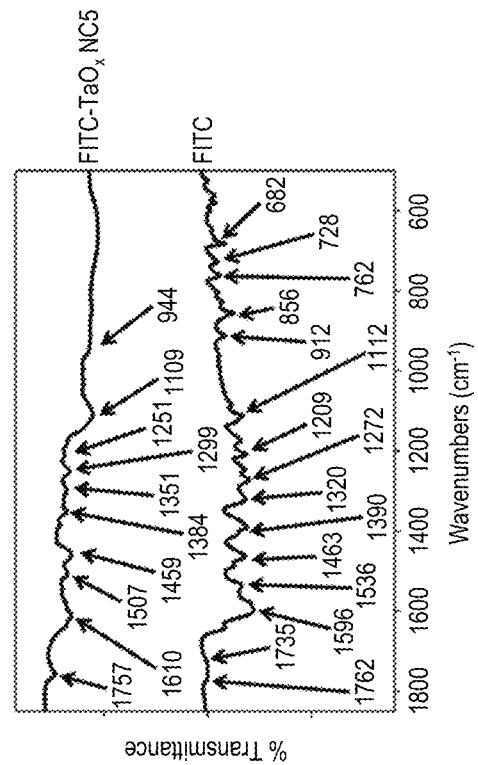
Figure 34C:
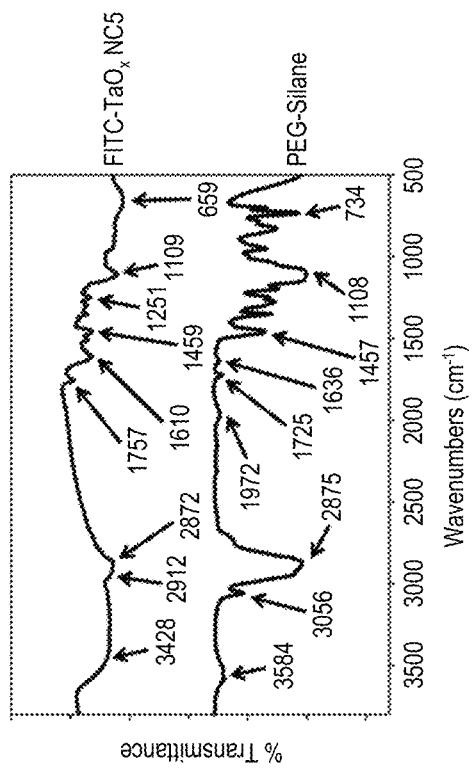
Figure 34D:
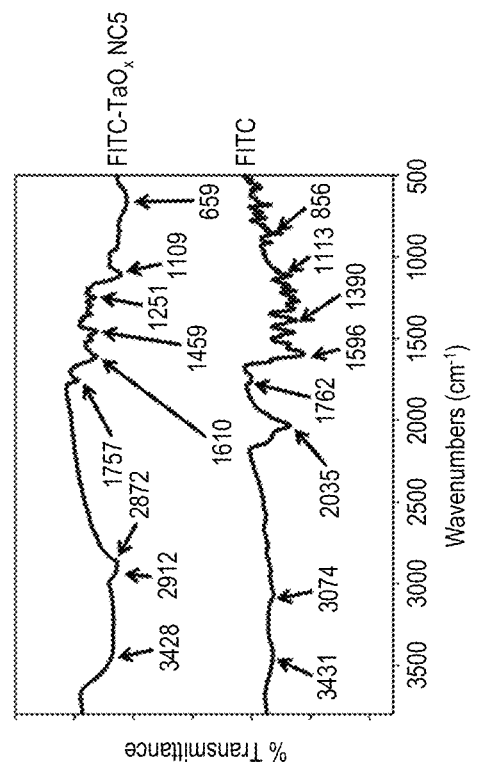

FIGS. 34A-34D show FTIR spectra comparing the as-synthesized FITC-TaO$_x$ NC5 prepared in accordance with various aspects of the current technology with the starting materials, PEG-Silane (FIGS. 34A-34B) and FITC (FIGS. 34C-34D). Prominent and common transmittance peaks are pointed out.

Figure 35:
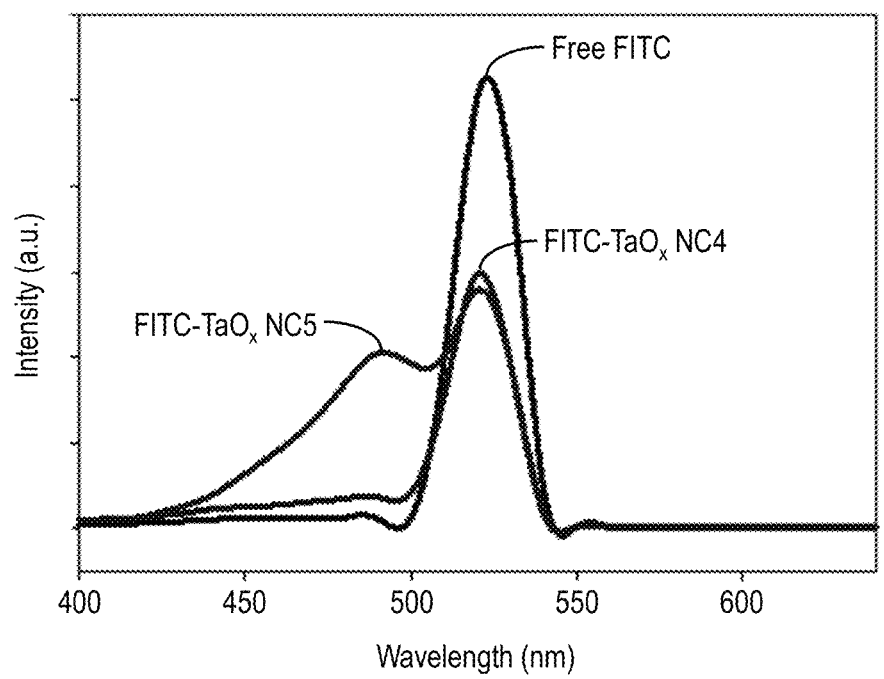

FIG. 35 shows fluorescence spectra for free FITC and FITC-labeled TaO$_x$ NCs prepared in accordance with various aspects of the current technology.

Figure 36A:
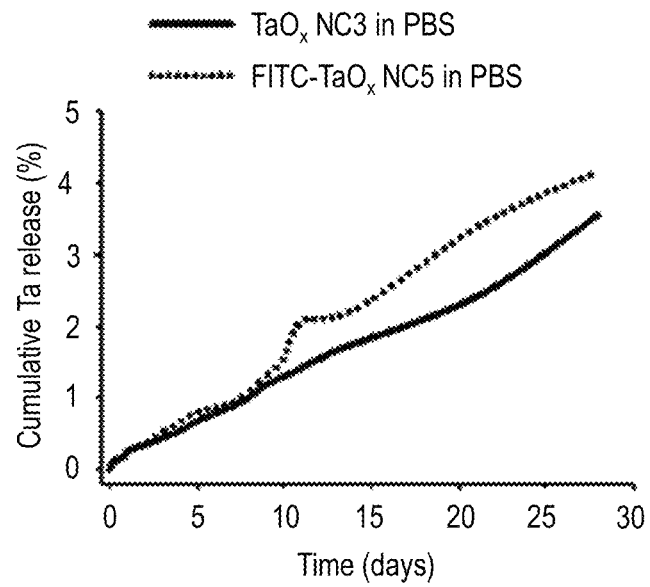
Figure 36B:
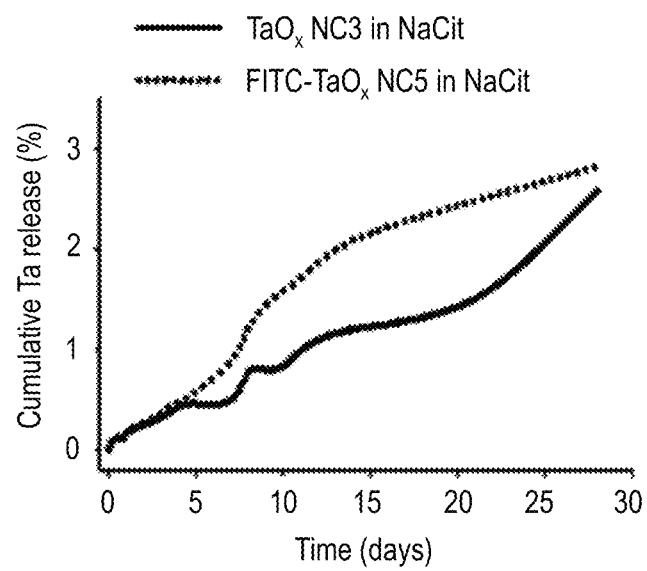

FIGS. 36A-36B are graphs showing Ta dissolution from TaO$_x$ NC3 and FITC-TaO$_x$ NC5 prepared in accordance with various aspects of the current technology over 4 weeks using inductively coupled plasma optical emission spectroscopy (ICP-OES) (n=3, S.D.<0.5). In FIG. 36A, the TaO$_x$ NC3 and FITC-TaO$_x$ NC5 are in phosphate buffered saline (PBS, pH 7.4), and in FIG. 36B, the TaO$_x$ NC3 and FITC-TaO$_x$ NC5 are in sodium citrate (NaCit, pH 5.5).

Figure 37A:
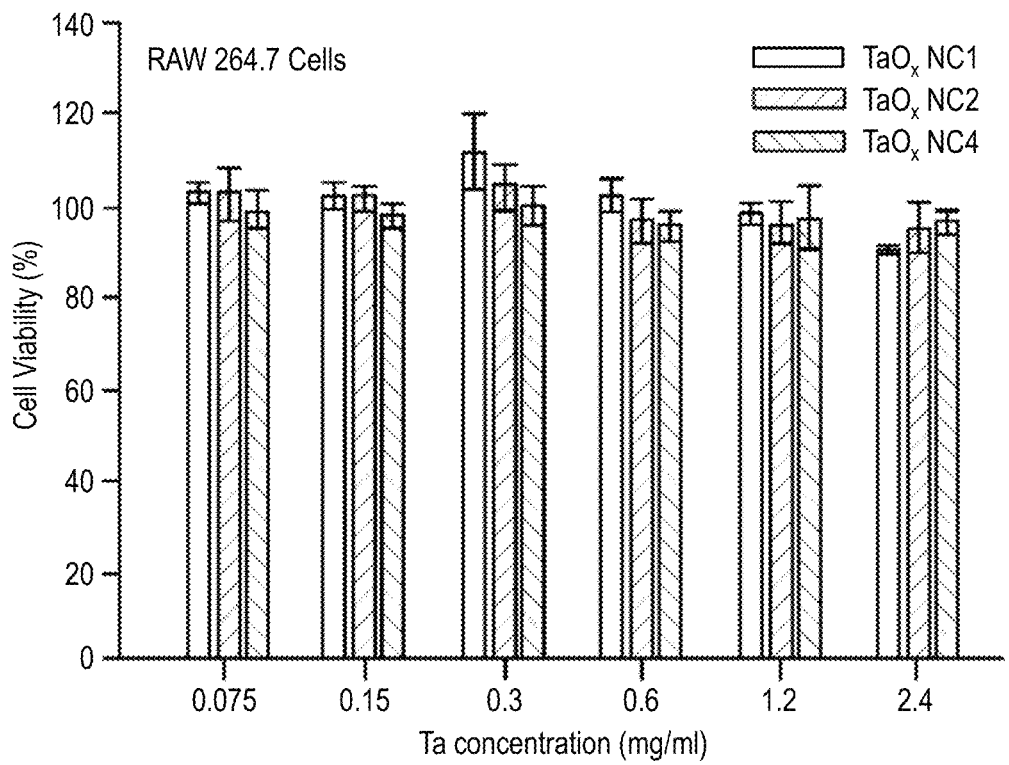
Figure 37B:
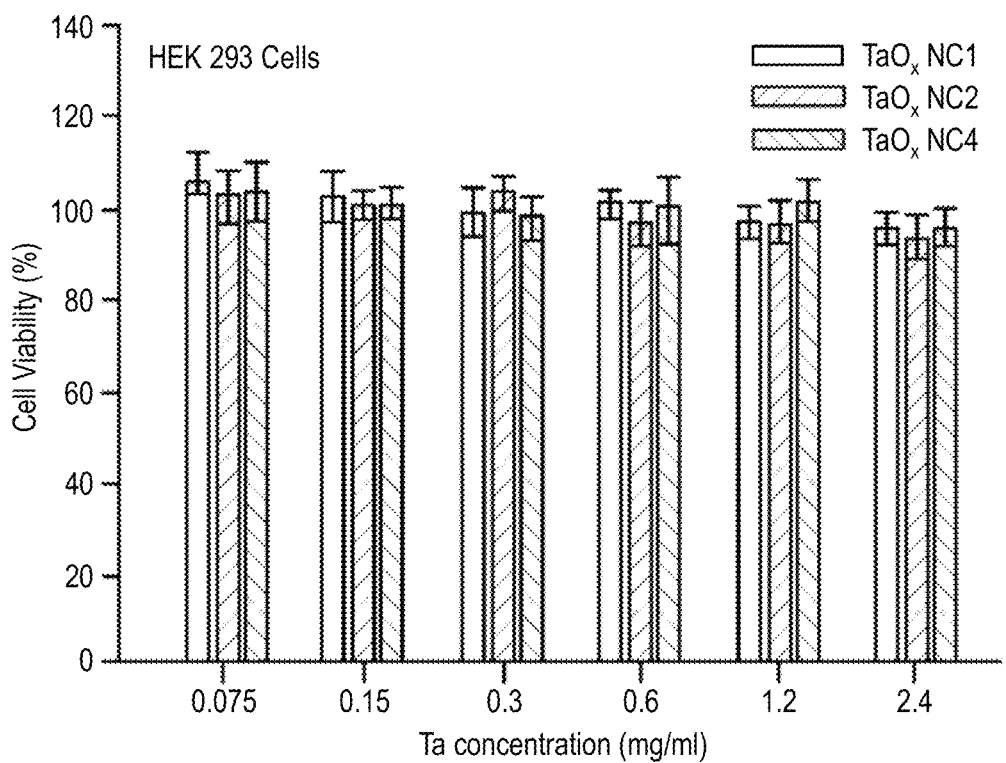

FIGS. 37A-37B are bar graphs showing the results of an MTT cytotoxicity assay for different concentrations of various TaO$_x$ NC types prepared in accordance with various aspects of the current technology incubated with cultured RAW 264.7 macrophage cells (FIG. 37A) and HEK 293 fibroblast cells (FIG. 37B) for 24 hours each.

Figure 38A:
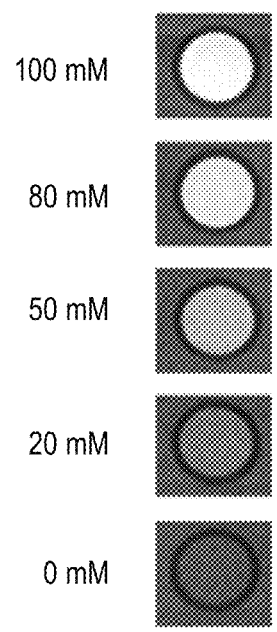
Figure 38B:
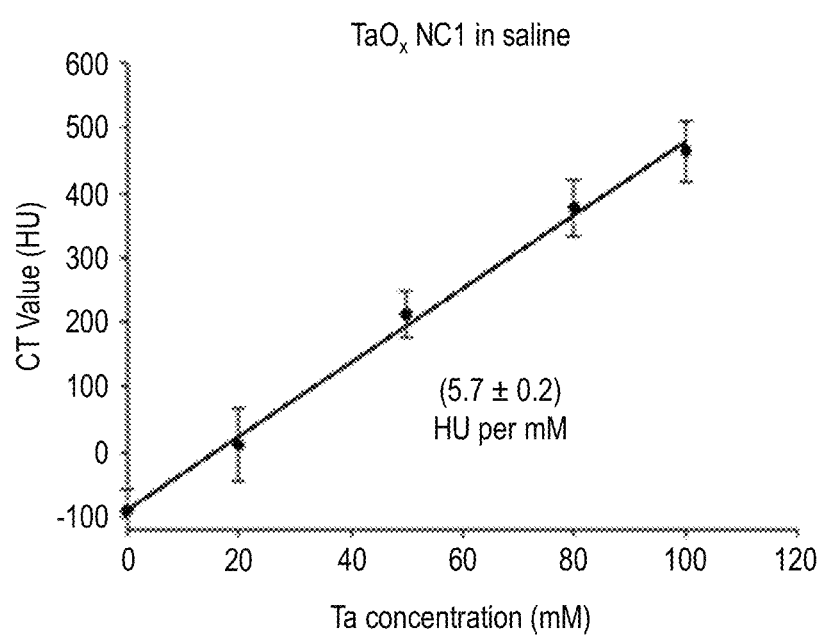

FIGS. 38A-38B show aspects of TaO$_x$ NC1. FIG. 38A shows micro-CT phantom imaging of TaO$_x$ NC1 prepared in accordance with various aspects of the current technology in saline at different Ta concentrations, and FIG. 38B shows linear fitting of CT values as a function of the concentration of Ta in TaO$_x$ NC1 in saline. The linear regression equation is Y=5.69X−89.58, R$^2$=0.9962.

Figure 39:
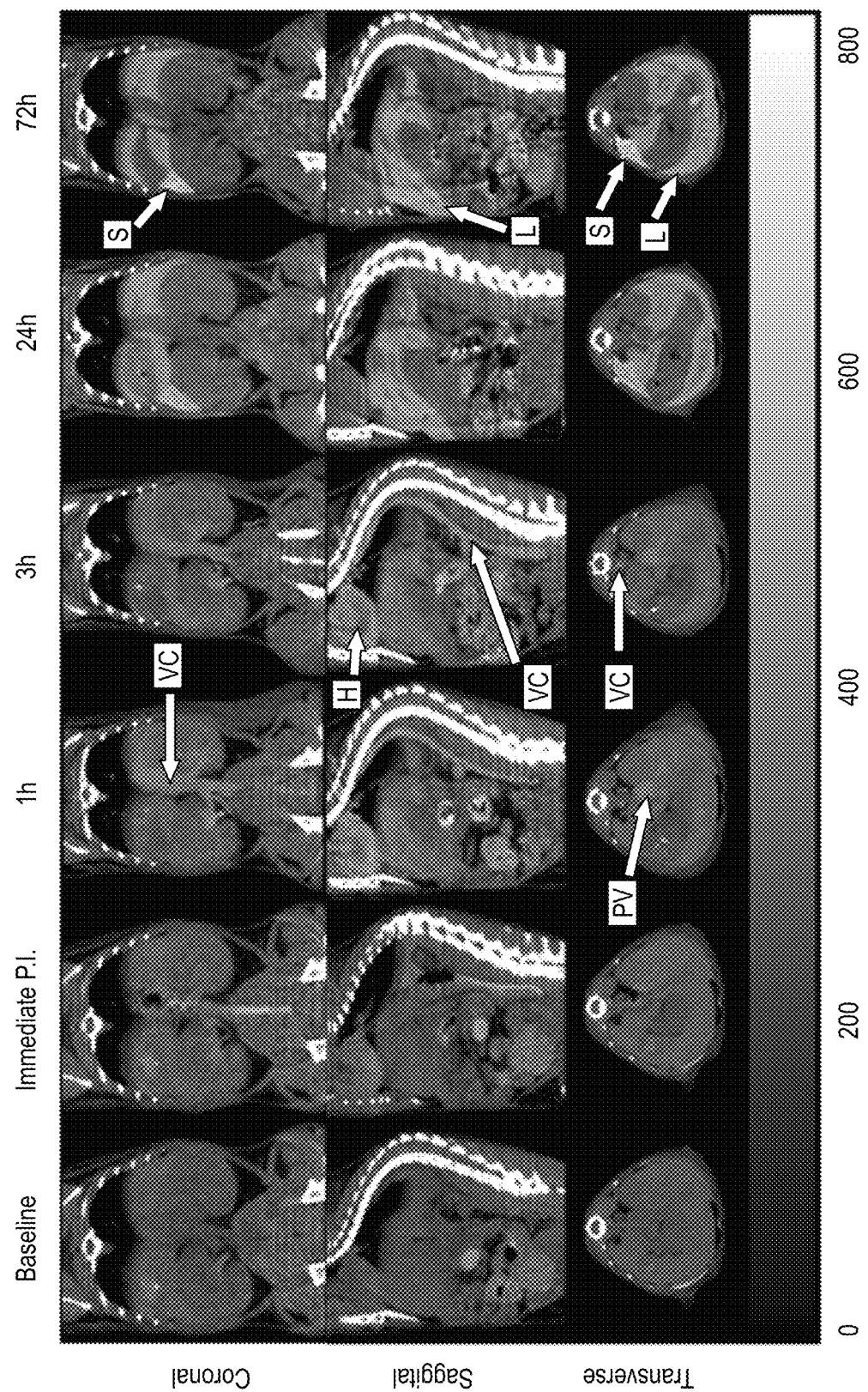

FIG. 39 shows in vivo X-ray micro-CT imaging. Orthogonal views (coronal, sagittal, transverse) of the same representative BALB/c mouse at serial scan time points (0 hour baseline, immediate post-injection, and 1, 3, 24, 72 hours post-injection) of a single, bolus dose (217 μL, 592.3 mg kg$^{-1}$, IV) 200 mM TaO$_x$ NC1 prepared in accordance with various aspects of the current technology. The Hounsfield Unit (HU) scale bar shows hyperintensity of vena cava (VC), spleen (S), heart (H), liver (L), and portal vein (PV).

Figure 40:
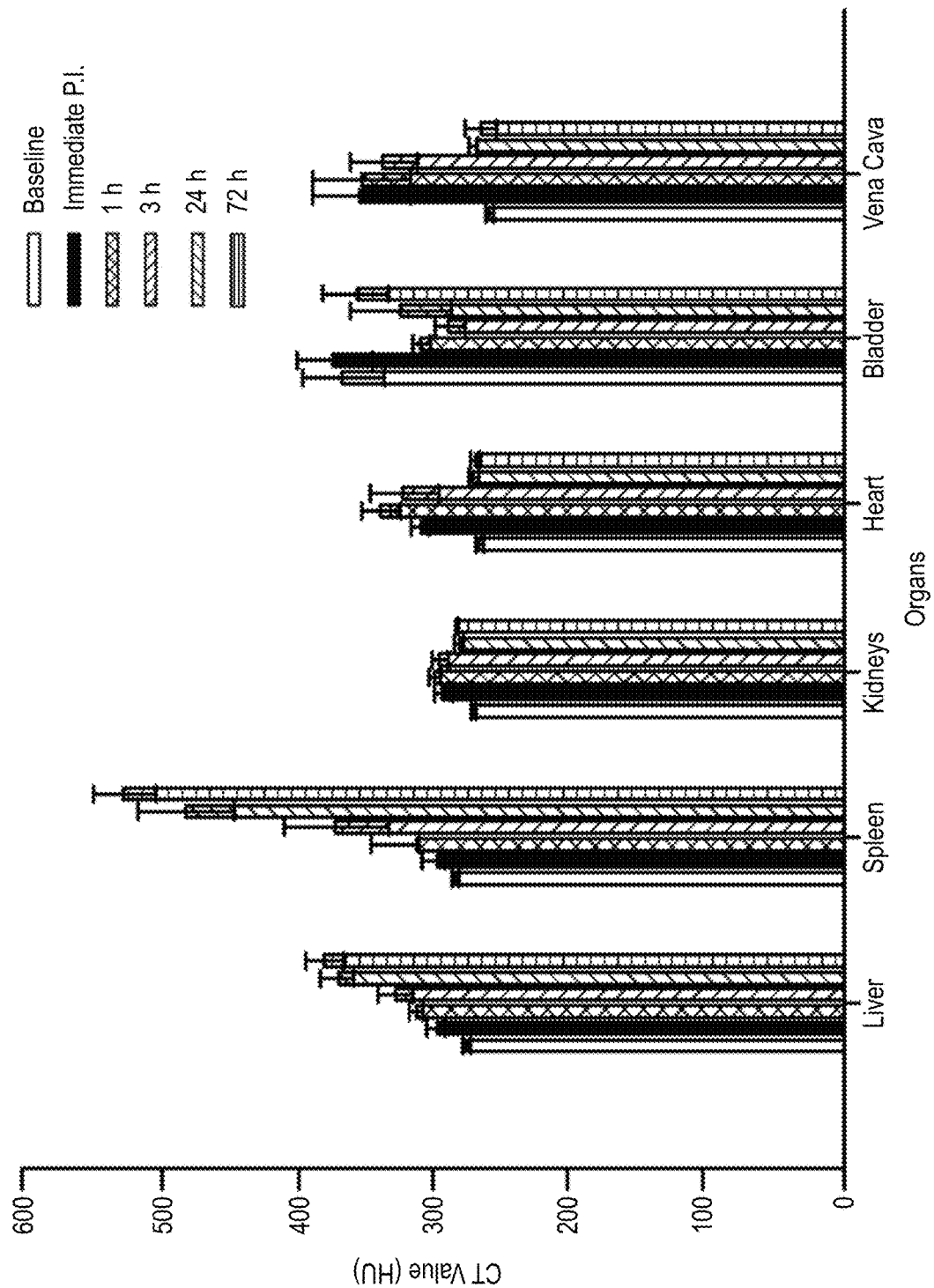

FIG. 40 shows time course CT enhancement in various organs. CT values (HU) of different organs are shown across various time points before (baseline) and after a single, bolus dose (217 μL, 592.3 mg kg$^{-1}$, IV) of 200 mM TaO$_x$ NC1 prepared in accordance with various aspects of the current technology.

Figure 41A:
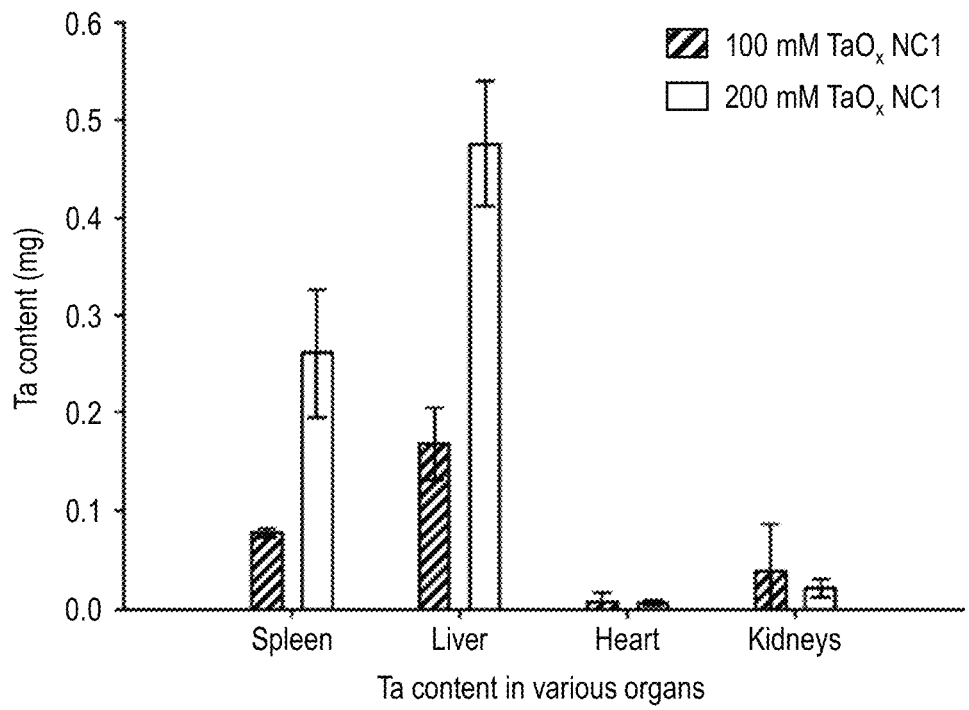
Figure 41B:
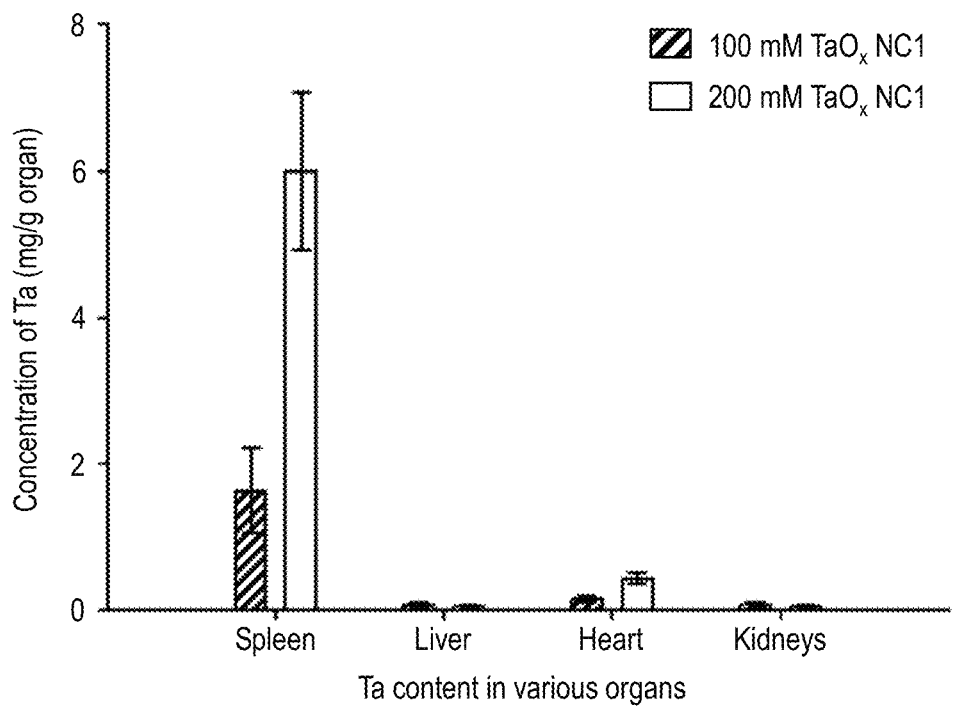

FIGS. 41A-41B show the Ta content in various organs of mice injected with 200 mM TaO$_x$ NC1 prepared in accordance with various aspects of the current technology as analyzed by ICP-OES (n=3, S.D.<0.5).

Figure 42:
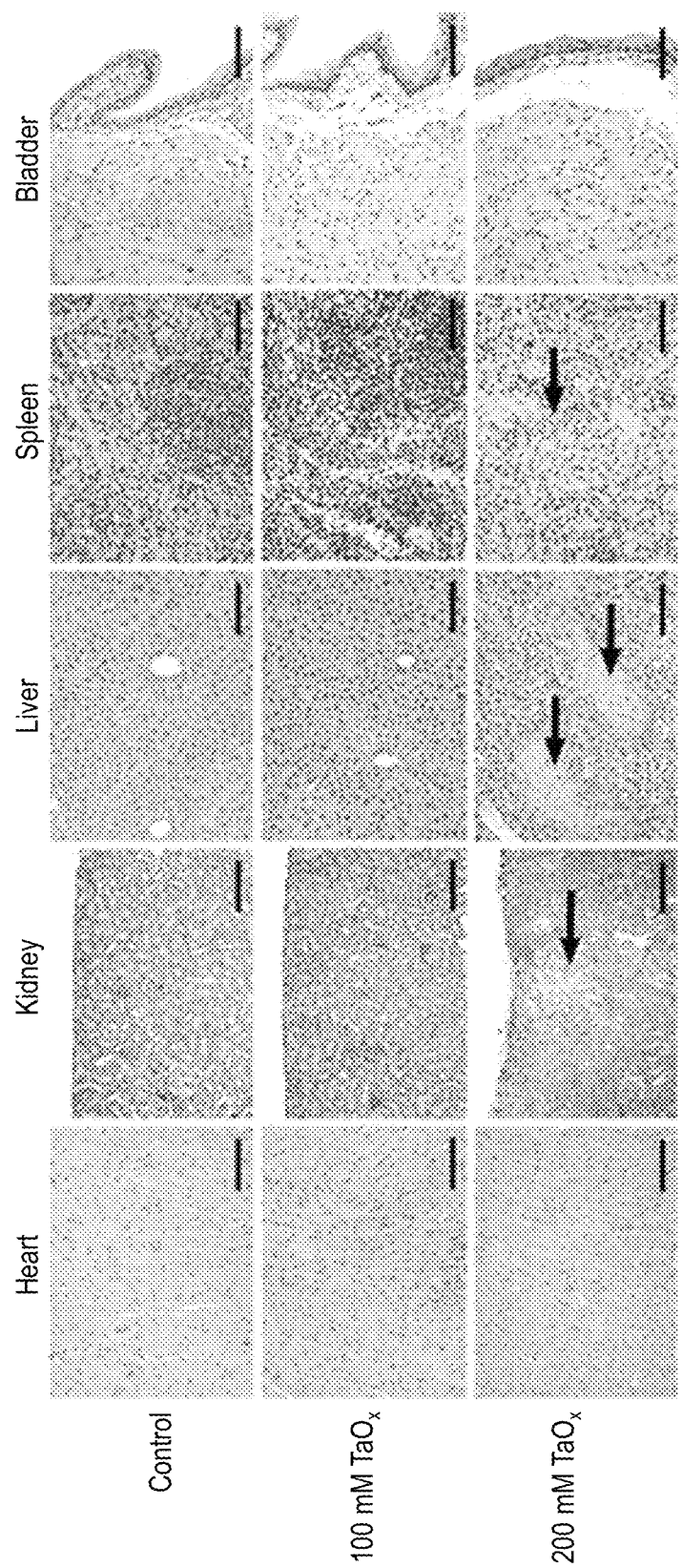
Figure 43A:
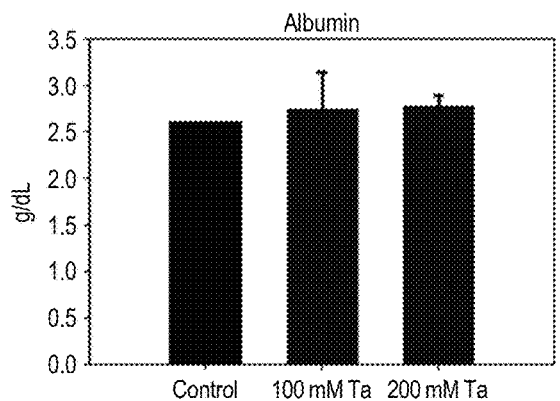
Figure 43B:
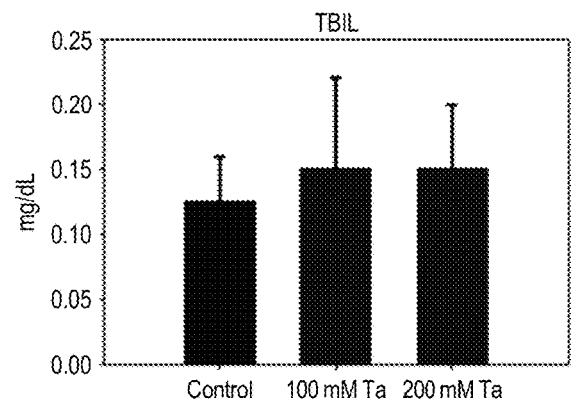
Figure 43C:
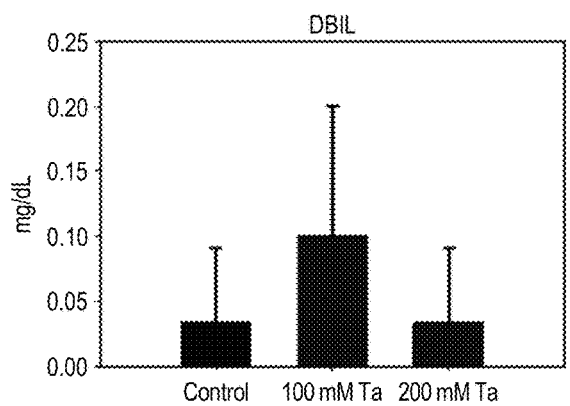
Figure 43D:
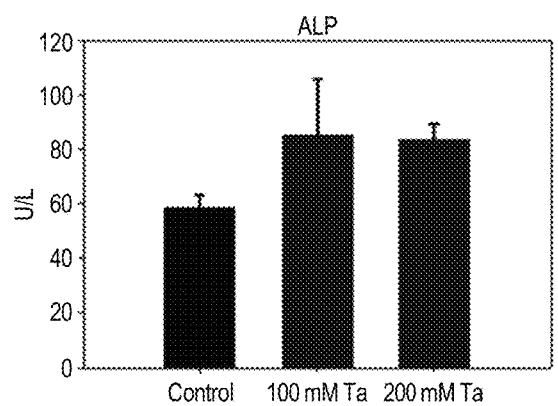
Figure 43E:
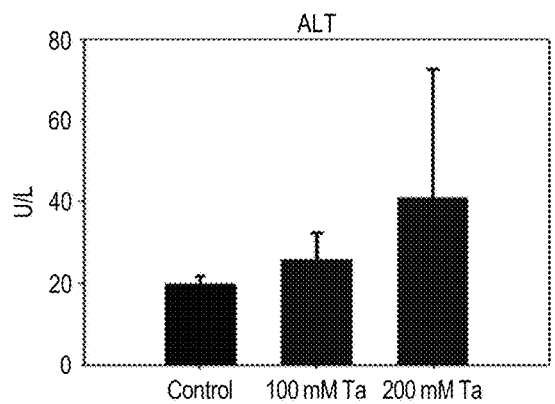
Figure 43F:
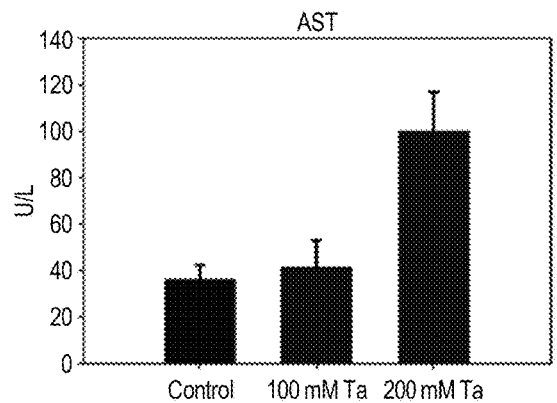

FIG. 42 shows histological changes in the heart, kidney, liver, spleen, and bladder of mice that received a single bolus dose of saline (control), 100 mM TaO$_x$ NC1 (220 μL, 296.2 mg kg$^{-1}$ in saline), and 200 mM TaO$_x$ NC1 (217 μL, 592.3 mg kg$^{-1}$ in saline) prepared in accordance with various aspects of the current technology, followed by dissection 72 hours post-injection. Sections were stained in hematoxylin and eosin (H&E) and observed under a light microscope at 20× magnification. Arrows point towards regions of renal infarct and necrosis in regions of liver and the spleen. The scale bar is 50 μm.

FIGS. 43A-43F shows detection results of liver and kidney function in terms of albumin, total bilirubin (TBIL), direct bilirubin (DBIL), alkaline phosphatase (ALP), alanine aminotransferase (ALT), and aspartate aminotransferase (AST) index for mice injected with saline (control group), 100 mM TaO$_x$ NC1, and 200 mM TaO$_x$ NC1 prepared in accordance with various aspects of the current technology.

Figure 44A:
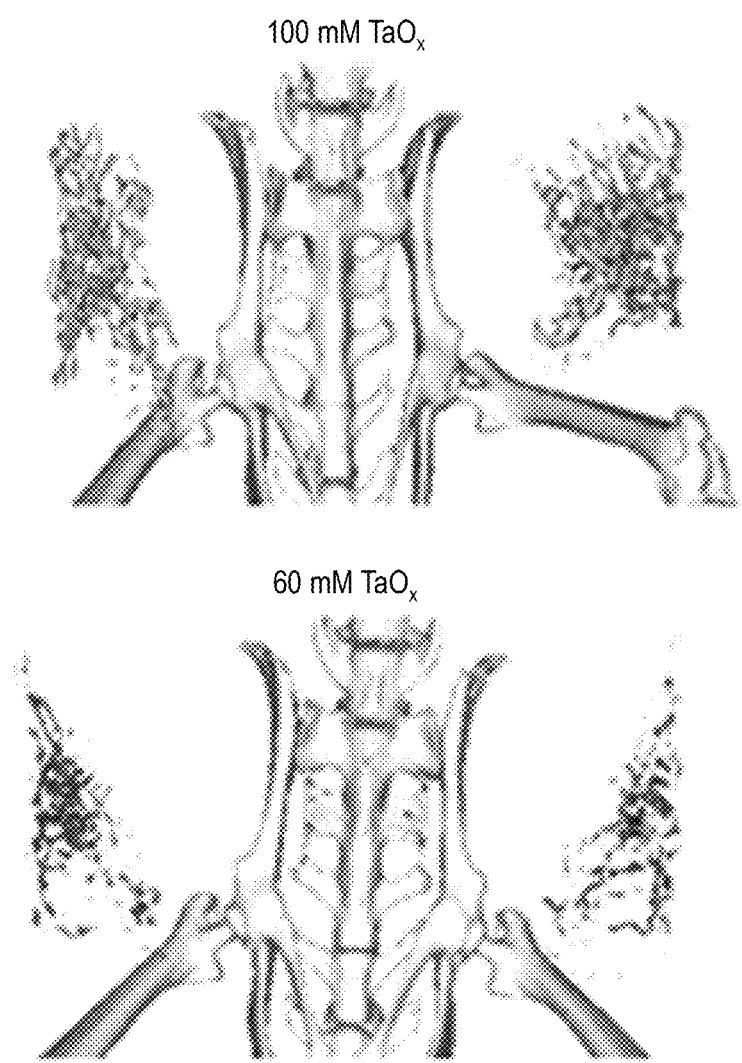
Figure 44B:
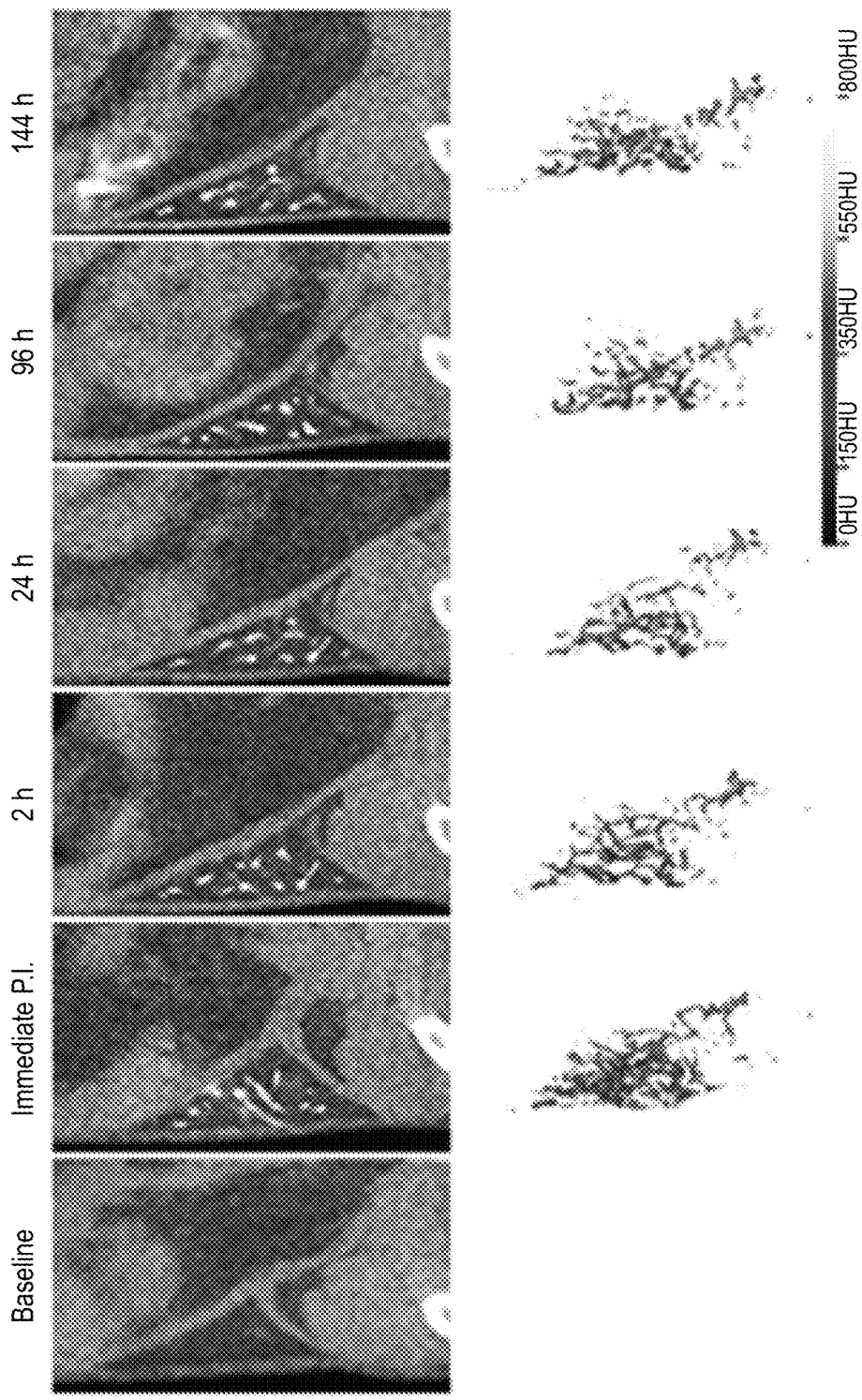

FIGS. 44A-44B show in vivo X-ray micro-CT imaging of mammary ductal tree in accordance with various aspects of the current technology. FIG. 44A shows three-dimensional reconstructions of ductal trees of an abdominal pair of mammary glands of independent 9 week-old FVB female mice immediately after intraductal administration of 40 mL per gland of 100 mM (upper panel) or 60 mM (lower panel) of TaO$_x$ NC1. FIG. 44B shows a ventral view (upper panel) and a three-dimensional reconstruction of the same representative FVB mouse at serial scan time points (baseline, immediate post-injection (immediate P.I.), and 2, 24, 96, and 144 hours post-injection) of a single intraductal administration of 40 μL of 60 mM TaO$_x$ NC1 (lower panel). HU histogram range is standardized from 0 HU to 800 HU. The color of the three-dimensional reconstruction of each injected ductal tree shows the average voxel intensity in HU of the rendered object.

Figure 45A:
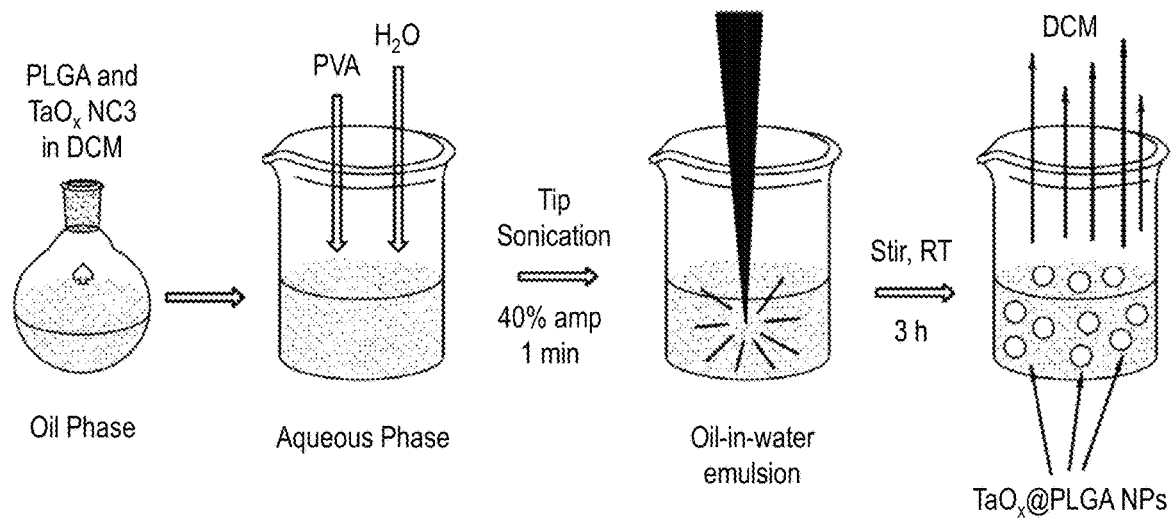
Figure 45B:
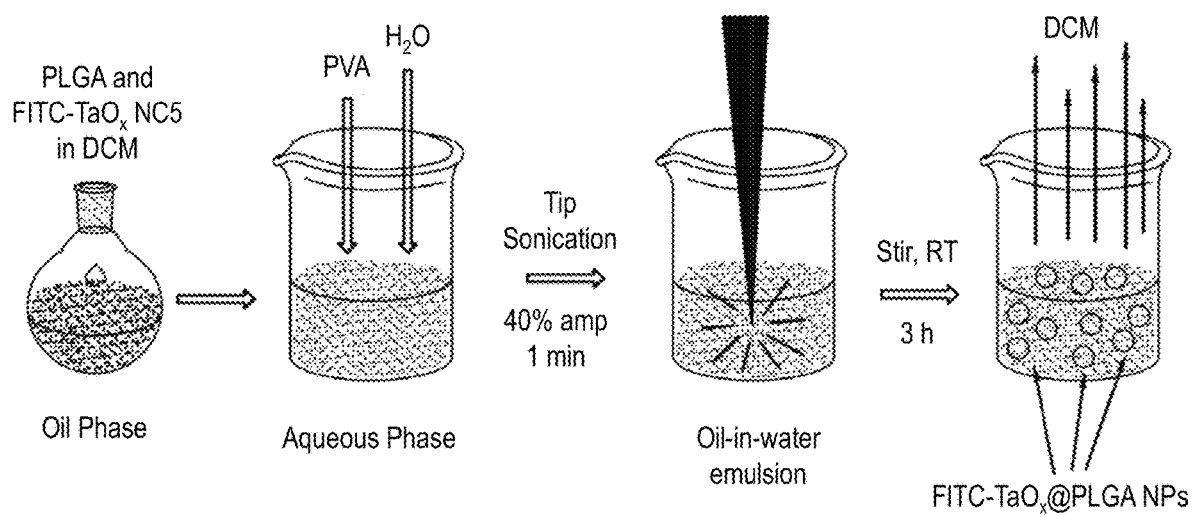

FIGS. 45A-45B are schematic representations for synthesis of TaO$_x$@PLGA NPs (FIG. 45A) and FITC-TaO$_x$@PLGA NPs (FIG. 45B) in accordance with various aspects of the current technology.

Figure 46A:
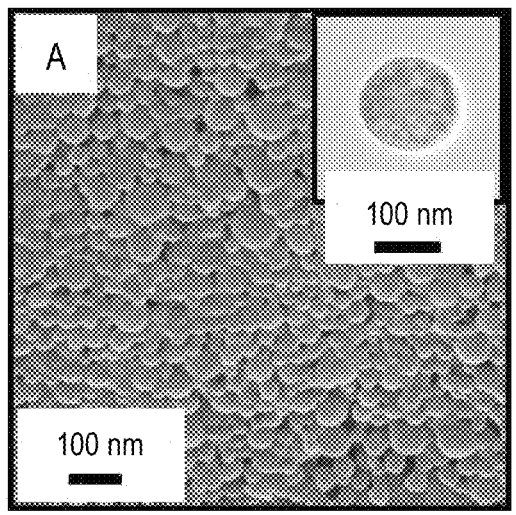
Figure 46B:
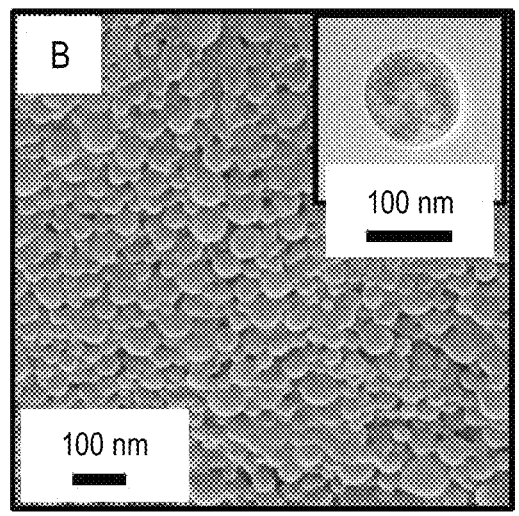
Figure 46C:
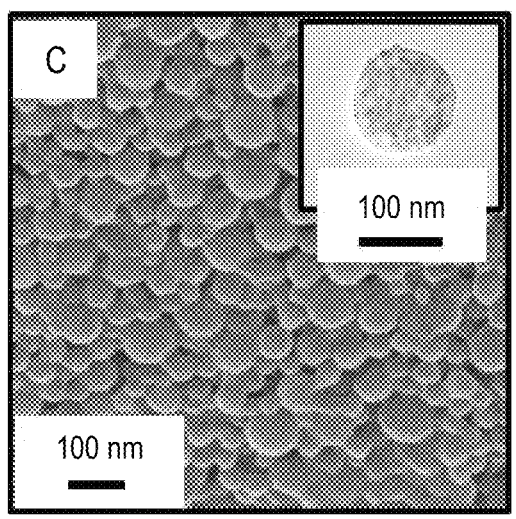
Figure 46D:
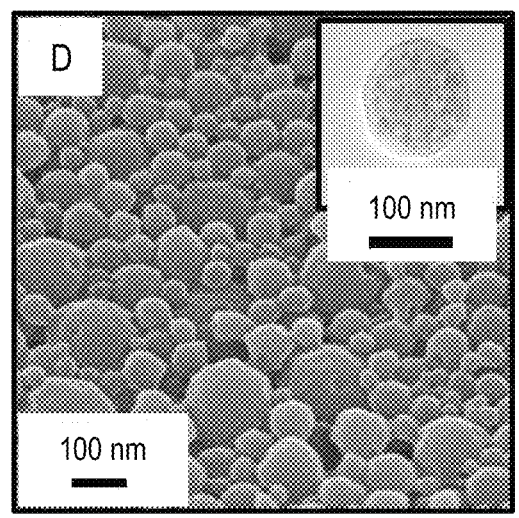

FIGS. 46A-46D are scanning electron microscopy (SEM) and TEM (inset) characterizations for TaO$_x$@PLGA NPs prepared in accordance with various aspects of the current technology (FIGS. 46A-46B) and FITC-TaO$_x$@PLGA NPs prepared in accordance with various aspects of the current technology (FIGS. 46C-46D).

Figure 47A:
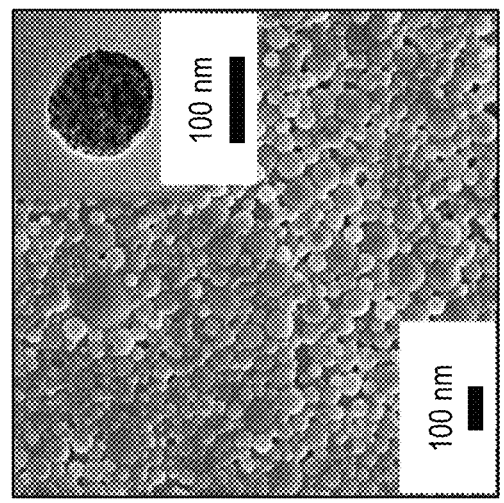
Figure 47B:
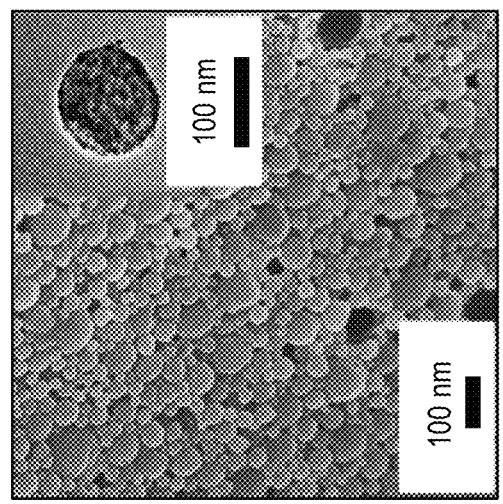
Figure 47C:
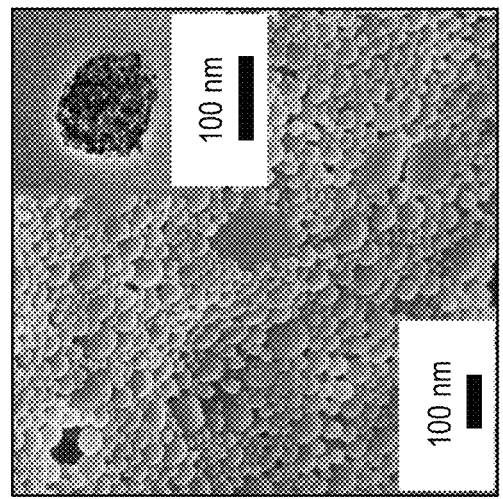

FIGS. 47A-47C are SEM and TEM (inset) images of TaO$_x$@PLGA NPs prepared in accordance with various aspects of the current technology. FIGS. 47A, 47B, and 47C respectively correspond to TaO$_x$@PLGA NPs obtained from three different batches that quite clearly show the homogeneity in size and the efficiency in packing of TaO$_x$ NC3 within the PLGA polymer.

Figure 48C:
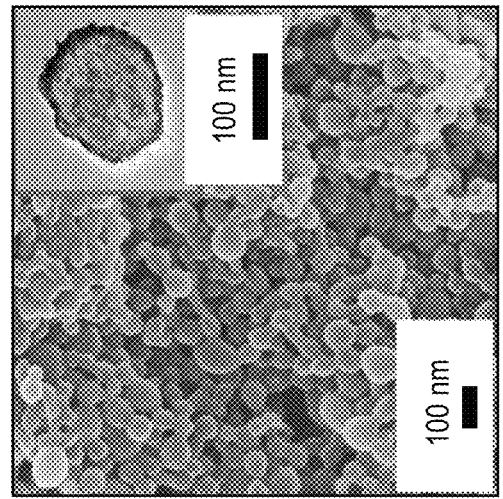
Figure 48B:
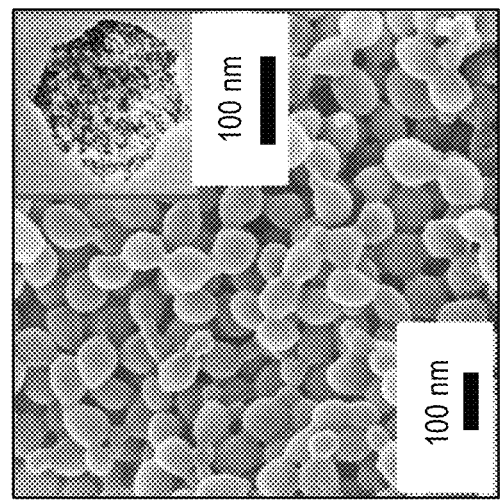
Figure 48A:
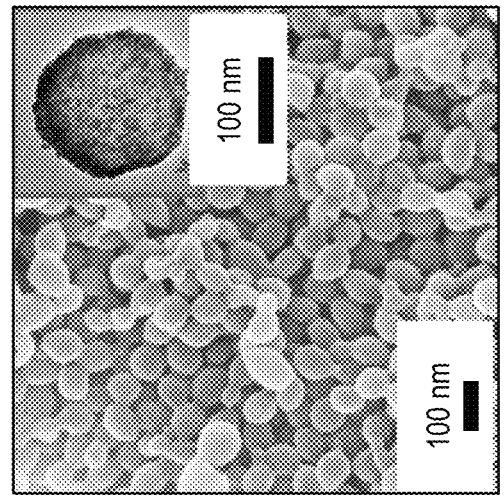
Figure 49B:
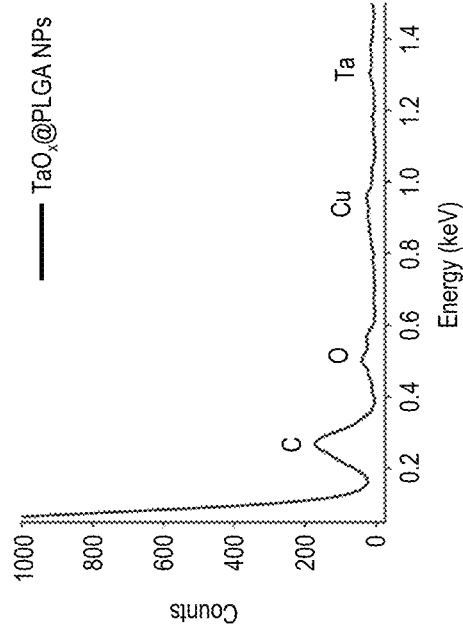
Figure 49A:
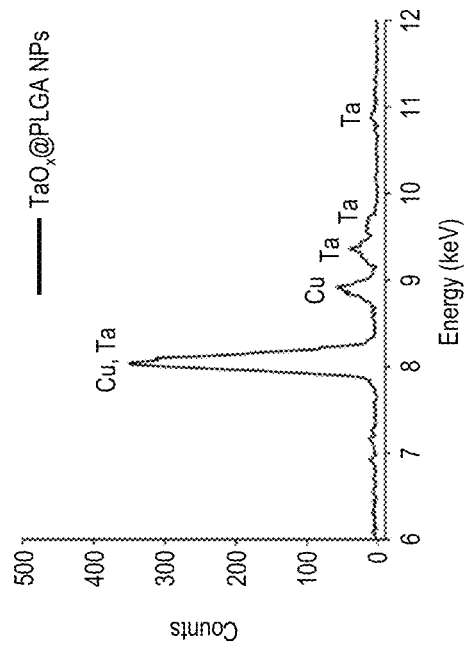
Figure 49D:
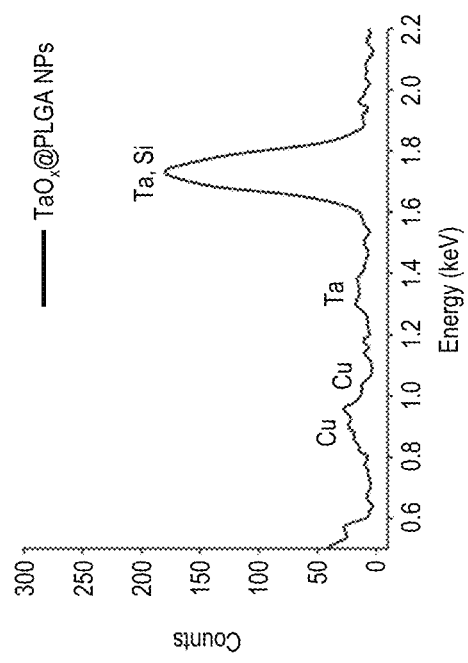
Figure 49C:
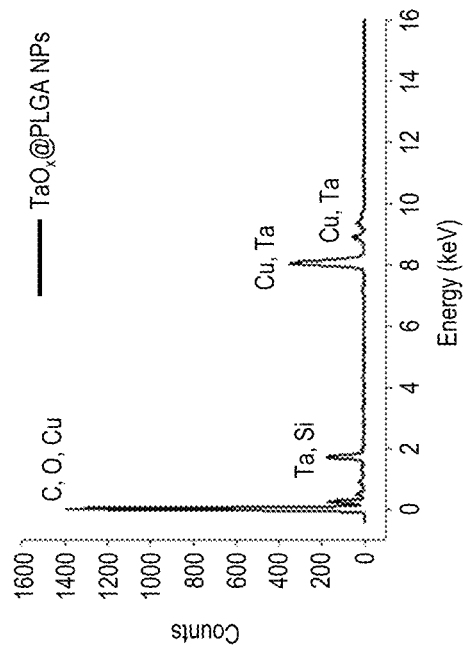
Figure 50B:
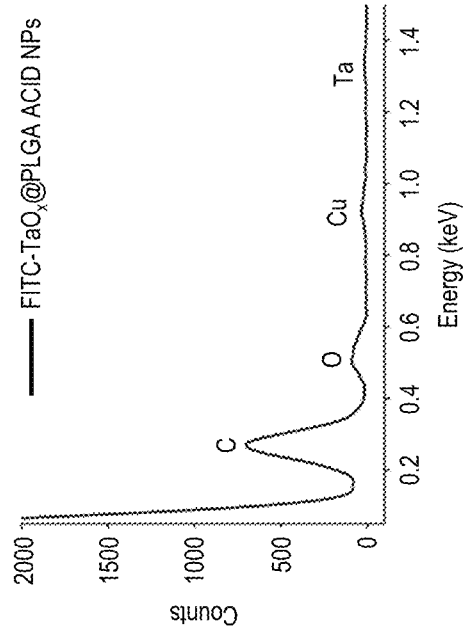
Figure 50D:
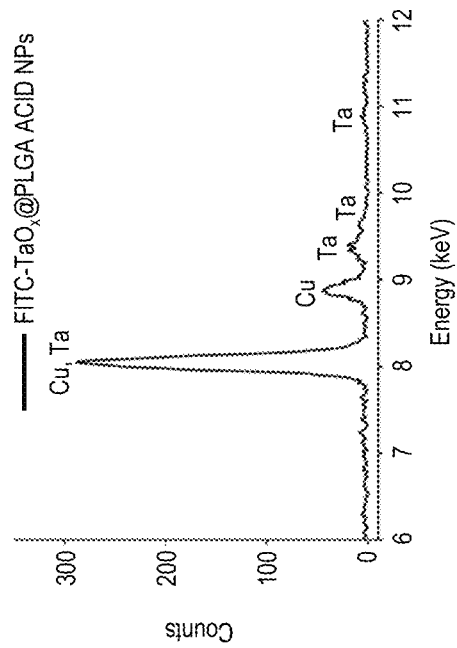
Figure 50A:
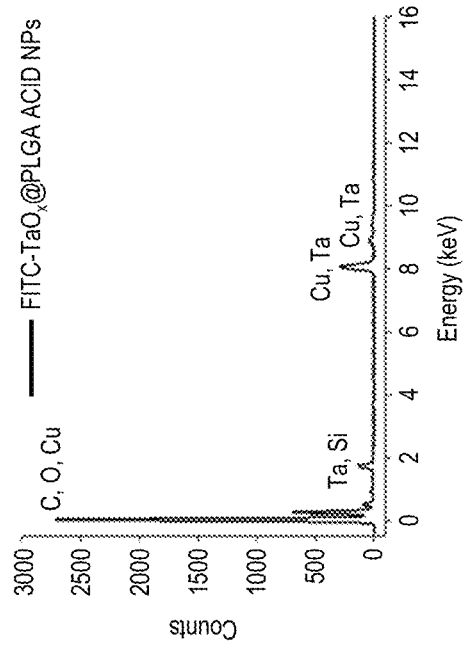
Figure 50C:
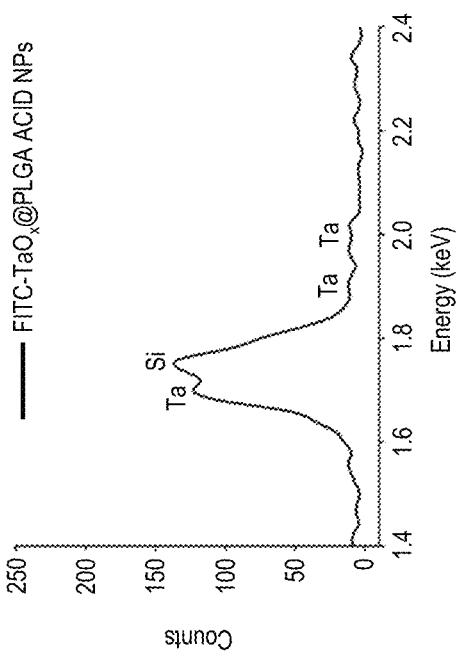

FIGS. 48A-48C are SEM and TEM (inset) images of FITC-TaO$_x$@PLGA NPs prepared in accordance with various aspects of the current technology. FIGS. 48A, 48B, and 48C respectively correspond to FITC-TaO$_x$@PLGA NPs obtained from three different batches that quite clearly show the homogeneity in size and the efficiency in packing of FITC-TaO$_x$ NC5 within the PLGA polymer.

FIGS. 49A-49D show EDS for TaO$_x$@PLGA NPs prepared in accordance with various aspects of the current technology, showing the presence of Ta and Si in the NCs. The peaks for C and Cu in the EDS spectra are attributed to the grid mesh used as a sample holder for TEM imaging.

FIGS. 50A-50D show EDS for FITC-TaO$_x$@PLGA NPs prepared in accordance with various aspects of the current technology, showing the presence of Ta and Si in the NCs. The peaks for C and Cu in the EDS spectra are attributed to the grid mesh used as a sample holder for TEM imaging.

Figure 51:
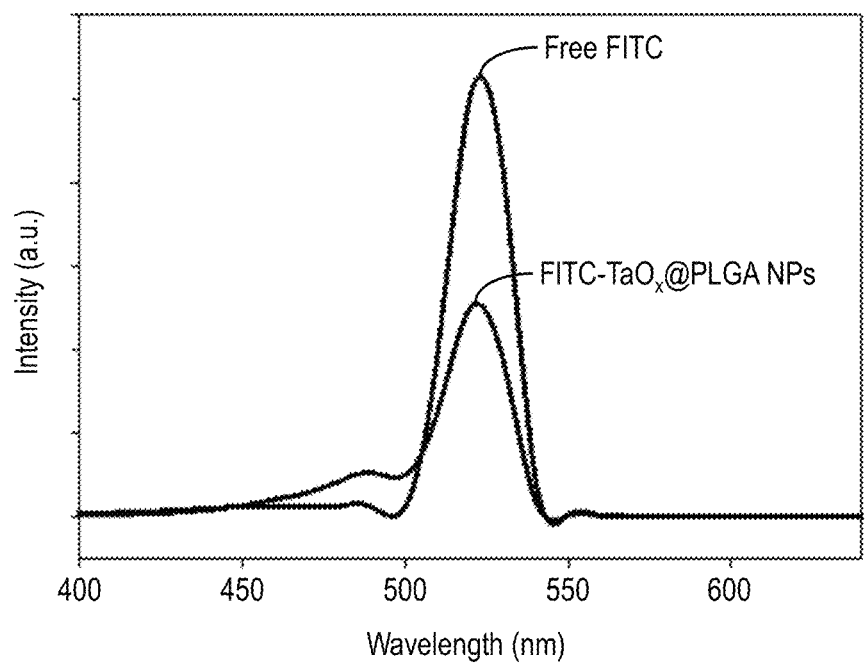

FIG. 51 shows a fluorescence spectral comparison for free FITC and the FITC-TaO$_x$@PLGA NPs in PBS prepared in accordance with various aspects of the current technology.

Figure 52A:
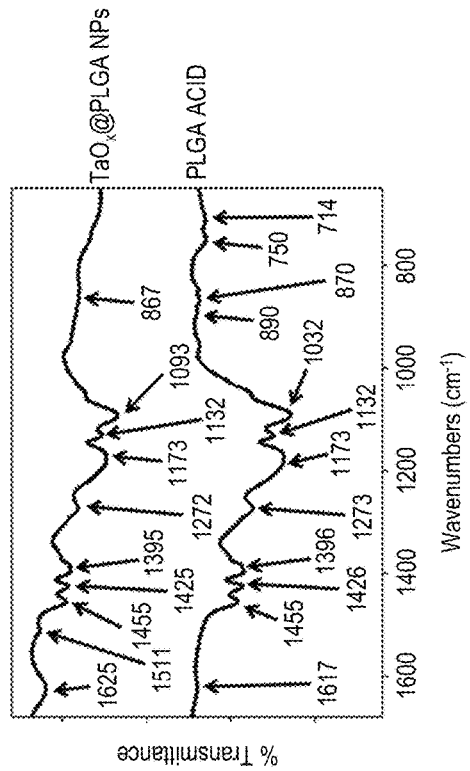
Figure 52B:
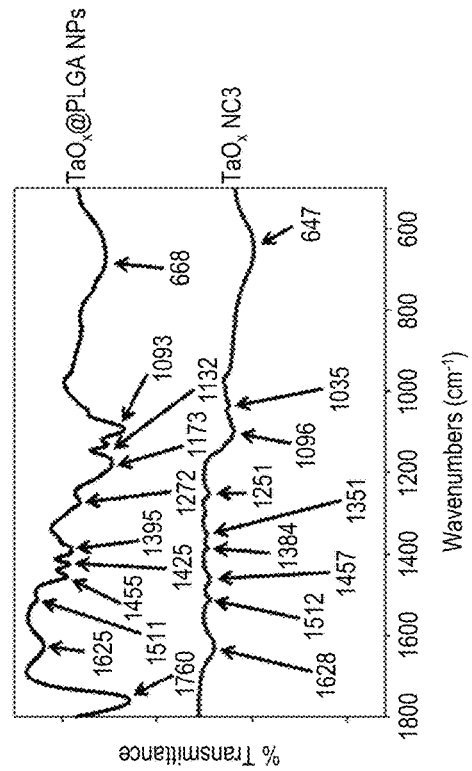
Figure 52C:
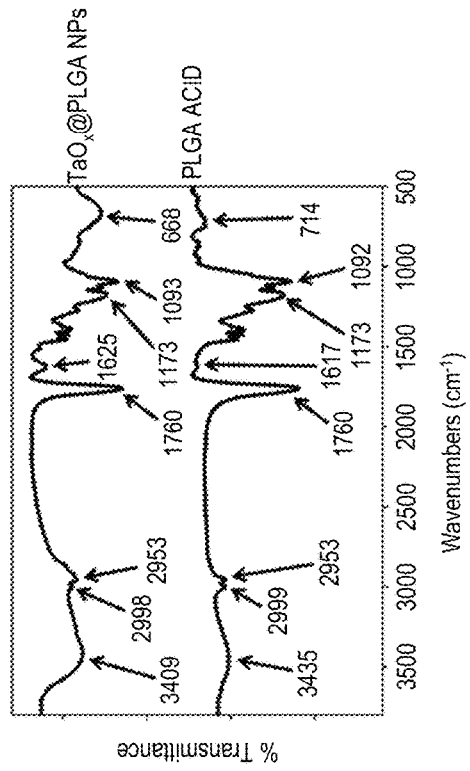
Figure 52D:
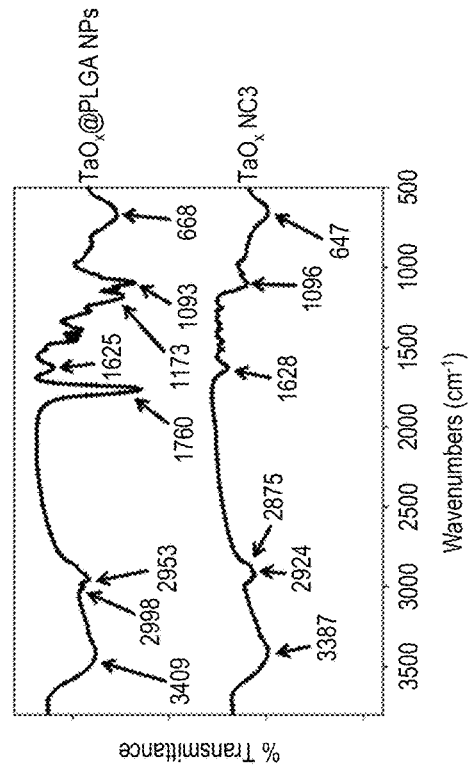

FIGS. 52A-52D show FTIR spectra comparing the as-synthesized TaO$_x$@PLGA NPs prepared in accordance with various aspects of the current technology with the starting materials, PLGA ACID (FIGS. 52A-52B) and TaO$_x$ NC3 (FIGS. 52C-52D). Prominent and common transmittance peaks are pointed out.

Figure 53A:
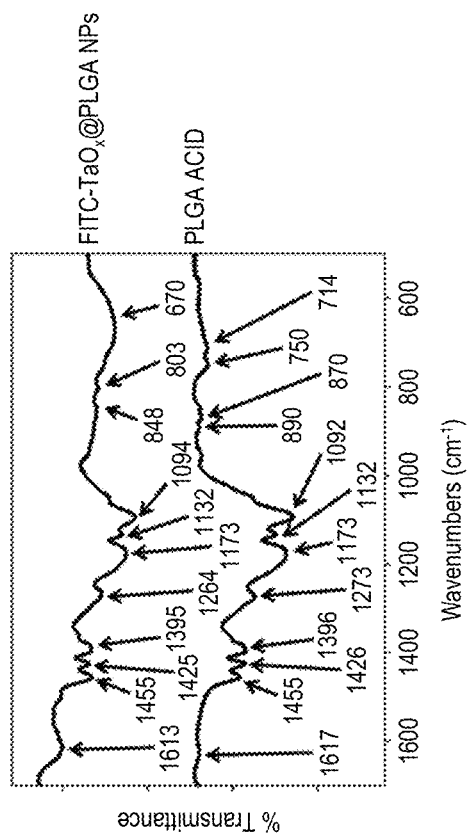
Figure 53B:
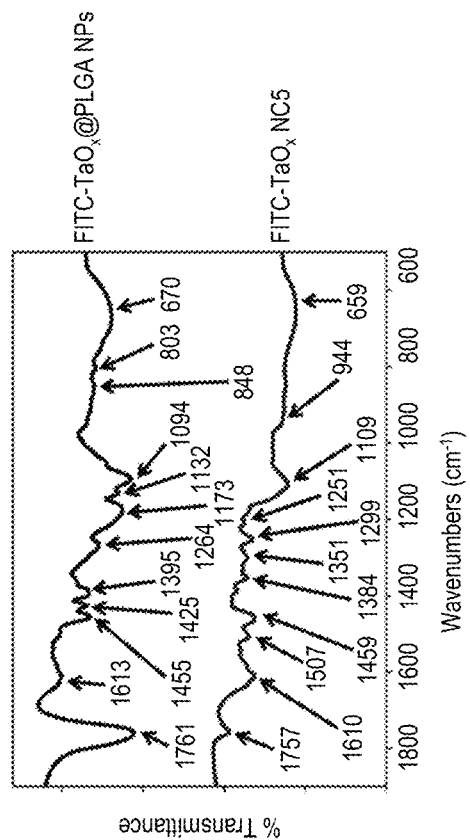
Figure 53C:
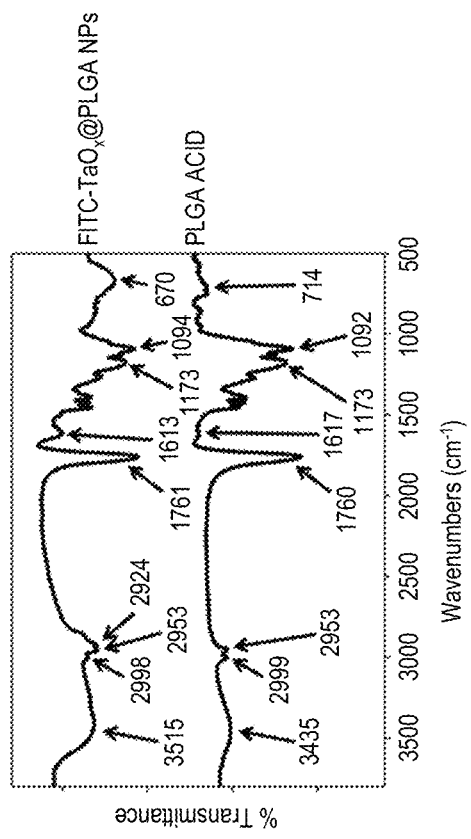
Figure 53D:
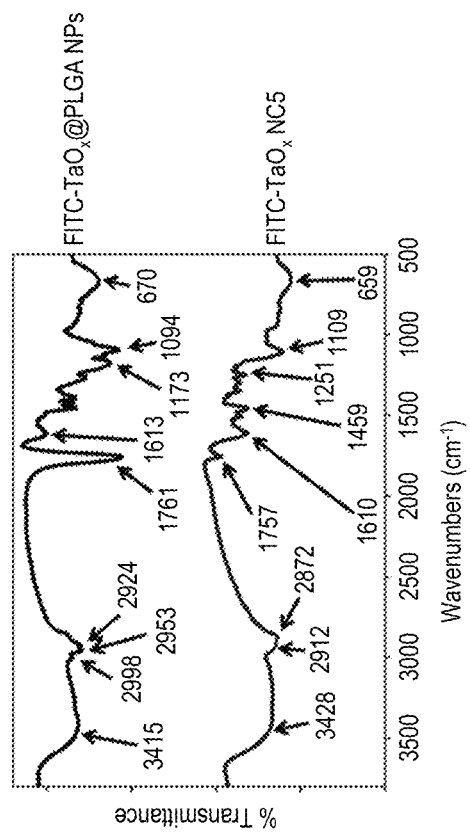

FIGS. 53A-53D show FTIR spectra comparing the as-synthesized FITC-TaO$_x$@PLGA NPs prepared in accordance with various aspects of the current technology with the starting PLGA ACID (FIGS. 53A-53B) and FITC-TaO$_x$ NC5 (FIGS. 53C-53D). Prominent and common transmittance peaks are pointed out.

FIG. 54 is a schematic representation for the synthesis of various TaO$_x$-embedded mesoporous silica nanoparticles (MSNPs) prepared in accordance with various aspects of the current technology.

Figure 55:
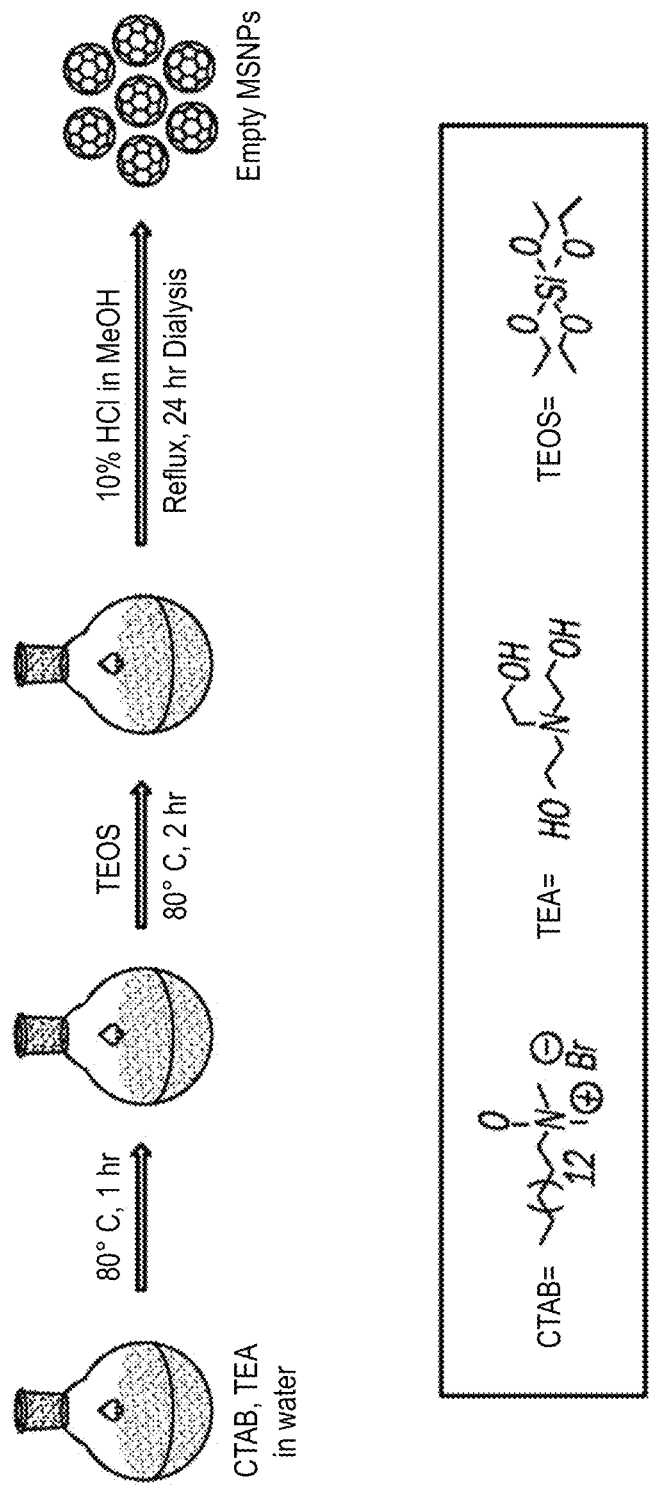

FIG. 55 is a schematic representation for the synthesis of empty MSNPs in accordance with various aspects of the current technology.

Figure 56:
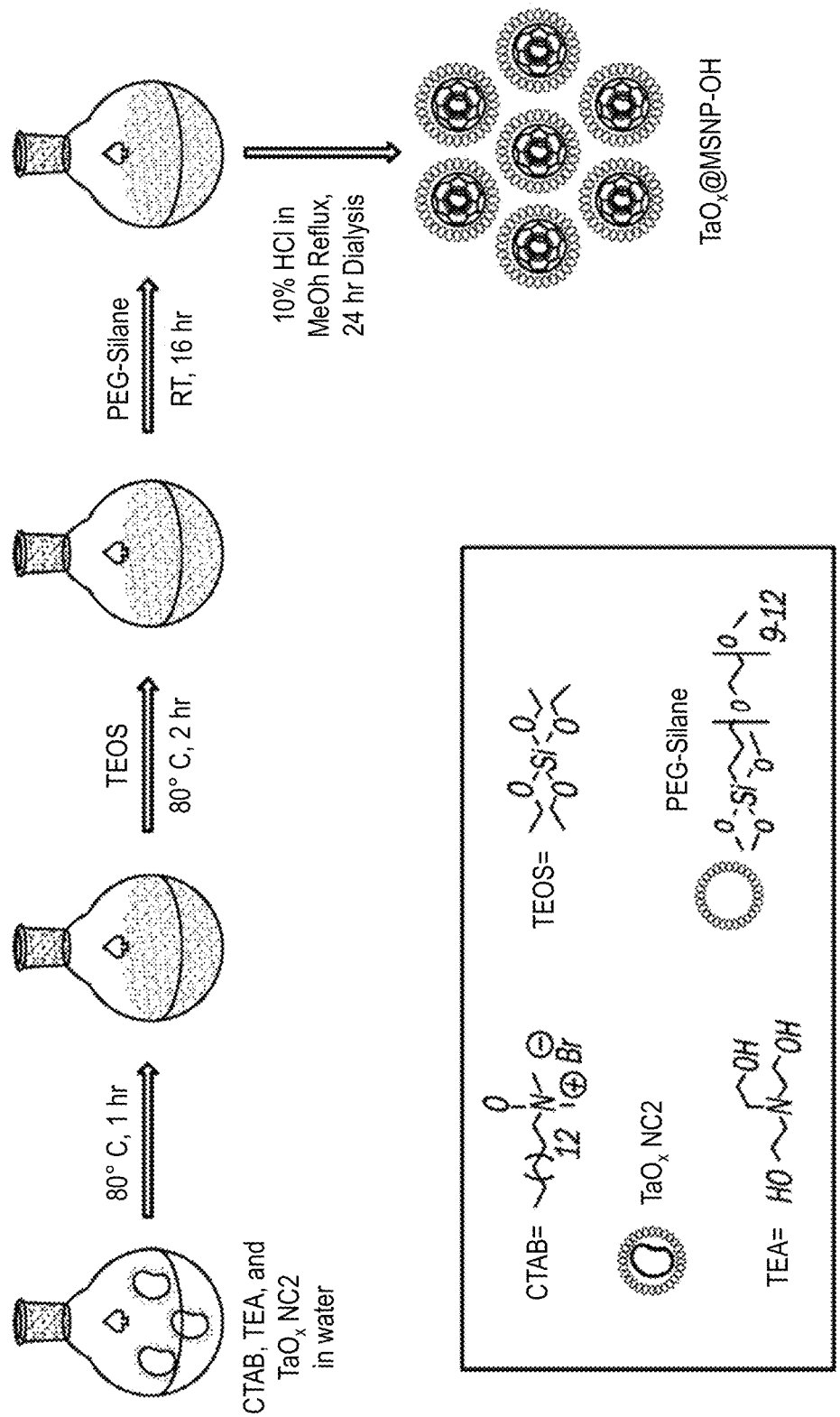

FIG. 56 is a schematic representation for the synthesis of MSNPs embedded with $TaO_x$ NC2 ($TaO_x$-MSNP-OH) in accordance with various aspects of the current technology.

Figure 57:
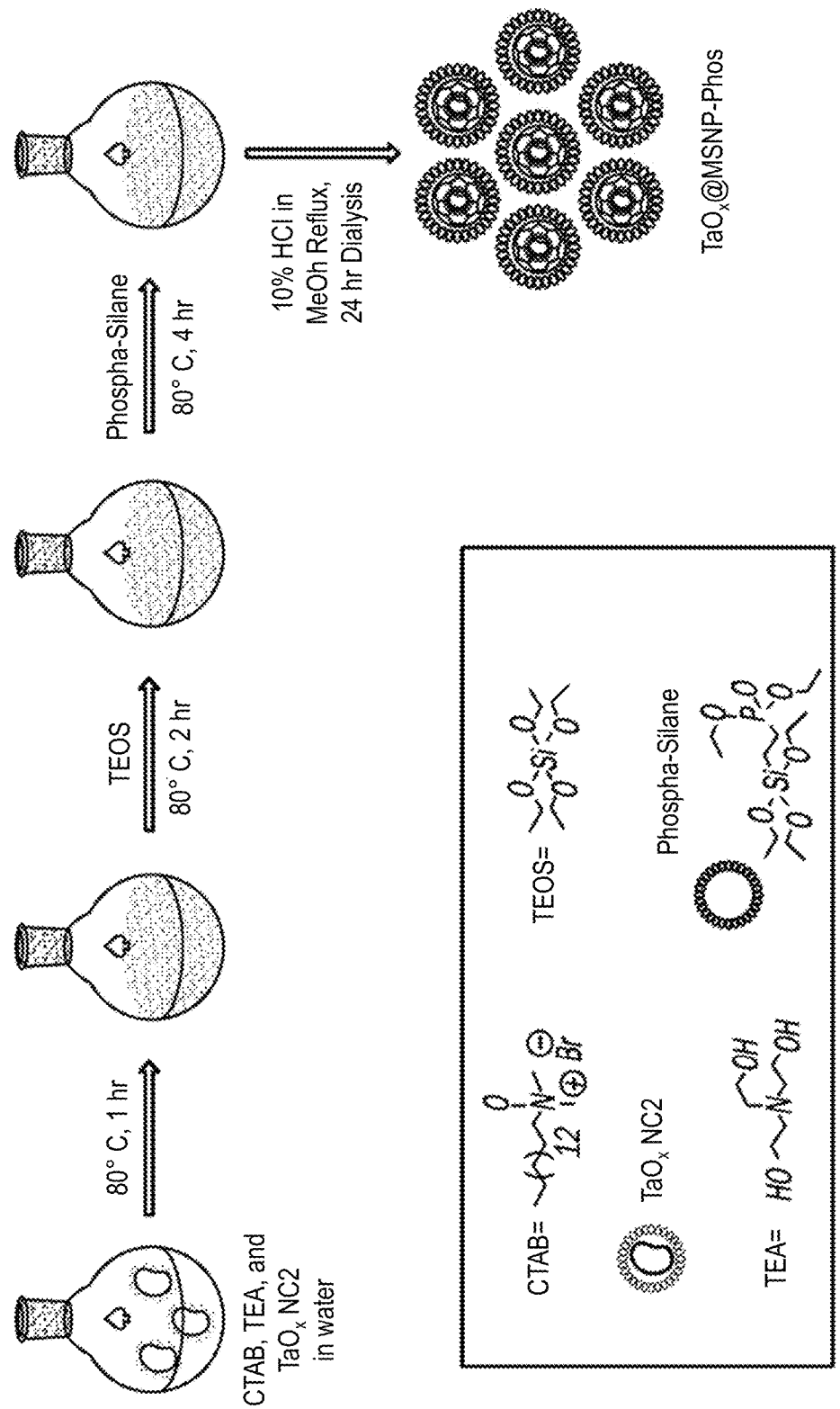

FIG. 57 is a schematic representation for the synthesis of MSNPs embedded with $TaO_x$ NC2 ($TaO_x$@MSNP-Phos) in accordance with various aspects of the current technology.

Figure 58:
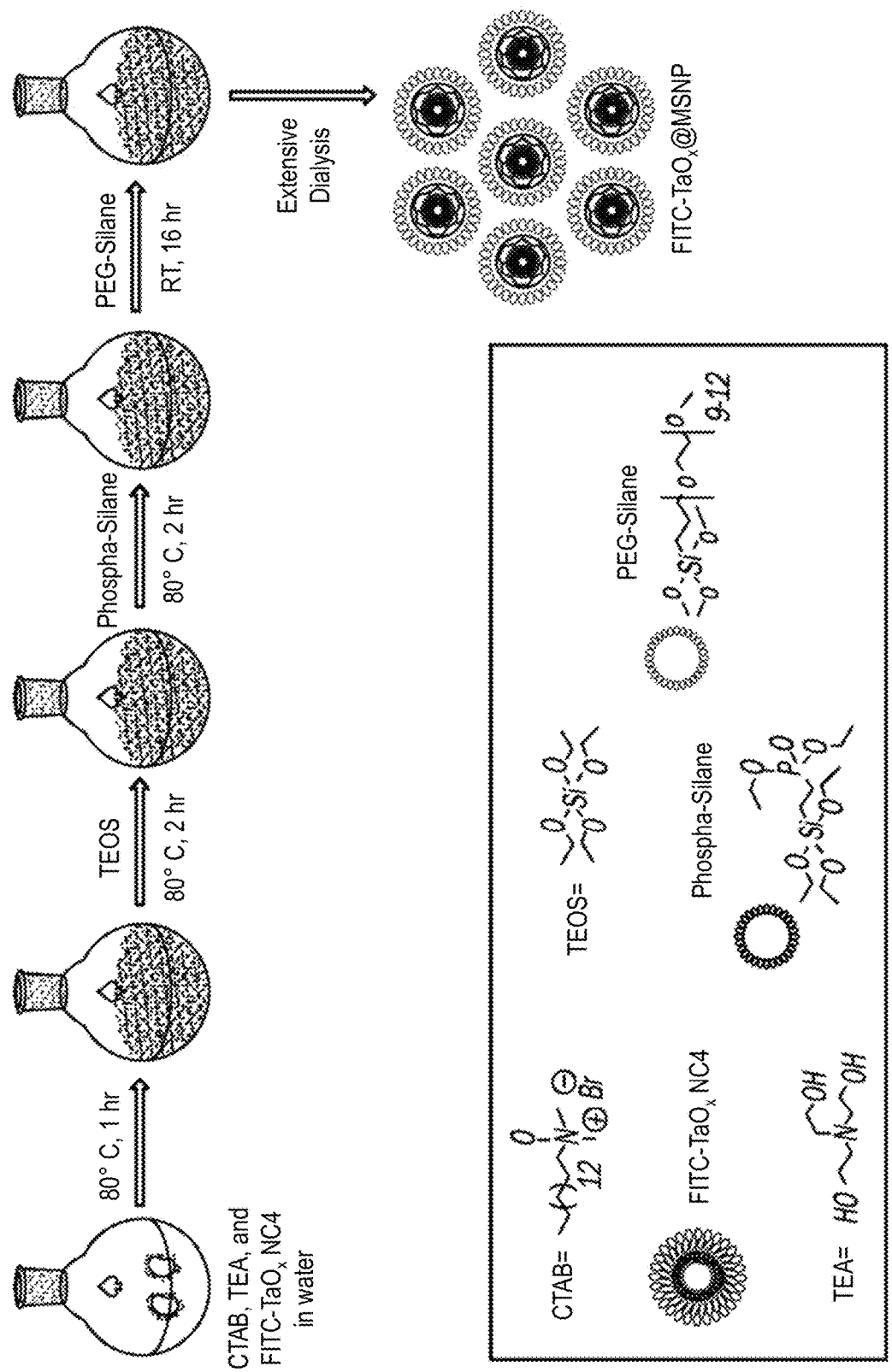

FIG. 58 is a schematic representation for the synthesis of MSNPs embedded with FTIC-$TaO_x$ NC4 (FITC-$TaO_x$@MSNP) in accordance with various aspects of the current technology.

Figure 59C:
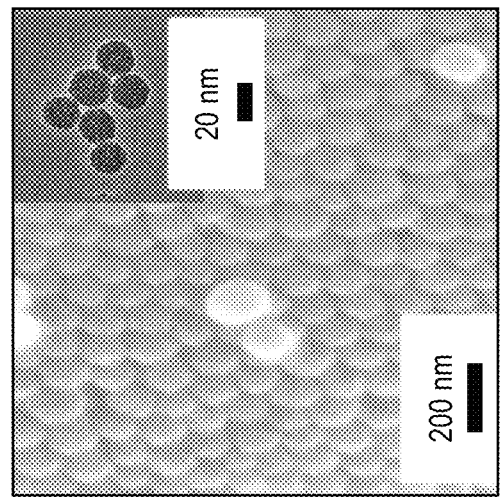
Figure 59B:
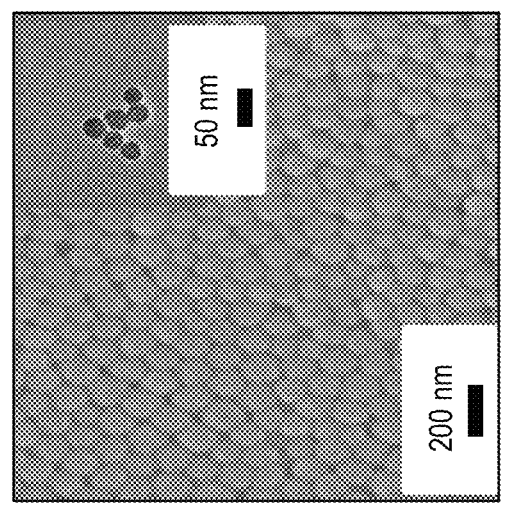
Figure 59A:
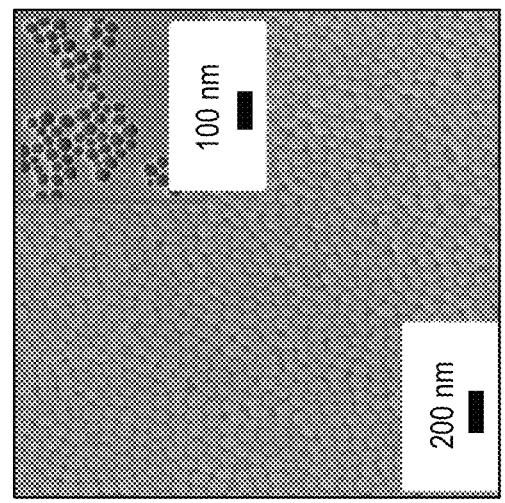

FIGS. 59A-59C are SEM and TEM (inset) images of empty MSNPs. FIGS. 59A, 59B, and 59C respectively correspond to MSNPs obtained from three different batches that quite clearly show the homogeneity in size.

Figure 60A:
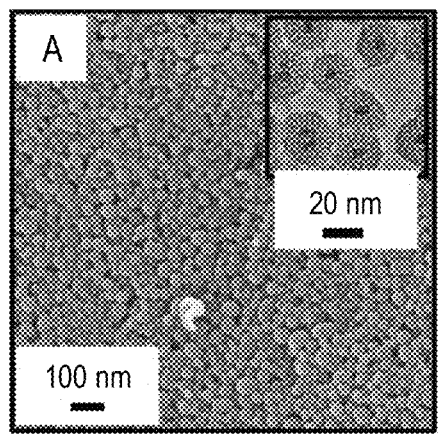
Figure 60B:
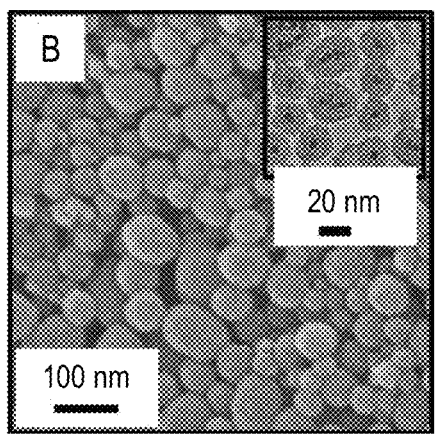
Figure 60C:
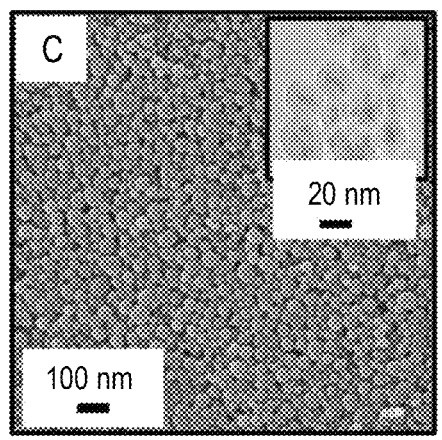
Figure 60D:
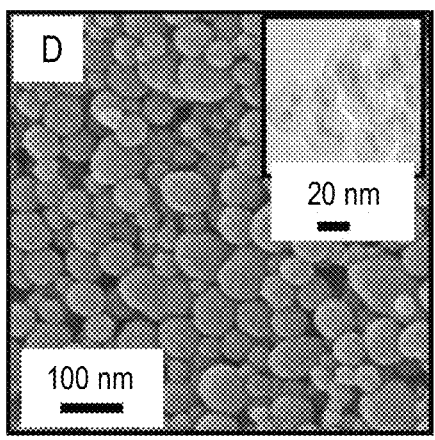
Figure 60E:
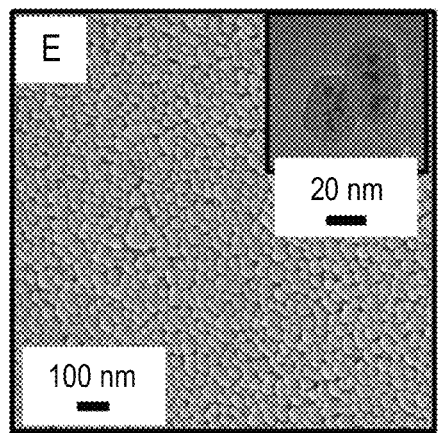
Figure 60F:
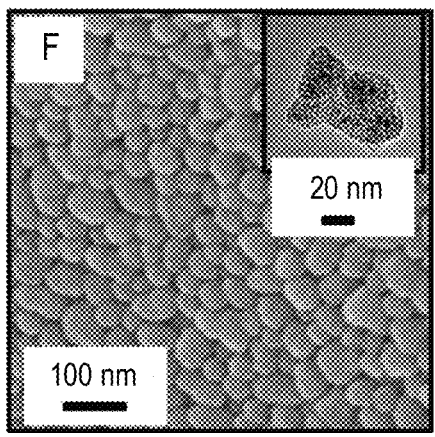

FIGS. 60A-60F are SEM and TEM (inset) characterizations for $TaO_x$@MSNP-OH prepared in accordance with various aspects of the current technology (FIGS. 60A-60B); $TaO_x$@MSNP-Phos prepared in accordance with various aspects of the current technology (FIGS. 60C-60D); and FITC-$TaO_x$@MSNP prepared in accordance with various aspects of the current technology (FIGS. 60E-60F).

Figure 61C:
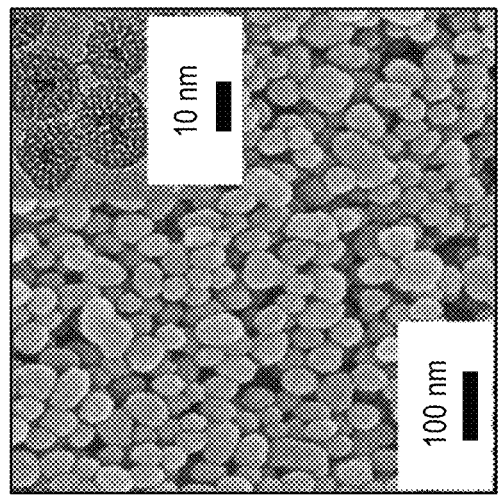
Figure 61B:
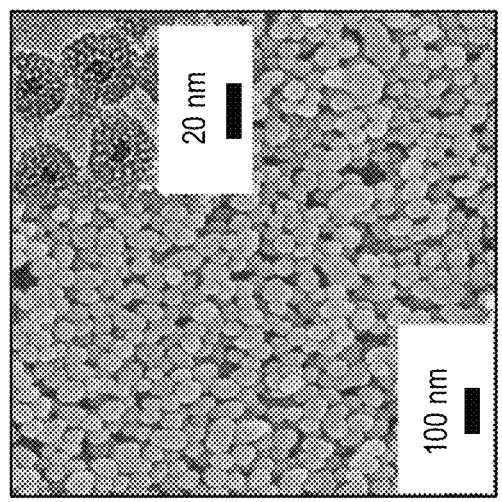
Figure 61A:
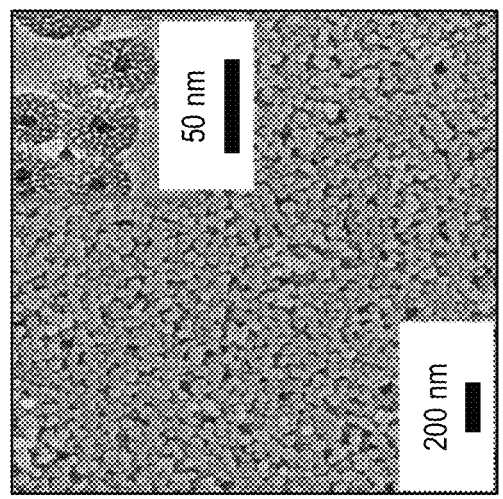

FIGS. 61A-61C are SEM and TEM (inset) images of $TaO_x$@MSNP-OH NPs prepared in accordance with various aspects of the current technology. FIGS. 61A, 61B, and 61C respectively correspond to $TaO_x$@MSNP-OH NPs obtained from three different batches that quite clearly show the homogeneity in size and the efficiency in packing of $TaO_x$ NC2 within the mesoporous silica shell.

Figure 62C:
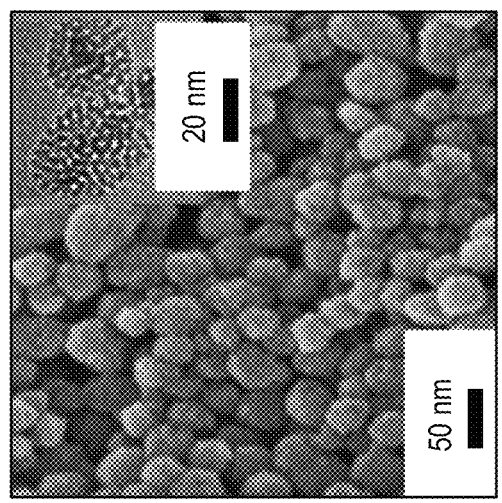
Figure 62B:
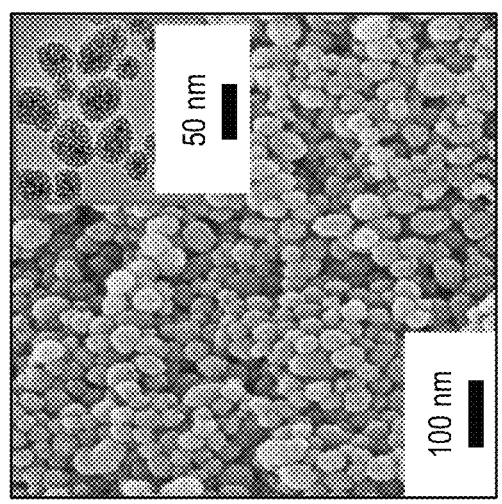
Figure 62A:
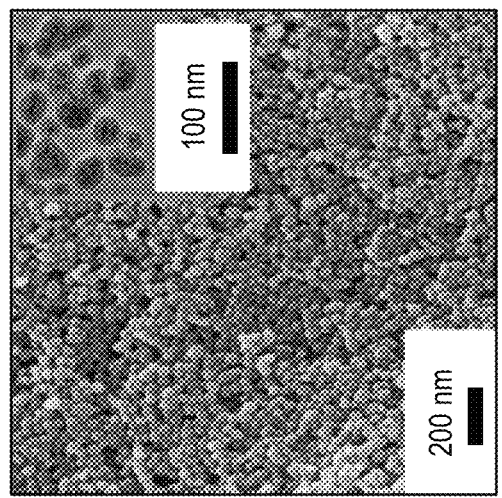

FIGS. 62A-62C are SEM and TEM (inset) images of $TaO_x$@MSNP-Phos NPs prepared in accordance with various aspects of the current technology. FIG. 62A, FIG. 62B, and FIG. 62C respectively correspond to $TaO_x$@MSNP-Phos NPs obtained from three different batches that quite clearly show the homogeneity in size and the efficiency in packing of $TaO_x$ NC2 within the mesoporous silica shell.

FIGS. 63A-63C are SEM and TEM (inset) images of FITC-$TaO_x$@MSNPs prepared in accordance with various aspects of the current technology. FIGS. 63A, 63B, and 63C respectively correspond to FITC-$TaO_x$@MSNPs obtained from three different batches that quite clearly show the homogeneity in size and the efficiency in packing of FITC-$TaO_x$ NC4 within the mesoporous silica shell.

Figure 64A:
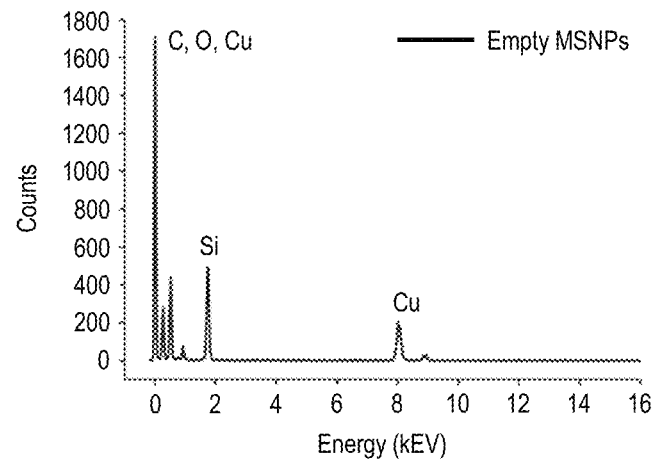
Figure 64B:
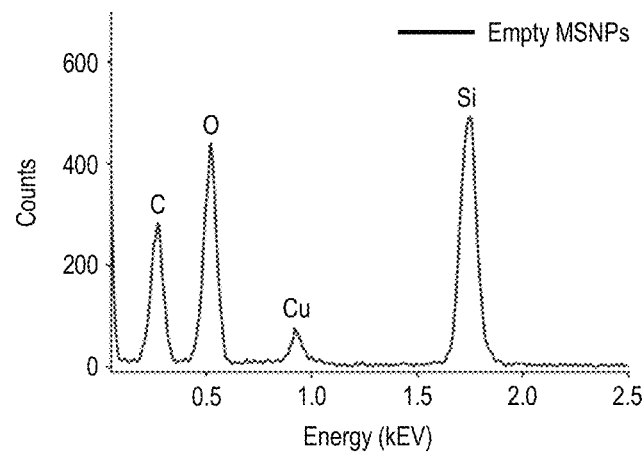
Figure 65B:
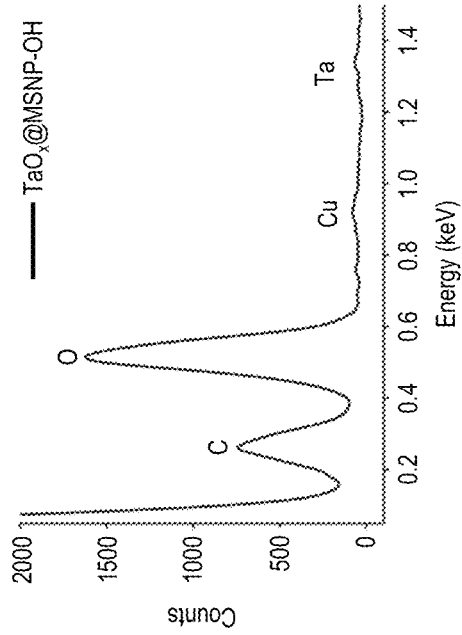
Figure 65D:
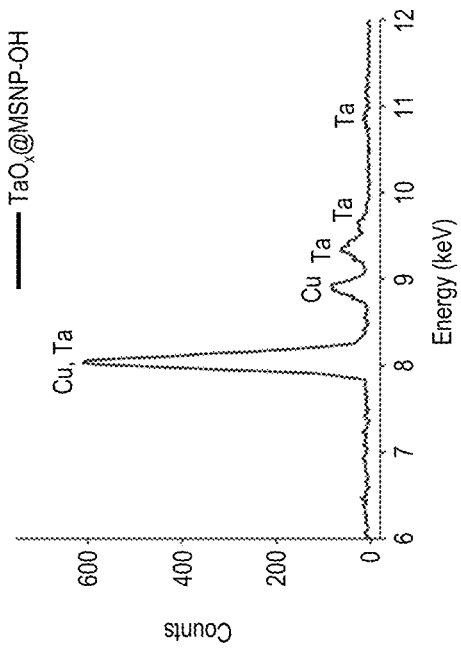
Figure 65A:
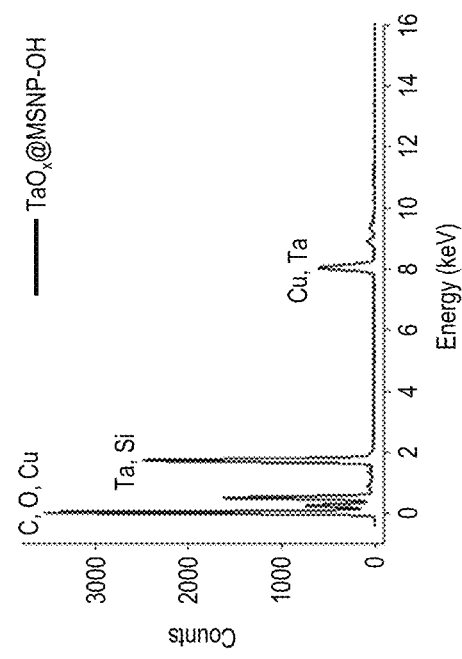
Figure 65C:
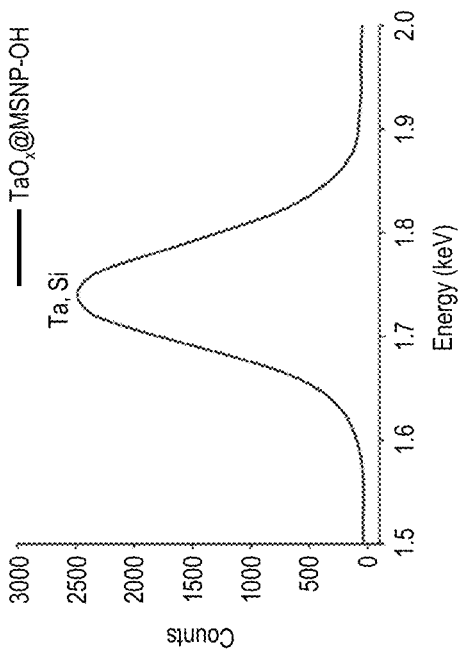
Figure 67B:
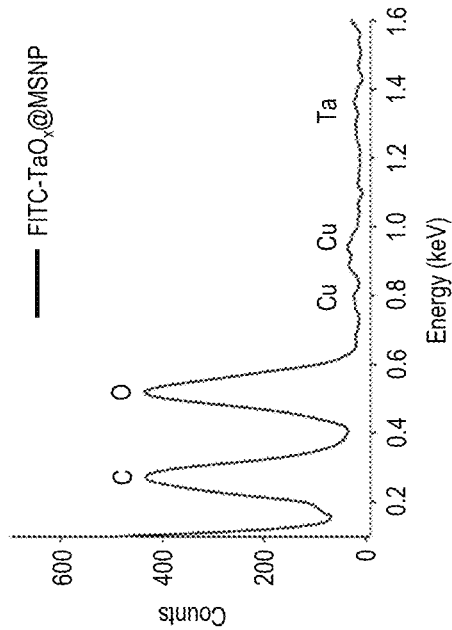
Figure 67D:
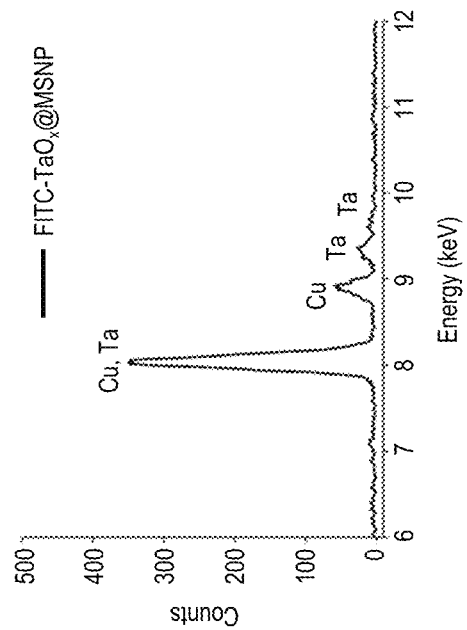
Figure 67A:
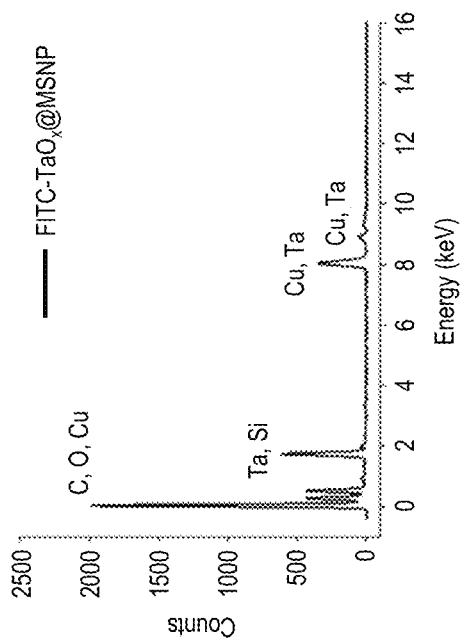
Figure 67C:
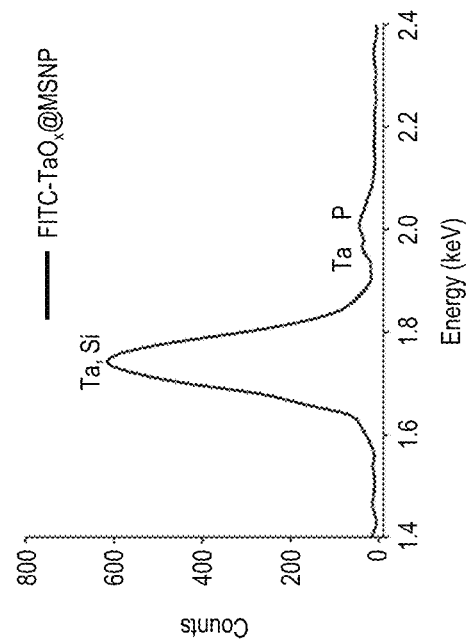

FIGS. 64A-64B show EDS for empty MSNPs prepared in accordance with various aspects of the current technology, showing the presence of Si in the NCs. The peaks for C and Cu in the EDS spectra are attributed to the grid mesh used as a sample holder for TEM imaging.

FIGS. 65A-65D show EDS for $TaO_x$@MSNP-OH NPs prepared in accordance with various aspects of the current technology, showing the presence of Ta and Si in the NCs. The peaks for C and Cu in the EDS spectra are attributed to the grid mesh used as a sample holder for TEM imaging.

FIGS. 66A-66C show EDS for $TaO_x$@MSNP-Phos NPs prepared in accordance with various aspects of the current technology, showing the presence of Ta, P, and Si in the NCs. The peaks for C and Cu in the EDS spectra are attributed to the grid mesh used as a sample holder for TEM imaging.

FIGS. 67A-67D show EDS for FITC-$TaO_x$@MSNPs, showing the presence of Ta, P, and Si in the NCs. The peaks for C and Cu in the EDS spectra are attributed to the grid mesh used as a sample holder for TEM imaging.

Figure 68:
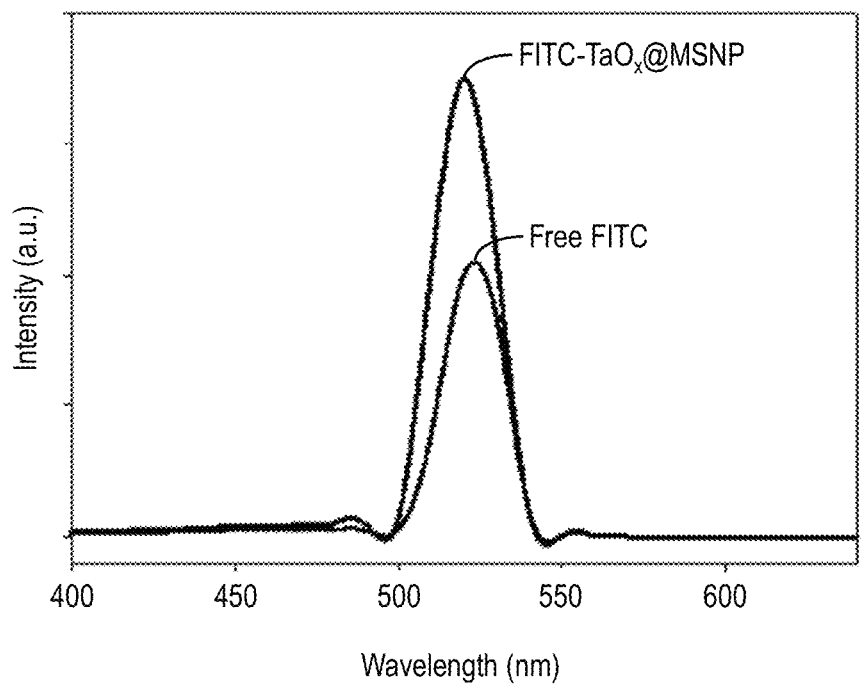

FIG. 68 shows a fluorescence spectral comparison for free FITC and FITC-$TaO_x$@MSNP prepared in accordance with various aspects of the current technology in PBS.

Figure 69:
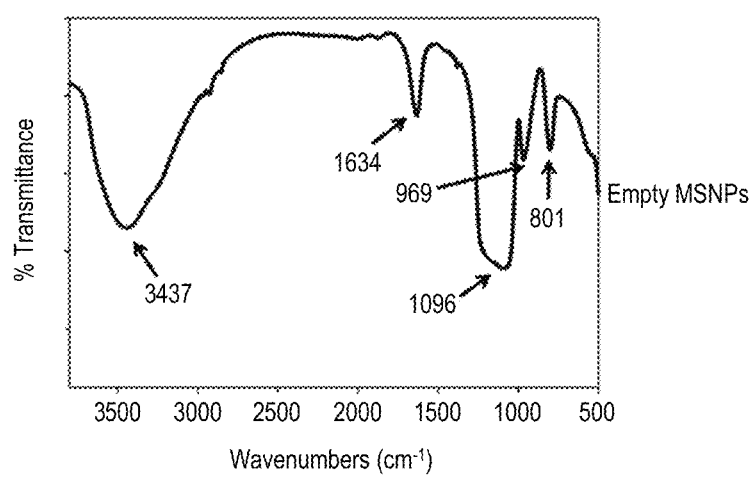

FIG. 69 is a FTIR spectra of the as-synthesized empty MSNPs prepared in accordance with various aspects of the current technology. MSNPs are characterized by long and branched siloxane chains as a result of which the Si—O—Si absorption band around 1200-1000 cm$^{-1}$ becomes broader and more complex. The broad band centered at 1096 cm$^{-1}$ is characteristic of MSNPs. Prominent and common transmittance peaks are pointed out.

FIGS. 70A-70D show FTIR spectra comparing the as-synthesized $TaO_x$@MSNP-OH NPs prepared in accordance with various aspects of the current technology and the starting material $TaO_x$ NC2 (FIGS. 70A-70B). The consequent comparison with PEG-Silane and empty MSNPs with the as-synthesized $TaO_x$@MSNP-OH NPs is shown in FIGS. 70C-70D. Prominent and common transmittance peaks are pointed out.

Figure 71A:
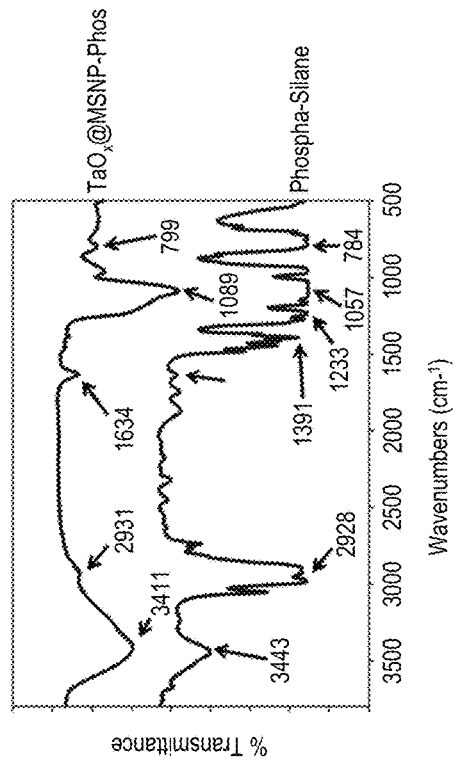
Figure 71B:
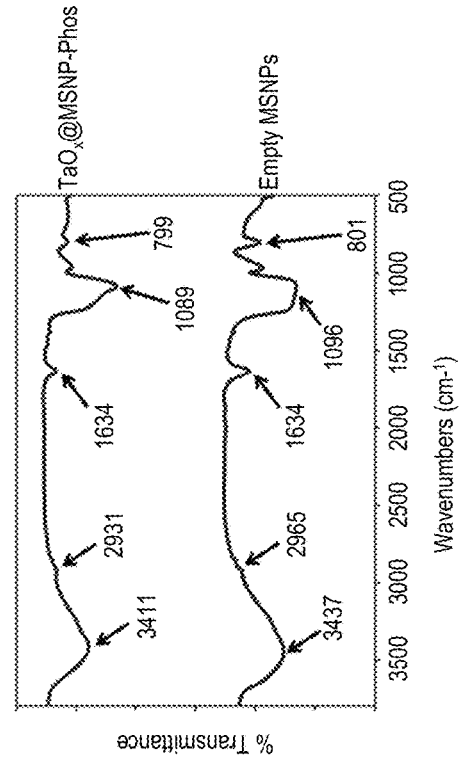
Figure 71C:
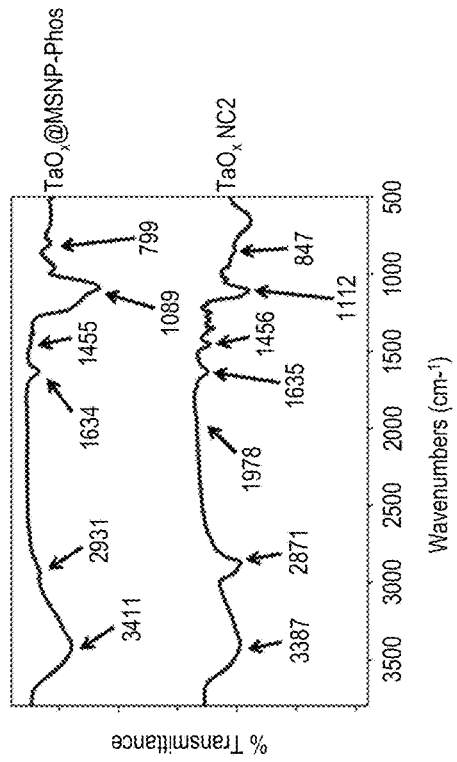
Figure 71D:
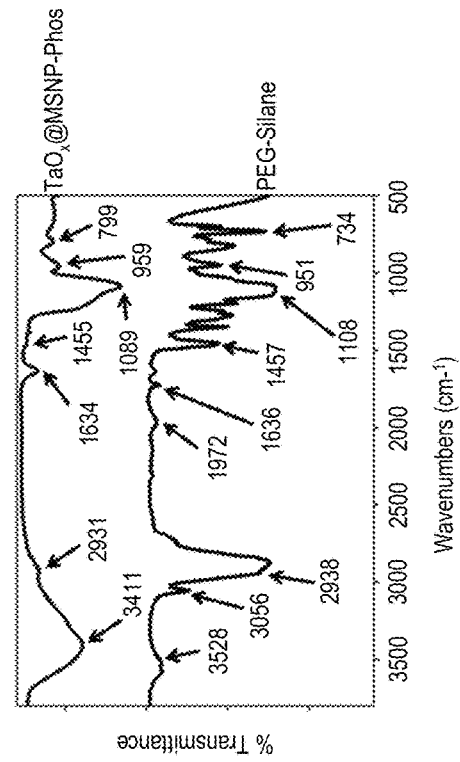

FIGS. 71A-71D show FTIR spectra comparing the as-synthesized $TaO_x$@MSNP-Phos NPs prepared in accordance with various aspects of the current technology and the starting material $TaO_x$ NC2 and Phospha-Silane (FIGS. 71A-71B). The consequent comparison with PEG-Silane and empty MSNPs with the as-synthesized $TaO_x$@MSNP-Phos NPs is shown in FIGS. 71C-71D. Prominent and common transmittance peaks are pointed out.

Figure 72A:
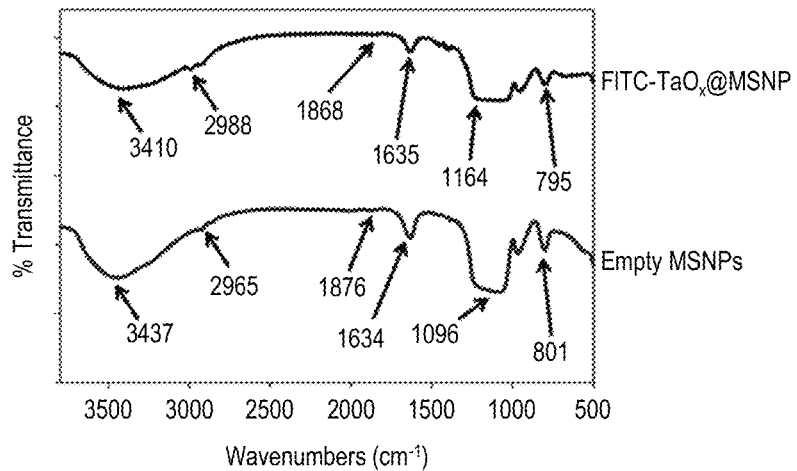
Figure 72B:
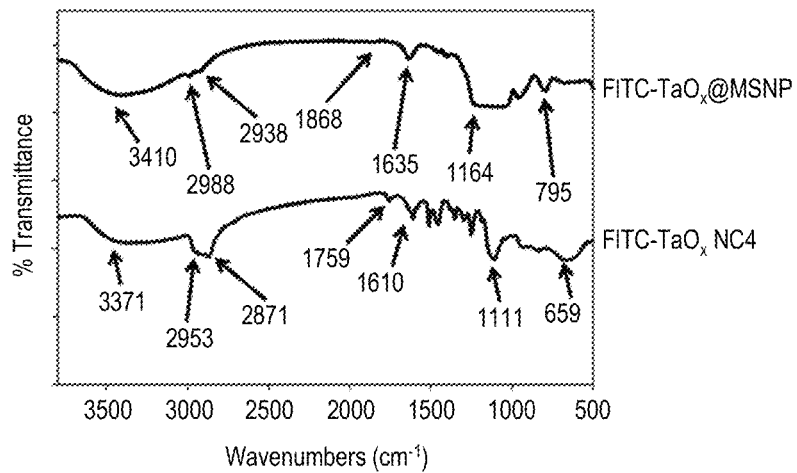
Figure 72C:
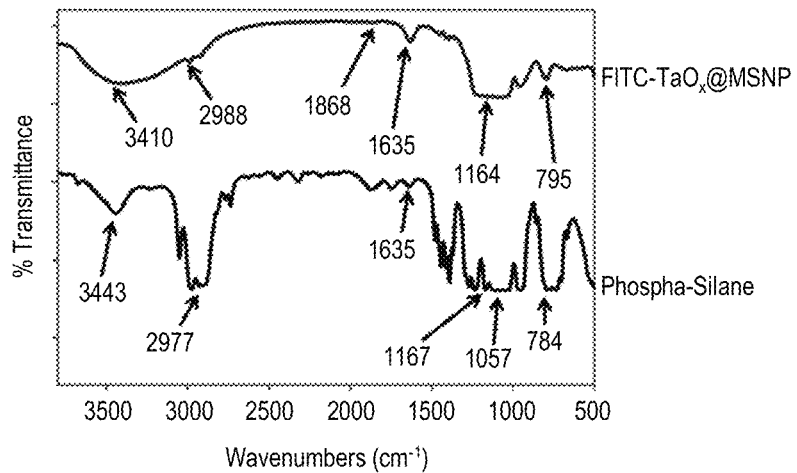

FIGS. 72A-72C show FTIR spectra comparing the as-synthesized FITC-$TaO_x$@MSNPs prepared in accordance with various aspects of the current technology and the starting material FITC-$TaO_x$ NC4 (FIGS. 72A-72B) and Phospha-Silane (FIG. 72C). Prominent and common transmittance peaks are pointed out.

Figure 73A:
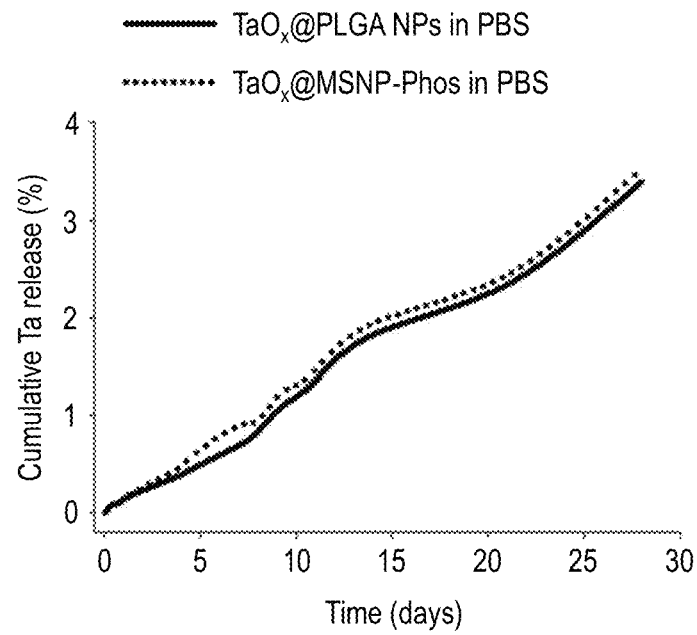
Figure 73B:
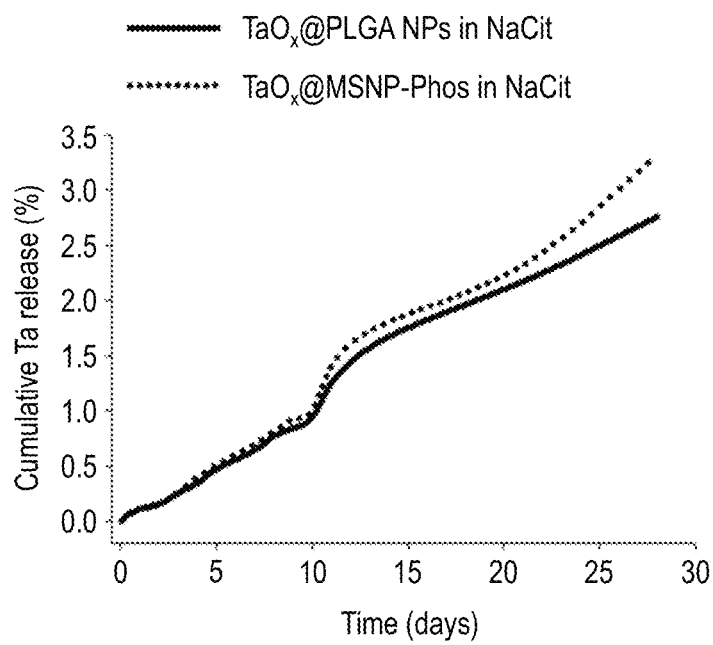

FIGS. 73A-73B show Ta dissolution from $TaO_x$@PLGA NPs and $TaO_x$@MSNP-Phos prepared in accordance with various aspects of the current technology over 4 weeks using ICP-OES (n=3, S.D.<0.5). In FIG. 73A, the $TaO_x$@PLGA NPs and $TaO_x$@MSNP-Phos are in PBS (pH 7.4), and in FIG. 73B, the $TaO_x$@PLGA NPs and $TaO_x$@MSNP-Phos are in NaCit (pH 5.5).

Figure 74A:
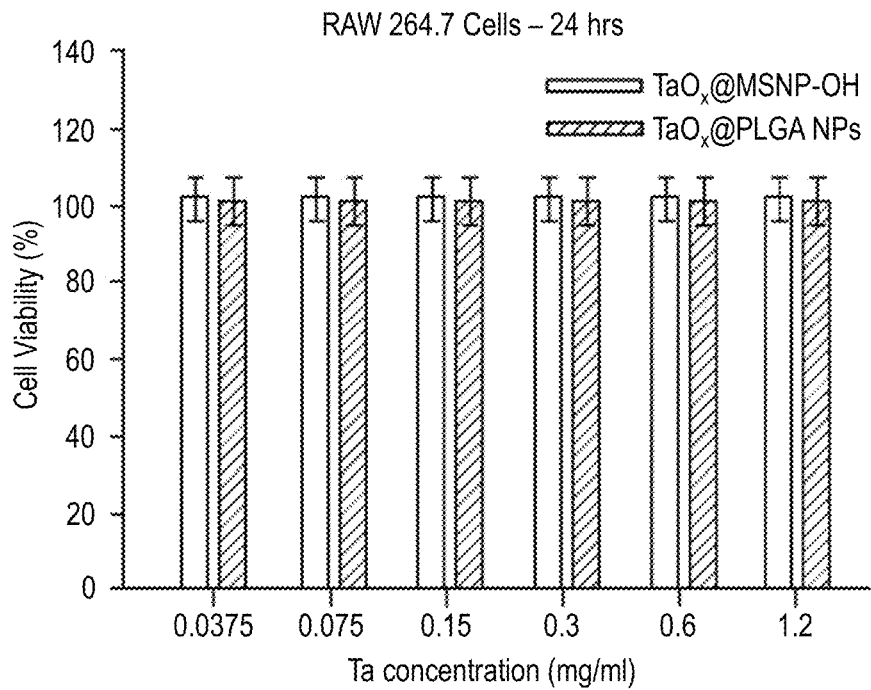
Figure 74B:
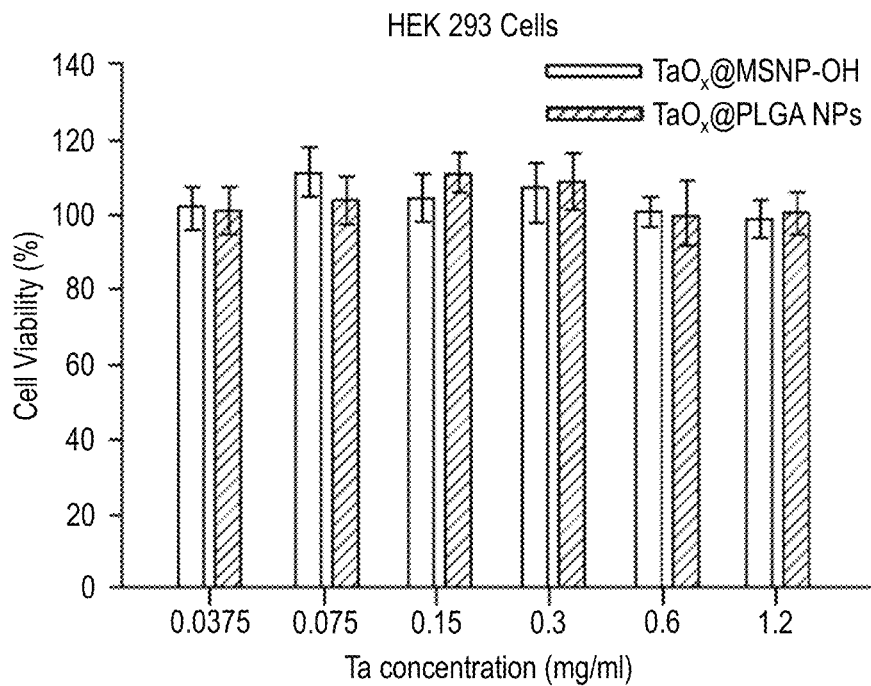

FIGS. 74A-74B show the results of an MTT cytotoxicity assay for different concentrations of $TaO_x$@PLGA NPs and $TaO_x$@MSNP-OH types prepared in accordance with various aspects of the current technology that were incubated with cultured RAW 264.7 macrophage cells (FIG. 74A) and HEK 293 fibroblast cells (FIG. 74B) for 24 hours each.

Figure 75A:
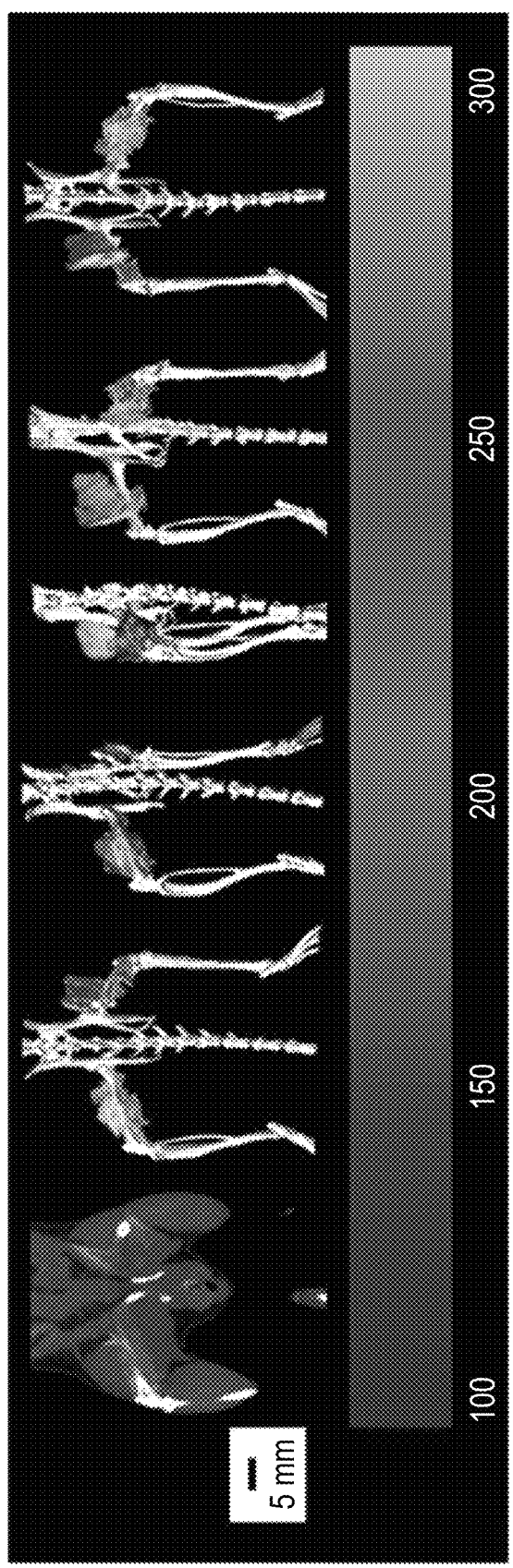
Figure 75B:
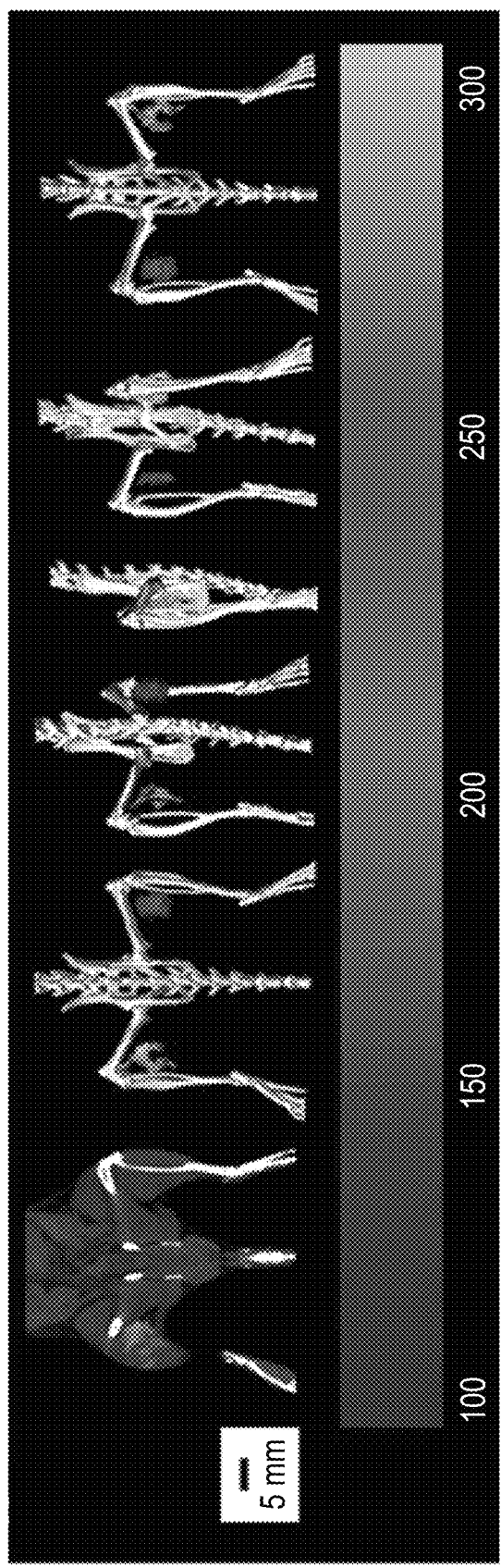
Figure 75C:
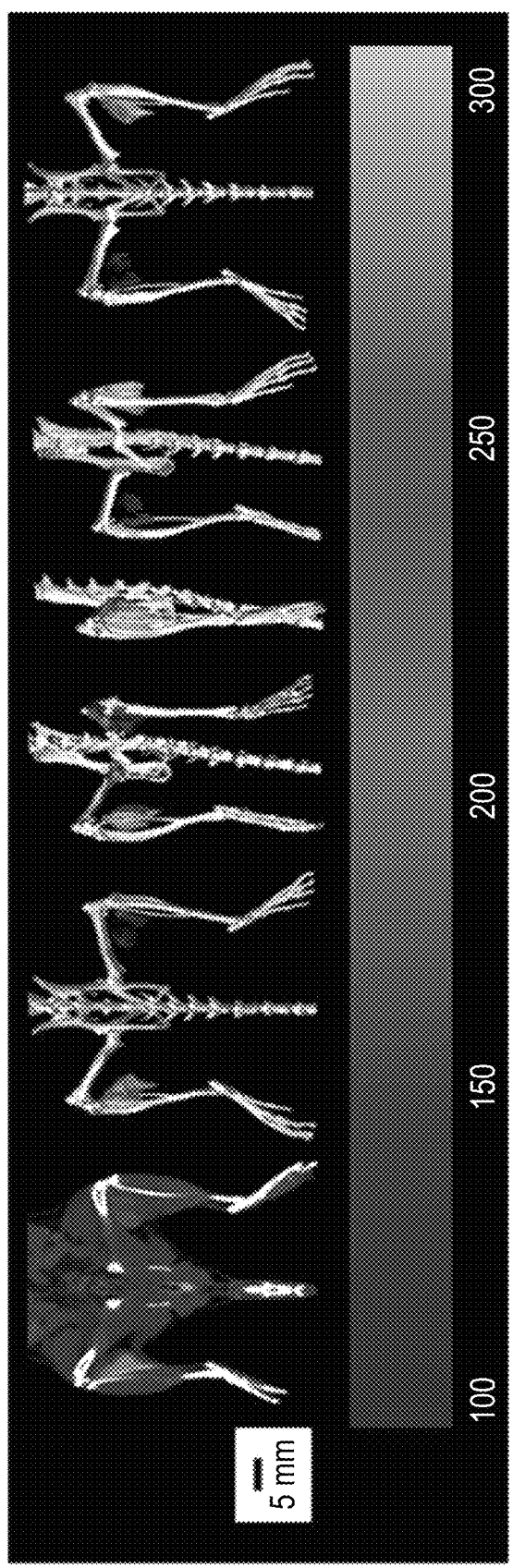

FIGS. 75A-75C shows immediate post-injection micro-CT three-dimensional image renderings of BALB/c mice. In FIG. 75A, single, 50 µL bolus doses of 50 mM $TaO_x$@PLGA NPs and $TaO_x$@MSNP-Phos prepared in accordance with various aspects of the current technology were injected; HU color map shows hyperintensity of the $TaO_x$@MSNPs (left leg) and $TaO_x$@PLGA NPs (right leg); injections were administered between the superficial gluteal muscle and biceps femoris muscle. In FIG. 75B, single 50 µL bolus doses of $TaO_x$@PLGA NPs, 50 mM and 25 mM Ta each, were injected. In FIG. 75C, single 50 µL bolus doses of $TaO_x$@MSNP-Phos, 50 mM, and 25 mM Ta each were injected; HU color maps shows hyperintensity of the 50 mM Ta dose (left leg) and 25 mM Ta dose (right leg); injections were administered bilaterally (IM) between the gastrocnemius muscle and caudal tibial muscle.

Figure 76A:
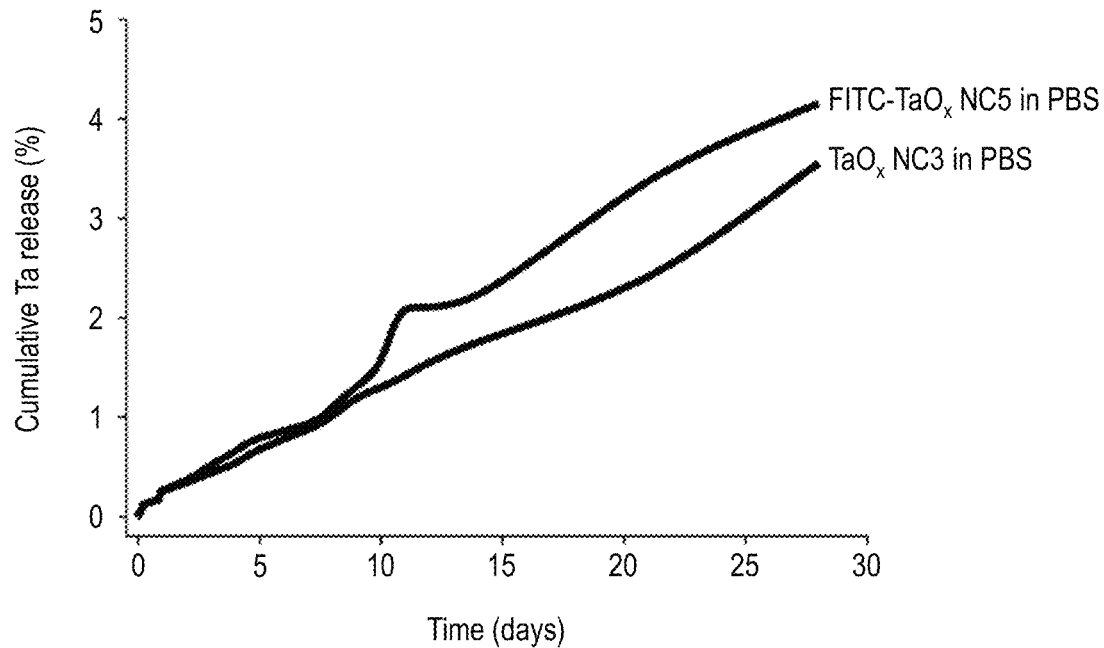
Figure 76B:
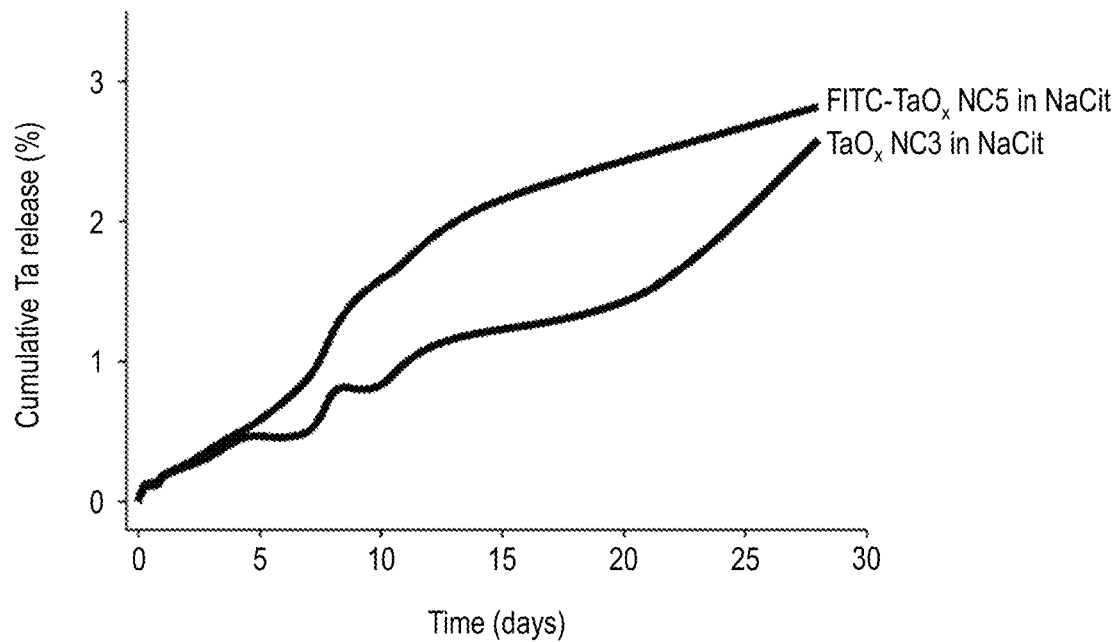

FIGS. 76A-76B shows Ta dissolution from $TaO_x$ NC3 and FITC-$TaO_x$ NC5 prepared in accordance with various aspects of the current technology over 4 weeks using ICP-OES (n=3, S.D.<0.5). In FIG. 76A, the $TaO_x$ NC3 and FITC-$TaO_x$ NC5 are in PBS. In FIG. 76B, the $TaO_x$ NC3 and FITC-$TaO_x$ NC5 are in NaCit (pH 5.5).

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "connected to," or "coupled to" another element, it may be directly on, connected or coupled to the other element, or intervening elements may be present. In contrast, when an element is referred to as being "directly on," "directly connected to," or "directly coupled to" another element or layer, there may be no intervening elements present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges. Example embodiments will now be described more fully with reference to the accompanying drawings.

The current technology provides a tantalum nanoparticle that is useful as a contrast agent for CT imaging, a drug delivery agent, a biomaterial, e.g., for scaffolds, and the like. The tantalum nanoparticle can be embedded within a polymer, provided in a solution, and/or isolated as a lyophilized powder.

Figure 1:
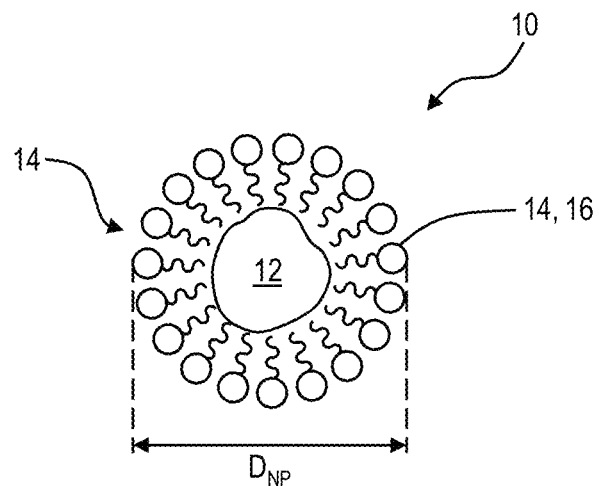
FIG. 1 is a schematic illustration of a first nanoparticle in accordance with various aspects of the current technology.

With reference to FIG. 1, the current technology provides a nanoparticle 10 comprising a core 12 and a covalent coating 14 covalently bound to the core 12. In certain aspects, the nanoparticle 10 is provided as a nanoparticle composition comprising a plurality of the nanoparticles 10. The core 12 comprises tantalum oxide. As non-limiting examples, the tantalum oxide can be $Ta_2O_5$, $TaO_x$, where $0<x\leq2$, for example, TaO and/or $TaO_2$, or combinations thereof.

The covalent coating 14 comprises a surface modifier 16 that modulates how the nanoparticle 10 interacts with water, i.e., the surface modifier 16 of the covalent coating 14 modulates the hydrophobicity and/or hydrophilicity of the nanoparticle 10. The surface modifier also provides a chemistry that can be further modified, such as through covalent or non-covalent interactions, as discussed in more detail below. As non-limiting examples, the surface modifier 16 can be (3-aminopropyl)trimethoxy silane (APTMS), (3-aminopropyl)triethoxy silane (APTES), APTMS-methoxy-poly (ethylene-glycol)-succinimidyl glutarate (APTMS-m-PEG-glutarate), APTES-methoxy-poly(ethylene-glycol)-succinimidyl glutarate (APTES-m-PEG-glutarate), 2-[methoxy (polyethyleneoxy)-9-12-propyl]trimethoxysilane (PEG-Silane), hexadecyltriethoxy silane, or combinations thereof. The surface modifier 16 is covalently bound to the core 12.

In some aspects, a fluorescent dye is conjugated to the surface modifier, such as to APTMS and/or APTES. Non-limiting examples of fluorescent dyes include fluorescein isothiocyanate (FITC), rhodamine B isothiocyanate (RITC), and a combination thereof. For example, the surface modifier 16 can be FITC-APTMS, RITC-APTMS, FITC-APTES, RITC-APTES, or combinations thereof.

The nanoparticle 10, including the core 12 and the covalent coating 14, has a diameter $D_{NP}$ of greater than or equal to about 1 nm to less than or equal to about 50 nm, greater than or equal to about 1 nm to less than or equal to about 40 nm, greater than or equal to about 1 nm to less than or equal to about 30 nm, or greater than or equal to about 1 nm to less than or equal to about 20 nm.

The nanoparticle 10 has a tantalum concentration of greater than or equal to about 10 wt. %, greater than or equal to about 20 wt. %, greater than or equal to about 30 wt. %, greater than or equal to about 40 wt. %, greater than or equal to about 50 wt. %, greater than or equal to about 60 wt. %, or greater than or equal to about 70 wt. %. In some aspects, the tantalum concentration is greater than or equal to about 10 wt. % to less than or equal to about 80 wt. %, greater than or equal to about 35 wt. % to less than or equal to about 75 wt. %, or greater than or equal to about 40 wt. % to less than or equal to about 80 wt. %. The wt. % is based on the total weight of the nanoparticle 10, i.e., the combined weight of the core 12 and the covalent coating 14 or the total weight of tantalum in a plurality of nanoparticles 10.

Figure 2:
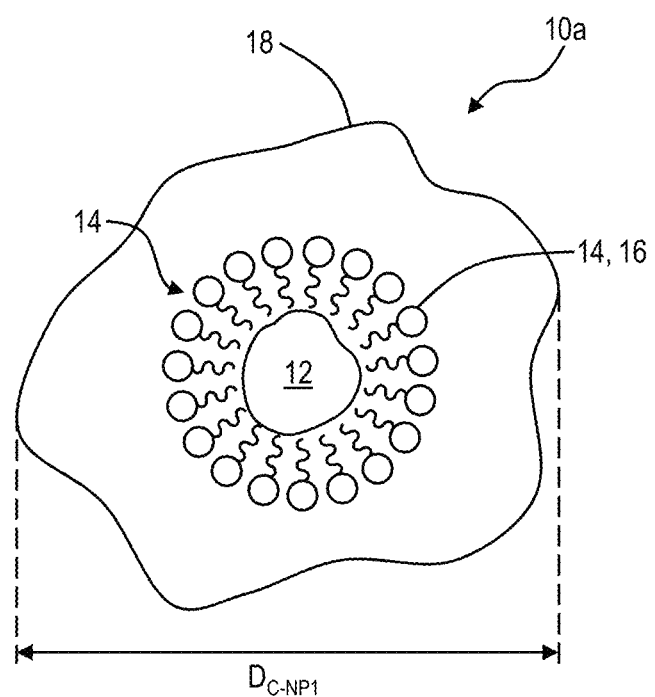
FIG. 2 is a schematic illustration of a second nanoparticle in accordance with various aspects of the current technology.

With reference to FIG. 2, in some aspects, the nanoparticle 10 is a nanoparticle 10a that further comprises a non-covalent coating 18. The non-covalent coating 18 is non-covalently associated with the covalent coating 14 comprising the surface modifier 16. For example, the core 12 and the covalent coating 14 can be at least partially embedded, which includes entirely embedded, within the non-covalent coating 18. The non-covalent coating comprises a polymer, the polymer being hydrophobic or at least not hydrophilic. The polymer comprises acrylics (including acrylate polymers (including poly(methyl acrylate) (PMA)), acrylonitrile polymers and copolymers, maleic anhydride copolymers, methacrylate polymers (including poly(methyl methacrylate) (PMMA), poly(butyl methacrylate) (PDMA), poly(ethyl methacrylate) (PEMA), and combinations thereof), amides and imides (including nylon 6, nylon 6/6, nylon 6/12, nylon 11, nylon 12, and combinations thereof), carbonates (including poly(bisphenol A carbonate), poly (propylene carbonate), and combinations thereof), dienes, esters (including poly(lactic-co-glycolic acid) (PLGA), poly (ethylene terephthalate) (PET), polycaprolactone (PCL), and combinations thereof), fluorocarbons (including polytetrafluoroethylene (PTFE), poly(vinylidene fluoride, and combinations thereof), olefins (including polybutylene, polyethylene, polypropylene, and combinations thereof), styrenes (including polystyrene), vinyl acetals, vinyl and vinylidene chlorides (including poly(vinyl chloride) (PVC)), vinyl esters (including poly(vinyl acetate) (PVA), poly(vinyl cinnamate), and combinations thereof), vinyl ethers and ketones (including poly(ethyl vinyl ether), poly(vinyl methyl ketone), and combinations thereof), vinylpyridine and vinylpyrrolidone polymers (including poly(vinylpyridine), poly(vinylpyrrolidone), and combinations thereof), silicones (polydimethylsiloxane (PDMS)), biopolymers (including cellulose, chitin, and combinations thereof), copolymers thereof, and combinations thereof, as non-limiting examples.

Figure 3:
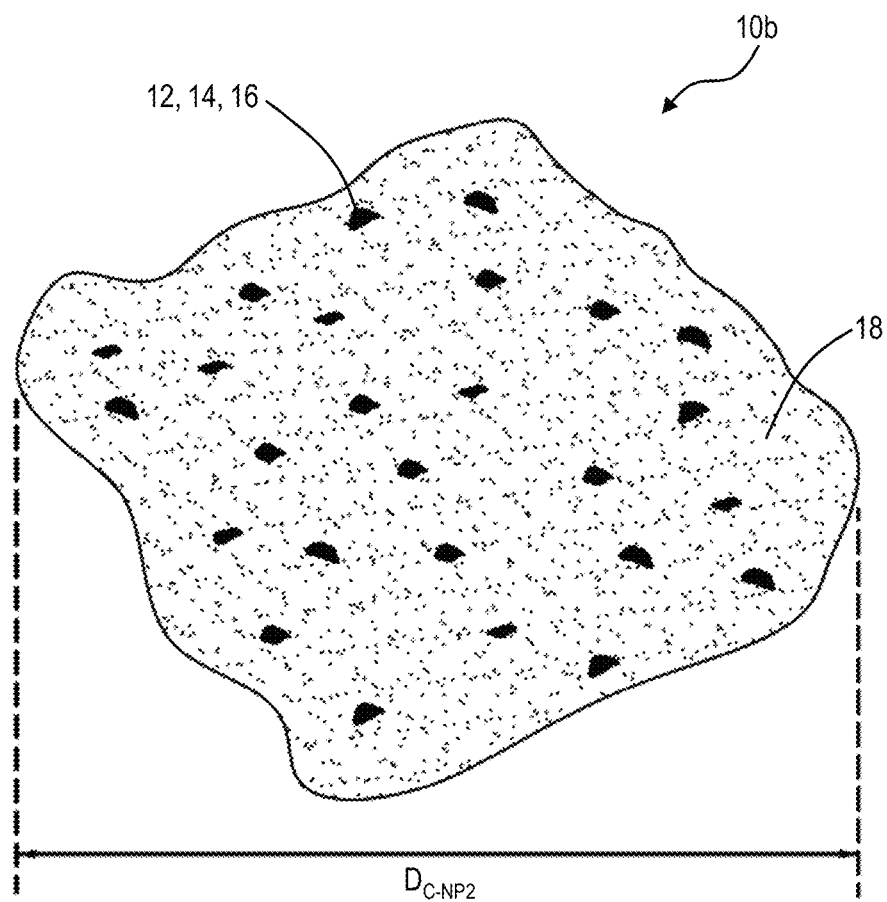
FIG. 3 is a schematic illustration of a third nanoparticle in accordance with various aspects of the current technology.

In some aspects, such as shown in FIG. 2, a single nanoparticle 10a is non-covalently embedded with the non-covalent coating 18. The nanoparticle 10a, including the core 12, the covalent coating 14, and the non-covalent coating 18 has a diameter $D_{C\text{-}NP1}$ greater than or equal to about 20 nm to less than or equal to about 500 nm, including diameters $D_{C\text{-}NP1}$ of about 20 nm, about 50 nm, about 100 nm, about 150 nm, about 200 nm, about 250 nm, about 300 nm, about 350 nm, about 400 nm, about 450 nm, about 500 nm, or diameters therebetween. In other aspects, such as shown in FIG. 3, the nanoparticle 10 is a nanoparticle 10b comprising at least two, i.e., a plurality, of constructs comprising the core 12 and the covalent coating 14 comprising the surface modifier 16 at least partially embedded within the non-covalent coating 18. Here, the nanoparticle 10b has a diameter $D_{C\text{-}NP2}$ of greater than or equal to about 100 nm to less than or equal to about 1000 nm, including diameters $D_{C\text{-}NP2}$ of about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, or diameters therebetween.

In certain aspects, the nanoparticle 10, i.e., the core 12 comprising the covalent coating 14, is embedded within a mesoporous silica nanoparticle (MSNP). The MSNPs are nanoparticles with a silica framework that is mesoporous, i.e., the nanoparticles have a surface that defines pores having a diameter of greater than or equal to about 2 nm to less than or equal to about 50 nm greater, greater than or equal to about 2 nm to less than or equal to about 40 nm, greater than or equal to about 2 nm to less than or equal to about 30 nm, greater than or equal to about 2 nm to less than or equal to about 20 nm, greater than or equal to about 2 nm to less than or equal to about 10 nm, or greater than or equal to about 2 nm to less than or equal to about 6 nm. However, it is understood that the silica nanoparticle may have pores with a diameter that is outside of the foregoing range, and as such, may be a microporous silica nanoparticle having pores with a diameter of less than about 2 nm, such as pores having a diameter of greater than or equal to about 950 nm to less than about 2 nm or a macroporous silica nanoparticle having pores with a diameter of greater than about 50 nm, such as pores having a diameter of greater than about 50 nm to less than or equal to about 100 nm.

In various aspects, the nanoparticle 10, 10a, and/or 10b further comprises a therapeutic agent coupled to the covalent coating 14. The therapeutic agent can be directly coupled to the covalent coating 14 or it can be indirectly coupled to the covalent coating 14, for example, by a linker or by way of the non-covalent coating 18. The therapeutic agent can be a small molecule, a peptide, a protein, a nucleic acid, a cell, or combinations thereof, as non-limiting examples. As such, the therapeutic agent can be a chemotherapeutic agent, an antibody, an antibody fragment, or an oligonucleotide, i.e., a DNA molecule and/or an RNA molecule. The antibody or antibody fragment is a polyclonal or monoclonal antibody that selectively binds to a protein or peptide that is selectively expressed on a cell of interest. In certain other aspects, the antibody or antibody fragment is an antibody fragment, such as, for example, Fab, Fab', $Fab_2$, $Fab'_2$, Fd, Fd', scFv, $scFv_2$, dAb, or combinations thereof, or a chimeric antibody fragment fusion molecule, wherein the antibody fragment or the chimeric antibody fragment fusion molecule selectively binds to a protein that is expressed on a cell of interest.

Unless specifically stated otherwise, the term "nanoparticle" used herein includes the nanoparticle 10 of FIG. 1, the nanoparticle 10a of FIG. 2, the nanoparticle 10b of FIG. 3, and combinations thereof. Moreover, it is understood that when referring to "the nanoparticle 10, 10a, 10b," a plurality of the nanoparticles 10, a plurality of the nanoparticles 10b, a plurality of the nanoparticles 10c, and combinations thereof are contemplated and included. The nanoparticle 10, 10a, 10b can be provided as a lyophilized powder.

The current technology also provides a composition comprising the nanoparticles 10, 10b, 10c. In some aspects, the composition comprises the nanoparticles 10, 10b, 10c dissolved or suspended in a solution. The solution can be a pharmaceutically acceptable carrier or excipient, such as when the nanoparticles are used as a contrast agent and/or as a carrier for a therapeutic agent, or it can be a bio-ink used for three-dimensional printing.

The bio-ink comprises a liquid carrier and optionally an initiator and/or cross-linker to facilitate solidification into a printed shaped object or scaffold. The nanoparticles 10, 10b, 10c are dissolved or suspended within the liquid carrier. The liquid carrier comprises a polymer, such as agarose, alginate, chitosan, collagen, fibrin, gelatin, poly(ethylene glycol)-PEG, polyethylene (glycol) diacrylate (PEGDA), poly (ethylene glycol) methacrylate/dimethacrylate (PEGDMA), poly (D, l)-lactic acid-co-glycolic acid), poloxamers (e.g., pluronic F127), poly(2-hydroxyethyl methacrylate)-pHEMA, poly(lactic acid) (PLA), poly-glycolic acid (PGA), poly(lactic-co-glycolic acid) (PLGA), poly-caprolactone (PCL), hyaluronan, and combinations thereof, as non-limiting examples. In some aspects, the liquid carrier is a hydrogel comprising at least one of the above polymers. Non-limiting examples of cross-linkers include $CaCl_2$, NaOH, $Na_5P_3O_{10}$, glutaraldehyde, glycine, (1-ethyl-3-(3-dimethylaminopropyl)-carbodiimide (EDC)), N-hydroxysuccinimide (NHS), epoxy compounds, 6-methylene diisocyanate, glycerin, alginate, genipin (GP), nordihydroguaiaretic acid (NDGA), tannic acid, procyanidins (PC), amino acids, adipic acid, hexane diamine, and combinations thereof. The carrier can also comprise calcium phosphate (e.g., $CaHPO_4$, $Ca_8H_2(PO_4)_6 \cdot 5 \cdot H_2O$, $Ca_3(PO_4)_2$, $Ca_3(PO_4)_2 \cdot nH_2O$, and combinations thereof), hydroxyapatite, orthophosphoric acid ($H_3PO_4$), pyrophosphoric acid ($H_7P_2O_7$), cells, a therapeutic agent (e.g., a growth factor, a protein, an antibody or antibody fragment, an active pharmaceutical ingredient, and combinations thereof), bone cement, and combinations thereof.

In other aspects, the composition comprises a solid polymeric matrix that at least partially surrounds and embeds the nanoparticles 10, 10a, 10b. The polymeric matrix can be in the form of a two-dimensional planar film or the polymeric matrix can have a predetermined three-dimensional geometry. The polymeric matrix comprises a polymer, including any of those described above in relation to the non-covalent coating 18 and to the bio-ink. In certain aspects, the solid polymeric matrix is a biological scaffold or implant having a predetermined shape. Exemplary scaffolds have a honeycomb structure and can be formed by three-dimensional printing with the above-described bio-ink or by casting methods known in the art. For example, a biological scaffold can prepared by disposing a polymer comprising the nanoparticles 10, 10a, 10b about a mask, i.e., a template, having a predetermined shape and solidifying the polymer. The mask can be a mandrel having a honeycomb structure, such as a plurality of interconnected circles, ovals, or polygons (e.g., squares, pentagons, hexagons, and the like). The mask is optionally removed after the polymer comprising the nanoparticles 10, 10a, 10b is solidified.

The current technology also provides a method of synthesizing the nanoparticles 10, 10a, 10b. The method comprises combining an organic solvent with an aqueous solution to form a water-in-oil micro-emulsion. The organic solvent includes cyclohexane, hexane, heptane, octane, isooctane, nonane, decane, toluene, or combinations thereof, as non-limiting examples. The aqueous solution includes a $C_{1-8}$ alcohol (e.g., ethanol), acetonitrile, a $C_{1-8}$ ether, acetone, or combinations thereof, as non-limiting examples. The method then comprises adding a base catalyst comprising a base to the micro-emulsion, the base comprising NaOH, KOH, or combinations thereof.

Next, the method comprises adding a surfactant to the micro-emulsion. In certain aspects, the surfactant is polyoxyethylene (5) nonylphenylether (e.g., IGEPAL®—CO-520 polyoxyethylene (5) nonylphenylether by Rhodia and commercialized by Sigma-Aldrich), polyoxyethylene sorbitan (Tween® polyoxyethylene sorbitol ester by Croda Americas, Inc.), poloxamer, sorbitan ester (Span™ sorbitan ester by Croda Americas, Inc.), or combinations thereof, as non-limiting examples.

The method further comprises adding tantalum to the micro-emulsion, which results in the formation of uncoated nanocrystals (NCs). The tantalum can be added as a tantalum salt, a tantalum alkoxide, or combinations thereof. Tantalum alkoxides include $C_1$-$C_4$ tantalum alkoxide, such as tantalum (V) ethoxide.

The method also comprises covalently binding a surface modifier 16 (as described above) to the uncoated NCs to form the covalent coating 14. It is understood that the surface modifier 16 can be 3-aminopropyl)trimethoxy silane (APTMS), (3-aminopropyl)triethoxy silane (APTES), APTMS-methoxy-poly(ethylene-glycol)-succinimidyl glutarate (APTMS-m-PEG-glutarate), APTES-methoxy-poly(ethylene-glycol)-succinimidyl glutarate (APTES-m-PEG-glutarate), 2-[methoxy (polyethyleneoxy)-9-12-propyl] trimethoxysilane (PEG-Silane), hexadecyltriethoxy silane, or combinations thereof. As non-limiting examples, the surfactant can be polyoxyethylene (5) nonylphenylether (e.g., IGEPAL®—CO-520 polyoxyethylene (5) nonylphenylether by Rhodia and commercialized by Sigma-Aldrich), polyoxyethylene sorbitan (Tween® polyoxyethylene sorbitol ester by Croda Americas, Inc.), poloxamer, sorbitan ester (Span™ sorbitan ester by Croda Americas, Inc.), or combinations thereof.

Adding the surface modifier 16 results in the formation of a solution comprising the nanoparticles 10. Then, the method comprises dialyzing the solution comprising the nanoparticles 10 in water using dialysis bags having a molecular weight cut-off (MWCO) of, for example, from about 12 kDa to about 14 kDa and optionally lyophilizing the nanoparticles 10, which are now dissolved or suspended in the water.

By controlling the surface modifier 16, its concentration and/or the ratio of at least two surface modifiers 16, the hydrophobicity or hydrophilicity of the resulting nanoparticles 10, 10a, 10b can be manipulated. For example, contacting the uncoated NCs with a combination of PEG-Silane and APTMS and/or APTES and then further contacting the now partially-coated NC with methoxy polyethylene glycolsuccinimidyl glutamate ester (mPEG-SG) results in the nanoparticles 10 having the covalent coating 14 comprising the surface modifiers 16 of PEG-Silane and APTMS-m-PEG-glutarate and/or APTES-m-PEG-glutarate, which after the dialysis, is highly hydrophilic. The scheme for the generation of TaO$_x$ NC1 of FIGS. 4A and 4B, discussed in more detail below, is exemplary of this method and the resulting nanoparticle 10.

As another example, contacting the uncoated NCs with only PEG-Silane results in the nanoparticles 10 having the covalent coating 14 comprising the surface modifier 16 of PEG-Silane, which after the dialysis, is hydrophilic, but less hydrophilic relative to the previously described example. The scheme for the generation of TaO$_x$ NC2 of FIGS. 4A and 4C, discussed in more detail below, is exemplary of this method and the resulting nanoparticle 10.

As another example, contacting the uncoated NCs with a combination of PEG-Silane and APTMS and/or APTES only results in the nanoparticles 10 having the covalent coating 14 comprising the surface modifiers 16 of PEG-Silane and APTMS and/or APTES, which after the dialysis, is hydrophobic. The scheme for the generation of TaO$_x$ NC3 of FIGS. 4A and 4D, discussed in more detail below, is exemplary of this method and the resulting nanoparticle 10.

As another example, contacting the uncoated NCs with PEG-Silane and then further contacting the now partially coated NC with a dye conjugated to APTMS and/or APTES results in the nanoparticles 10 having the covalent coating 14 comprising the surface modifiers 16 of PEG-Silane and the dye conjugated to APTMS and/or APTES, which after the dialysis, is hydrophilic and fluorescent. The scheme for the generation of FITC-TaO$_x$ NC4 of FIGS. 4A and 4E, discussed in more detail below, is exemplary of this method and the resulting nanoparticle 10.

As another example, contacting the uncoated NCs with a combination of PEG-Silane and APTMS and/or APTES and then further contacting the now partially coated NC with a dye conjugated to APTMS and/or APTES results in the nanoparticles 10 having the covalent coating 14 comprising the surface modifiers 16 of PEG-Silane, APTMS and/or APTES, and the dye conjugated to APTMS and/or APTES, which after the dialysis, is hydrophobic and fluorescent. The scheme for the generation of FITC-TaO$_x$ NC5 of FIGS. 4A and 4F, discussed in more detail below, is exemplary of this method and the resulting nanoparticle 10.

Figure 4B:
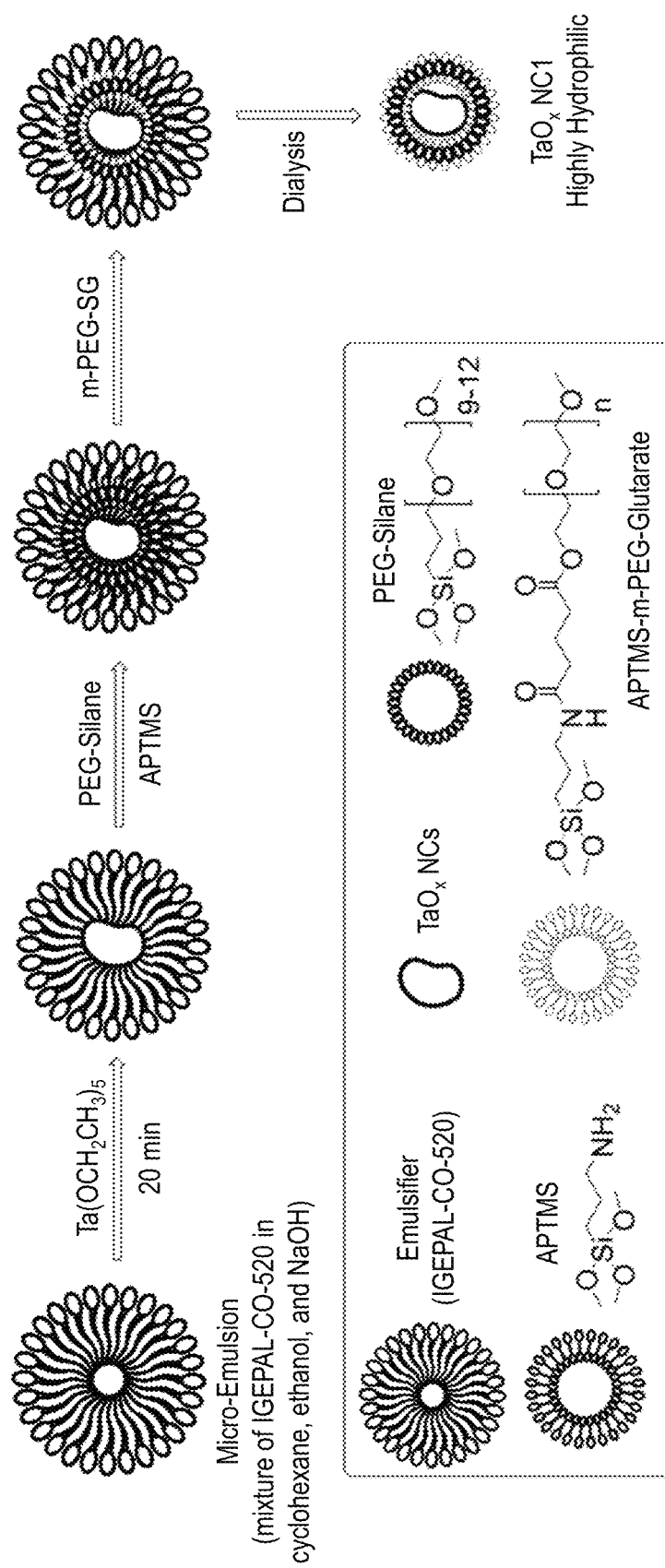

As another example, contacting the uncoated NCs with a combination of PEG-Silane and hexadecyltriethoxy silane results in the nanoparticles 10 having the covalent coating 14 comprising the surface modifiers 16 of PEG-Silane and the hexadecyltriethoxy silane, which after the dialysis, is hydrophobic. Although not shown exactly, the generation of TaO$_x$ NC3 of FIGS. 4A and 4D is exemplary of this method and the resulting nanoparticle 10, where the APTMS is replaced with the hexadecyltriethoxy silane. In certain aspects, the method further comprises disposing the non-covalent coating 18 on the nanoparticles 10 to form the further coated nanoparticles 10a, 10b.

Specific examples of methods of making the nanoparticles 10 are provided in the following example with reference to FIGS. 4A-4F. Embodiments of the present technology are further illustrated through the following non-limiting example.

Example

In this example, a preliminary silane-coated TaO$_x$ NC (NC0) is synthesized, which can then be chemically modified to impart different degrees of hydrophilicity and to impart fluorescence. Highly hydrophilic versions of these NCs (NC1) were left bare and investigated for vascular/vessel imaging. Moderately hydrophilic versions of these NCs (NC2) and hydrophobic versions of these NCs (NC3) were encapsulated separately into two diverse polymeric constructs—NC2 into MSNPs and NC3 into PLGA NPs. These two NP types are promising drug delivery vehicles within which TaO$_x$ enables the opportunity for image-guided drug delivery by CT. A multifarious set of in vivo micro-CT demonstrations with this diverse set of NPs establishes the versatility and utility of TaO$_x$-based NPs, and in vitro and in vivo toxicology assays demonstrate the acute non-toxic nature of these materials, showing that the TaO$_x$-based NPs are useful for clinical CT molecular imaging.

SUMMARY

The synthesis, characterization, and in vitro and in vivo performance of a series of exemplary TaO$_x$-based NPs for CT are described in this example. Five distinct versions of 9-12 nm diameter silane-coated TaO$_x$ NCs were fabricated by a sol-gel method with varying degrees of hydrophilicity and with or without fluorescence, with the highest reported Ta content to date (78%). Highly hydrophilic NCs were left bare and evaluated in vivo in mice for micro-CT of full body vasculature, where following intravenous injection, TaO$_x$ NCs demonstrate high CT contrast, circulation in blood for approximately 3 hours, and eventual accumulation in RES organs and where following injection locally in the mammary gland, the full ductal tree structure can be clearly delineated. Partially hydrophilic NCs were encapsulated within MSNPs (TaO$_x$@MSNPs) and hydrophobic NCs were encapsulated within PLGA (TaO$_x$@PLGA) NPs, serving as potential CT-imagable drug delivery vehicles. Bolus intramuscular injections of TaO$_x$@PLGA NPs and TaO$_x$@MSNPs to mimic the accumulation of NPs at a tumor site produce high signal enhancement in mice. In vitro studies on bare NCs and formulated NPs demonstrate high cytocompatibility and low dissolution of TaO$_x$. This example demonstrates that TaO$_x$-based NPs are versatile contrast agents for CT.

Experimental

General Details

Unless otherwise stated, all reagents and solvents were purchased from the respective suppliers and used as received without any further purification. The details for various chemicals and their suppliers are provided below. Details for synthesizing each type of NC and NP, along with general information on the instruments used for characterization of the NCs and NPs are also provided below. Specific details for various in vitro and in vivo experiments are also provided.

Synthetic Procedures

TaO$_x$ NC synthesis: In a 250 ml one neck round bottom flask fitted with a septa, IGEPAL®—CO-520 poly(oxyethylene)nonylphenyl ether ($M_n$ 441, 23.0 g), cyclohexane (200 mL), and ethanol (2.5 mL) were added and the contents stirred to obtain a clear solution. To this stirring mixture, a solution of sodium hydroxide (100 mM, 2.5 mL) was added, and this micro-emulsion was sonicated in a water bath to ensure homogeneity. Next, tantalum (V) ethoxide, (Ta$_2$O$_5$, 0.5 mL) was added in one portion and the contents stirred at ambient temperature for 20 minutes. On addition of Ta$_2$O$_5$, the otherwise clear solution gives way to slight turbidity, indicating the formation of uncoated NCs, which are referred to herein as NCO. At this stage of the reaction, different silane end group reactants were added to form NCs with varying degrees of hydrophilicity/hydrophobicity or to append fluorescent tags to the NC surface. On exclusive addition of PEG-Silane (3.0 mL) followed by subsequent work up, the partially hydrophilic TaO$_x$ NC2 were isolated. At the same stage, addition of APTMS (0.028 mL) and subsequent surface modification using methoxy-poly(ethylene-glycol)-succinimidyl glutarate (m-PEG-SG-200, 50 mg) in ethanol generates the highly water soluble TaO$_x$ NC1. Altering the ratio of PEG-Silane and APTMS in favor of a higher concentration of the latter (1:6 ratio, v/v) followed by subsequent work up leads to the hydrophobic TaO$_x$ NC3. To synthesize the respective fluorescent analogues, a preformed FITC-APTMS linker was introduced into the reaction mixture after the addition of PEG-Silane and APTMS and the subsequent steps were carried out in dark. Addition of the fluorescent linker to the respective hydrophilic/hydrophobic reaction mixture leads to the formation of hydrophilic FITC-TaO$_x$ NC4 and hydrophobic FITC-TaO$_x$ NC5, respectively. Once the reaction is complete, all NC types were isolated by centrifugation as an oily pellet and purified by exhaustive dialysis in water using 12-14 kDa MWCO dialysis bags. This is followed by lyophilization to yield NCs as a dry powder. For specific details, refer to "Synthesis of Tantalum Oxide NCs" in Section 1 of the following "Additional Aspects of the Example" section.

TaO$_x$@PLGA NP synthesis: In a 50 mL falcon tube, 4% polyvinyl alcohol (PVA, 3 mL) was taken. In a separate 15 mL falcon tube, 1.0 mL of the TaO$_x$ NC3 suspension in dichloromethane (DCM; 25 mg TaO$_x$ NC3 in 1 mL DCM) was taken and 0.5 mL PLGA (LG 50:50, acid terminated) stock solution in DCM (12.5 mg PLGA polymer in 0.5 mL DCM) was added dropwise to it with continuous vortex. The resulting white colored suspension was sonicated for 5 minutes with periodic vortex. This solution was next added dropwise to the 4% aqueous PVA solution (3 mL) in the 50 mL falcon tube with rigorous and continuous vortex. Upon completion of addition, the resulting white suspension was tip sonicated at 40% amplitude for 20 seconds and then transferred to an ice bath for 10 seconds. This process of tip sonication followed by rapid cooling in an ice bath was repeated six times. After the final cycle, the white suspension was added to 10 mL 4% PVA and diluted further using 10 mL ultra-pure water. The resulting reaction mixture was stirred at room temperature (RT) for 3 hours to remove DCM, resulting in NP hardening. After 3 hours, the NPs were isolated by centrifugation at 15,000 rpm for 10 minutes. The white NPs were cleaned again by repeated dispersion in aqueous media and centrifugation to isolate the NPs until the supernatant was clear (3 times). Finally, the pellet was suspended in UP water and the TaO$_x$@PLGA NPs were re-collected as a dry powder by lyophilization. For the corresponding synthesis of the fluorescent FITC-TaO$_x$@PLGA NPs, the precursor TaO$_x$ NC3 was replaced with the hydrophobic, FITC-labeled TaO$_x$ NC5 and the subsequent reaction and purification steps were carried out in dark. For specific details, please refer to Section 7 in the following "Additional Aspects of the Example" section.

TaO$_x$@MSNP synthesis: In a 500 mL four neck round bottom flask fitted with three rubber septa and a screw top temperature probe, hexadecyl trimethylammonium bromide (CTAB, 800 mg) and triethanolamine (TEA, 0.5 mL) were added, and water (DI, 190 mL) was added to it. A previously prepared suspension of TaO$_x$ NC2 in water (200 mg in 10 mL) was added to this mixture. The flask was placed on a heating mantle and the temperature of the reaction mixture was maintained at 80° C. to obtain a white colored solution with slight turbidity. After 1 hour, tetraethyl orthosilicate (TEOS, 2.0 mL) was added and heating continued for another 2 hours. Next, the reaction mixture was cooled to ambient temperature. At this stage, different silane precursors were introduced into the reaction mixture to yield different TaO$_x$@MSNP types with distinct surface functionalities. The addition of PEG-Silane (2.0 mL) leads to formation of TaO$_x$@MSNP-OH, while the addition of (2-Diethylphosphatoethyl)triethoxysilane (Phospha-Silane, 2.0 mL) results in TaO$_x$@MSNP-Phos. Once the silane functionality is added, the reaction contents were stirred overnight. Next, the reaction mixture was diluted to three times its volume using methyl alcohol (MeOH, 200 mL) and the MSNPs were collected via centrifugation (15,000 rpm, 10 minutes) as a white colored pellet. This pellet was resuspended in a solution of hydrochloric acid (HCl) in MeOH (10% v/v, 100 mL), and this suspension was heated at reflux for 24 hours. After 24 hours, the reaction mixture was concentrated to a final volume of approximately 2 mL using a rotary evaporator and diluted to approximately 10 mL using DI water. This suspension was next transferred to 12-14 kDa dialysis bags and subjected to prolonged dialysis against DI water to purify the NPs. After extensive dialysis, the contents in the dialysis bags were lyophilized to obtain the desired product.

For the synthesis of fluorescent FITC-TaO$_x$@MSNP, an aqueous suspension of hydrophilic, FITC-labeled TaO$_x$ NC4 (200 mg in 10 mL water) was used instead of the TaO$_x$ NC2. The subsequent reaction steps were carried out in dark. For specific details and the synthesis of empty MSNPs, refer to Section 9 in the following "Additional Aspects of the Example" section.

Cell Culture

General information: RAW 264.7 (murine macrophage cells) and HEK 293 (human embryonic kidney cells) were grown in mono-layers using Dulbecco's Modified Eagle's Medium (DMEM (1X), Gibco®) supplemented with 10% (v/v) fetal bovine serum (FBS, Gibco®), and penicillin-streptomycin (100 units mL$^{-1}$ and 100 μg mL$^{-1}$, respectively, Anti-Anti (100-X), Antibiotic-Antimycotic, Gibco®) in a humidified atmosphere with 5% CO$_2$ at 37° C.

In vitro cell viability studies: Cell viability was evaluated for RAW 264.7 and HEK 293 cells incubated with TaO$_x$ NCs, TaO$_x$@PLGA NPs, and TaO$_x$@MSNPs using 3-(4,5-dimethylthiazol-2-yl)-2,5-diphenyltetrazolium bromide assays (MTT, Sigma Aldrich). In a typical experiment, 1×10$^4$ cells per well were cultured in 96-well plates overnight. Next, the cells were incubated with different concentrations of TaO$_x$ NCs and NPs (0, 0.0375, 0.075, 0.15, 0.30, 0.60, 1.2, and 2.4 mg of Ta mL$^{-1}$) for 24 hours. After the incubation period, cells were washed thrice with PBS and incubated with media containing the MTT reagent (0.5 mg mL$^{-1}$) for 4 hours to allow the formation of formazan crystals. Next, the solubilization reagent was added to each well and following further incubation to completely dissolve the purple crystals obtained in the earlier step, spectrophotometric absorbance from the plates was measured at 570 nm using an UV-Vis microplate reader (SpectraMax® 190, Molecular Devices).

Micro-CT Imaging

Phantom imaging: For in vitro phantom measurements, solutions of TaO$_x$ NC1 in saline were prepared at various concentrations (0, 20, 50, 80, and 100 mM Ta). Phantom CT images were acquired on a Perkin Elmer Quantum GX micro-CT scanner operating at 90 kVp and 88 μA. In vivo micro-CT: Micro-CT was used to demonstrate the versatility of TaO$_x$ NPs in a diverse set of in vivo experiments.

Experiment #1: Imaging the vasculature. BALB/c Mice (Charles River Laboratories, Inc.; sex: male, age: approximately 3 months, body weight: approximately 25 g) received either a single intravenous dose of TaO$_x$ NCs formulated in sterile saline (0.9% sodium chloride) at 100 mM (296 mg kg$^{-1}$ TaO$_x$ particles) (n=2) or 200 mM (592.3 mg kg$^{-1}$ TaO$_x$ particles) (n=3) TaO$_x$ NCs. Animals were serially imaged via micro-CT at 0 hours (baseline), immediate post-injection, and 1 hour, 3 hours, 24 hours, and 72 hours post-injection using a Perkin Elmer Quantum GX micro-CT. The following image acquisition parameters were used at each scan time point: 14 minute acquisition; 90 kVp/88 µA; Field of View (FOV), 72 mm; voxel resolution, 144 µm$^3$. After 72 hours, mice were euthanized and tissue sections were collected for histology and Ta analysis using ICP-OES.

Experiment #2: Imaging the ductal tree in mammary glands. FVB mice (Charles River Laboratories, Inc.; sex: female, age: 9-10 weeks), were serially imaged using a PerkinElmer Quantum GX micro-CT scanner at different times after intraductal injection as previously described with a solution containing 60 or 100 mM tantalum oxide nanocrystals as contrast agent. Serial micro-CT was performed with: 2 minute acquisition; 90 kVp/88 µA; FOV, 36 mm; voxel resolution, 72 µm$^3$.

Experiment #3: Imaging the 'accumulation' of TaO$_x$-embedded NPs at a single site. The accumulation of TaO$_x$-embedded NPs at a single site, such as in the case of tumor targeting, was mimicked by injecting concentrated NPs intramuscular as a single bolus bilaterally in the right and left leg muscle. Micro-CT was performed on animals (n=3) following injection of 27.4 mg kg$^{-1}$ in saline (50 mM Ta) or 13.7 mg kg$^{-1}$ in saline (25 mM Ta) TaO$_x$@PLGA NPs and 36.8 mg kg$^{-1}$ in saline (50 mM Ta) or 18.4 mg kg$^{-1}$ in saline (25 mM Ta) TaO$_x$@MSNP-Phos. Injected mice were evaluated using the same micro-CT scan parameters as in Experiment #1 at a single scan time point; immediate post-injection, micro-CT image rendering, segmentation, and analysis of whole body or individual mammary glands was performed using Caliper AnalyzeDirect®, v12.0 (Biomedical Imaging Resource, Mayo Clinic, Rochester, Minn.).

Results and Discussion

Design, Synthesis, and Characterization of TaO$_x$ NCs

Synthesis of TaO$_x$ NCs: The general synthetic approach for the various TaO$_x$ NCs is shown in FIG. 4A. In particular, refer to the pathways leading to TaO$_x$ NC1, TaO$_x$ NC2, and TaO$_x$ NC3 of FIGS. 4B, 4C, and 4D, respectively. In the first step, a surfactant promoted micro-emulsion is formed that acts as the reaction chamber for the generation of preliminary TaO$_x$ NCs (NCO). On addition of tantalum (V) ethoxide to this micro-emulsion, a base catalyzed sol-gel reaction ensues that results in rapid formation of NCO. The acidic (pH=5) surface of these preliminary TaO$_x$ NCs in the reaction micro-emulsion has pendant hydroxyl groups that have a high propensity to undergo condensation reaction with silanes, and, henceforth, the addition of a poly(ethylene glycol) moiety with a silane end cap (PEG-Silane) results in formation of well-dispersed hydrophilic TaO$_x$ NCs. At this point of the synthesis, a mixture of different commercially available silanes could be potentially employed to engineer the hydrophilicity/hydrophobicity of the NCs.

To demonstrate this, varying ratios of APTMS and PEG-Silane are incorporated to synthesize three different TaO$_x$ NC variants—a highly water soluble TaO$_x$ (NC1), a partially hydrophilic TaO$_x$ (NC2), and a hydrophobic TaO$_x$ (NC3). Similarly, a pre-formed cocktail of silane appended fluorescent tags could also be potentially introduced during this step to generate labeled TaO$_x$ NCs (see the pathways leading to FITC-TaO$_x$ NC4 and FITC-TaO$_x$ NC5 in FIGS. 4A, 4E, and 4F). To this end, by addition of a pre-formed FITC-APTMS-PEG linker during the surface modification step, both hydrophilic FITC-TaO$_x$ (NC4) and hydrophobic FITC-TaO$_x$ (NC5) were also synthesized. For each of the TaO$_x$ NC types, the purification steps involved isolation of the NCs as a sticky oil via centrifugation, followed by dialysis against DI water and lyophilization to generate the product as a dry powder (see "Synthesis of Tantalum Oxide NCs" in Section 1 of the following "Additional Aspects of the Example" section). In the absence of any surface-modifying silane moiety, the resulting TaO$_x$ NCs are clumped together in an agglomerated mass (see FIGS. 5A-5C) leading to an increase in overall size. Further, the exclusive addition of only APTMS did not result in well dispersed NCs (see FIGS. 6A-6C) and a small amount of PEG-Silane was required to avoid clumping. This suggests that surface protection of bare TaO$_x$ NCs using repeating PEG units is essential to prevent irreversible agglomeration of NCs, which could lead to compromised cell internalization, non-specific biodistribution, and increased toxicity. Further, the prolonged circulation of NP CT CAs is a desirable characteristic for effective CT imaging, and PEG coating on the surface of TaO$_x$ NCs can act as an antifouling agent, thereby enhancing the blood circulation time.

Characterization of TaO$_x$ NCs: Table 1 lists the characterization details of the different TaO$_x$ NC types. TEM of hydrophilic NC1 (see FIGS. 7A-7B and 8A-8C) and partially hydrophilic NC2 (see FIGS. 7C-7D and 9A-9C) dispersed in water and hydrophobic NC3 (see FIGS. 7E-7F and 10A-10C) dispersed in hexane confirm uniform and well-dispersed TaO$_x$ NCs with a narrow size distribution of approximately 9-12 nm in diameter. The hydrodynamic size (particle diameter) of NC1 and NC2 dispersed in water were approximately 12-18 nm (see Table 1), as measured by dynamic light scattering (DLS). The marginal increase in diameter in aqueous media can be explained by the formation of a hydration sphere around the NCs, as is routinely observed among various NP formulations. DLS measured negative zeta potentials for NC1 and NC2 (see Table 1), which can be attributed to the hydroxyl, alkoxy, and carboxylate surface groups. XRD experiments showed the amorphous nature of the NCs (see FIG. 11 for NC1, FIG. 12 for NC2, and FIG. 13 for NC3). The presence of Ta and its electronic state, as well as the presence of Si, was confirmed using EDS and XPS. The EDS spectra for all TaO$_x$ NC variants show clear peaks for Ta and Si, confirming the presence of these elements (see FIGS. 14A-14B for NC1, FIGS. 15A-15B for NC2, and FIGS. 16A-16B for NC3). Further confirmation of the electronic state of the TaO$_x$ NCs (x≈1) was ascertained from XPS spectra as shown in FIG. 17 (NC1), FIG. 18 (NC2), and FIG. 19 (NC3). The XPS peaks near 26 and 24, corresponding to Ta 4f$_{7/2}$ and Ta 4f$_{5/2}$ respectively, were similar to those reported for TaO. The presence of silane, PEG, and various other surface functionalities was confirmed by FTIR characterization (see FIGS. 20A-20D for NC1, FIGS. 21A-21B for NC2, and FIGS. 22A-22B for NC3), with specific details about important peaks discussed in the following "Additional Aspects of the Example" section. Importantly, the Ta content for all the NCs was found to be 54-78% using ICP-OES, which is the highest among all reported TaO$_x$ NPs to date (see Table 1). A protocol for complete digestion of the NCs using a mixture of hydrofluoric acid (HF) and nitric acid (HNO$_3$)

and consequent estimation of Ta content using a Varian ICP-OES system was developed (for further details, see "Ta Content Estimation Using ICP-OES" in Section 3 of the following "Additional Aspects of the Example" section). Of note, exact Ta content of previously described TaO$_x$ NPs have not been reported. The Ta content within multiple Ta$_2$O$_5$ NPs have been reported and varies between 30-41%, which is almost half of that reported in this example. With an optimal Ta content, the TaO$_x$ NCs described in this example possess a highly X-ray dense core and address an essential prerequisite of a pre-amplified CT CA. NC4 and NC5 are fluorescent versions of NC2 and NC3 with FITC-labeled surfaces, respectively, with XRD showing that these NCs are amorphous (see FIG. 23 for NC4 and FIG. 24 for NC5), TEM showing near identical diameter (see FIGS. 7G-7H and 25A-25C for NC4 and FIGS. 7I-7J and 26A-26C for NC5), EDS confirming the presence of Ta and Si (see FIGS. 27A-27D for NC4 and FIGS. 28A-28C for NC5), and XPS confirming the electronic state of Ta (see FIG. 29 for NC4 and FIG. 30 for NC5); x≈1. Further characterization using FTIR (see FIGS. 31A-31D and 32A-32B for NC4 and FIGS. 33A-33B and 34A-34D for NC5) confirm FITC-conjugation and the presence of various surface functionalities. Fluorescence spectra of FITC-labeled NC4 and NC5 suspended in PBS were in close agreement to that of free FITC (see FIG. 35).

TABLE 1

Characterization of various TaO$_x$ NCs:

| TaO$_x$ NC type | Ta (%)[a] | Diameter[b,c] (nm) | PDI[b] | Zeta Potential[b] (mv) |
|---|---|---|---|---|
| NC1 | 73 | (11.1 ± 0.7)[b] | 0.12 ± 0.05 | −12.1 ± 1.3 |
| NC2 | 78 | (12.9 ± 0.8)[b] | 0.17 ± 0.01 | −29.4 ± 5.9 |
| NC3 | 69 | (10.1 ± 0.4)[c] | n/a | n/a |
| NC3 | 61 | (17.2 ± 2.1)[b] | 0.14 ± 0.04 | −39.9 ± 3.1 |
| NC5 | 56 | (11.2 ± 1.8)[c] | n/a | n/a |

[a]Ta content reported using ICP-OES;
[b]Diameter, PDI and Zeta potential reported using DLS;
[c]Diameter reported using TEM images analyzed by Image J software.

Dissolution of TaO$_x$ NCs under lysosomal conditions: A primary concern regarding the clinical translation of NPs is the potential toxicity resultant from their dissolution in cells within lysosomes, exposing cells to metal ions. As injected or endocytosed NPs follow an intracellular transport pathway through endosomes to lysosomes, conditions such as low pH and presence of ligating anions such as citrates are typically encountered. In order to evaluate the stability of the NCs against dissolution under such conditions, an in vitro dissolution study was carried out in PBS (pH 7.4) and NaCit (pH 5.5) at 37° C. for a period of 4 weeks. Incubation in PBS mimics the cytosolic and extracellular pH; while NaCit (pH 5.5) mimics the post-endocytosis lysosome environment. The experimental details for this study are described in "In Vitro Ta Dissolution" in Section 3 of the following "Additional Aspects of the Example" section. Briefly, TaO$_x$ NC3 and TaO$_x$ NC5 were suspended in 1 mL each of PBS and NaCit at 37° C., and aliquots were withdrawn at regular time points for the entire period of the study (infinite sink conditions), analyzed for Ta content using ICP-OES, and normalized to obtain cumulative Ta release. The Ta release is plotted in FIGS. 36A-36B (see also, FIGS. 76A-76B) and shows low Ta dissolution for both the NC variants (less than 4%) in both PBS (see FIG. 36A) and NaCit (see FIG. 36B). The slow dissolution of various heavy metal NPs under neutral conditions is well-documented; however, the less than 3% overall Ta dissolution under lysosomal pH was surprising. This clearly demonstrates the inert nature of the TaO$_x$ NCs under cytosolic and lysosomal conditions.

In vitro viability and fluorescence imaging of FITC-labeled TaO$_x$ NCs: To evaluate the cytocompatibility of various TaO$_x$ NCs, MTT cell viability assays using RAW 264.7 macrophage cells and HEK 293 cells following 24 hours incubation with varied NC concentrations were carried out. NC1, NC2, and NC4 were selected as they were hydrophilic and formed stable suspensions in cell culture media. High cytocompatibility, up to 2.4 mg mL$^{-1}$ Ta, was measured for all three NC types in both cell lines (see FIGS. 37A-37B and Section 4 of the following "Additional Aspects of the Example" section), likely aided by the inertness and limited dissolution of the TaO$_x$ NCs. The high cell viability matches that of RITC-TaO$_x$ NPs previously reported.

Micro-CT imaging of TaO$_x$ NC1 phantoms in saline: To characterize the CT properties of TaO$_x$ NCs, samples of the highly hydrophilic TaO$_x$ NC1 (0-100 mM Ta) were dispersed in saline, and CT images were acquired on a Perkin Elmer Quantum GX micro-CT scanner operating at 90 kVp and 88 µA. The CT HUs showed a linear increase versus Ta concentration with 5.7 HU mM$^{-1}$ (see FIGS. 38A-38B and Section 5 of the following "Additional Aspects of the Example" section), which is almost identical to that of gadolinium- and iodine-based agents in other studies, but only at 90 kVp. At clinical kVp, especially above 100 kVp, Ta outperforms iodine in phantom studies.

In vivo CT imaging of TaO$_x$ NCs following IV injection: In vivo biodistribution of the highly hydrophilic TaO$_x$ NC1 was measured, and serial micro-CT imaging was performed over 72 hours in mice following intravenous injection of either 296 mg kg$^{-1}$ or 592 mg kg$^{-1}$ TaO$_x$ NC1, delivered in 200 µL, at 100 mM or 200 mM Ta concentration, respectively. Following IV injection, NC1 is visible in the vasculature and remains in circulation for at least 3 hours before final accumulation by the liver and spleen over a period of 24-72 hours (see FIG. 39). The HU values in the vasculature were maximal immediately post-injection and decreased over time, while that for the liver and the spleen increased gradually and peaked at 24 hours and 72 hours, respectively (see FIG. 40). The mice were healthy and did not show any adverse effects such as weight loss, loss of appetite, or abnormal behavior during the entirety of the study. Procedural details for the in vivo experiment are provided in Section 6 of the following "Additional Aspects of the Example" section.

In vivo biodistribution, histopathology and clinical chemistry of TaO$_x$ NCs: After 72 hours, the mice were sacrificed and various organs (heart, liver, kidney, and spleen) were collected and evaluated for biodistribution of the TaO$_x$ NC1. Sections of the heart, liver, kidney, and spleen were digested in a 4:1 mixture of HNO$_3$ and HF and evaluated for Ta content using ICP-OES. Maximal Ta content was observed in the liver and spleen (see FIGS. 41A-41B), consistent with the NC distribution and time-dependent CT enhancement as observed in FIG. 40. Detailed histological analysis at 72 hours of tissue sections excised from the liver, spleen, kidney, heart, and bladder showed no adverse effects in mice injected with 296 mg kg$^{-1}$ TaO$_x$ NC1, while mice injected with 592 mg kg$^{-1}$ TaO$_x$ NC1 had multiple hepatic and splenic insults, as shown by the arrows in FIG. 42. The liver and spleen necrosis observed from the histopathology from mice injected with 592 mg kg$^{-1}$ TaO$_x$ NC1 is corroborated with clinical pathology data that indicates higher ALT and AST activity, suggesting hepatocellular damage (see FIGS.

43A-43F). Clinical pathology data from mice injected with saline (control) or 296 mg kg$^{-1}$ TaO$_x$ NC1 showed no clinically significant differences. This compares favorably with the standard clinical iodine-based CT contrast agents, which generally deliver 240-370 mg kg$^{-1}$ iodine to patients. These results further suggest a safe upper limit of Ta concentration below 592 mg kg$^{-1}$ TaO$_x$ NC1.

Imaging the ductal tree in mammary glands following injection of TaO$_x$ NCs: The ability of TaO$_x$ NC1 to be administered locally and reveal in exquisite detail the continuous non-anastomosed branched structure of a murine ductal tree is demonstrated. Remarkably, ductal tree visualization in mice with TaO$_x$ NC1 is significantly superior to that with Isovue-300, an iodine-containing CA used in the clinic for diagnostic ductography. While Isovue-300 quickly diffuses out of the injected ductal tree immediately after injection, TaO$_x$ NC1 remains within the ductal tree for more than 5 days, enabling repeated imaging of the entire ductal tree network (see FIGS. 44A-44B). Moreover, the efficacy of intraductal injection of 70% EtOH in preventing tumor formation in an aggressive mouse model of breast cancer was recently shown. The addition of 60 mM TaO$_x$ NC1 in ethanol enabled the visualization of the filling of the entire ductal tree during treatment. TaO$_x$ NC1 could be used for clinical evaluation of this local ablation preventative therapy in high-risk individuals.

Design, Synthesis, and Characterization of Polymer Encapsulated TaO$_x$ NPs

Focused on next is the design of a NP CT contrast agent that has a core-shell structure, wherein multiple CT-dense NCs constitute the NP core, while FDA approved polymers such as PLGA or biocompatible alternatives, such as mesoporous silica, comprise the shell. This builds on well-established technology of encapsulating bismuth, iron oxide, gadolinium oxide, and several heavy metal NCs within PLGA or silica. The salient features of this methodology are 1) facile encapsulation of multiple highly radiopaque TaO$_x$ NCs in FDA approved and biocompatible polymers, 2) reproducible and easy scale up procedure, and 3) high encapsulation efficiency within the polymer matrix, resulting in higher per volume Ta content.

Design rationale and synthesis of TaO$_x$@PLGA NPs: Encapsulation of hydrophobic NCs in PLGA using an oil-in-water emulsification technique has been previously reported. An identical procedure was adopted to synthesize TaO$_x$@PLGA NPs, as shown in FIG. 45A. The technique generates an oil-in-water emulsion, wherein the hydrophobic TaO$_x$ NC3 and the polymer PLGA comprise the oil layer (DCM) and the water-soluble emulsifier and surfactant PVA comprises the water layer (see Section 7 of the following "Additional Aspects of the Example" section and FIGS. 45A and 45B). This procedure involves the initial dropwise addition of the oil in water over continuous vortex, followed by tip-sonication to generate an emulsion. The emulsion is diluted and stirred for 3 hours at RT to remove the low boiling point solvent DCM, resulting in hardened NPs. The critical step in this procedure is the formation of a homogenous suspension of the NCs and the polymer in the oil layer. As such, hydrophobic NCs are best when using this strategy. FITC-TaO$_x$@PLGA NPs, with the FITC-TaO$_x$ NC5 as the core, were also fabricated by simply replacing the hydrophobic TaO$_x$ NC3 with the fluorescently-labeled TaO$_x$ NC5 in the oil layer (DCM) (see FIG. 45B), allowing the cellular uptake and internalization of the NPs to be tracked by fluorescence microscopy. Importantly, the reaction steps were carried out in the dark to avoid photobleaching.

Characterization of TaO$_x$@PLGA NPs: Table 2 lists hydrodynamic size, polydispersity index (PDI), and zeta potential for all of the six TaO$_x$@PLGA NP types. The average size for the TaO$_x$@PLGA NPs and the FITC-TaO$_x$@PLGA NPs was approximately 210-230 nm, with a low PDI of 0.1-0.2. The terminal acid functionality in PLGA and the use of PVA as a stabilizer contributed towards the negative zeta potential observed for these NPs. SEM and TEM images (insets) for TaO$_x$@PLGA NPs (see FIGS. 46A-46B and 47A-47C) and FITC-TaO$_x$@PLGA NPs (see FIGS. 46C-46D and 48A-48C) revealed smooth spheres with efficient and uniform encapsulation of TaO$_x$ NCs and no visible aggregation. The presence of Ta and Si was confirmed using EDS spectra (see FIGS. 49A-49D for TaO$_x$@PLGA NPs and FIGS. 50A-50D for FITC-TaO$_x$@PLGA NPs). The fluorescence spectra of the FITC-TaO$_x$@PLGA NPs suspended in PBS matched closely with that of free FITC (see FIG. 51). The FTIR characterization of TaO$_x$@PLGA NPs (see FIGS. 52A-52D) and FITC-TaO$_x$@PLGA NPs (see FIGS. 53A-53D) indicates that the synthesis procedure neither altered the chemical composition of the PLGA polymer nor impacted the silane coating on the TaO$_x$ NCs embedded within the polymer shell. Common peaks include the sharp peak centered at 1760 cm$^{-1}$ corresponding to the C=O group in the starting polymer and identical distribution of peaks in the alkyl C—H bend range (1350-1480 cm$^{-1}$) and alkoxy C—O stretching range (1050-1150 cm$^{-1}$). Also buried within the broad peak centered at about 1100 cm$^{-1}$ is a strong band for Si—O—Si stretching vibration that proves the presence and retention of a silane coating on the TaO$_x$ NCs. The Ta content for the TaO$_x$@PLGA variants was found to be within 45-56% using ICP-OES, the highest among all reported TaO$_x$ NPs to date (see Table 2).

TABLE 2

Characterization of various TaO$_x$ NP formulation:

| NP Type | NC Type | Polymer Type | Ta (%)[a] | $D_h$[b] (nm) | PDI[b] | Zeta Potential[b] (mV) |
|---|---|---|---|---|---|---|
| TaO$_x$@PLGA | TaO$_x$ NC3 | PLGA-ACID | 56 | 217.0 ± 3.3 | 0.19 ± 0.04 | −20.05 ± 0.59 |
| FITC-TaO$_x$@PLGA | TaO$_x$ NC5 | PLGA-ACID | 45 | 226.5 ± 1.7 | 0.14 ± 0.08 | −12.23 ± 0.71 |
| MSNP | n/a | Silica | n/a | 226.5 ± 1.7 | 0.11 ± 0.03 | −27.5 ± 6.3 |
| TaO$_x$@MSNP-OH | TaO$_x$ NC2 | Silica | 43 | 86.9 ± 3.9 | 0.14 ± 0.03 | −15.2 ± 2.5 |
| TaO$_x$@MSNP-Phos | TaO$_x$ NC2 | Silica | 45 | 83.4 ± 2.7 | 0.17 ± 0.02 | −17.9 ± 3.9 |

TABLE 2-continued

Characterization of various TaO$_x$ NP formulation:

| NP Type | NC Type | Polymer Type | Ta (%)[a] | $D_h$[b] (nm) | PDI[b] | Zeta Potential[b] (mV) |
|---|---|---|---|---|---|---|
| FITC-TaO$_x$@MSNP | TaO$_x$ NC4 | Silica | 39 | 85.7 ± 5.4 | 0.19 ± 0.07 | −17.5 ± 2.3 |

[a]Ta content reported using ICP-OES;
[b]Size, PDI, and Zeta potential reported using DLS.

Design Rationale and Synthesis of TaO$_x$@MSNPs

MSNPs are versatile nanocarriers for various drugs, macromolecules, and imaging agents due to favorable properties such as tuneable pore size, facile surface functionalization, and a stimuli responsive mechanism for loading/release of cargo at the target site. The robust, template driven synthesis allows for in situ seeding or post-synthesis surface modification with CAs for MRI, PET, optical, and ultrasound imaging, as has been demonstrated by various recent examples. The high pore volume and surface area, extensive cargo loading capability, and bioavailability, along with the ability to co-localize Cas for various imaging modalities, can transform these materials with no inherent contrast, into diagnostic tools with potential applications in theranostics. To create CT-visible MSNPs, in situ encapsulation of radiopaque TaO$_x$ NCs within the MSNPs was performed.

Among the various types of MSNPs, MCM-41 (mobil crystalline materials or mobil composition of matter) have been widely explored for drug delivery due to their ease of synthesis and a high surface area that has immense potential for loading various agents of interest. Typically, the synthesis of MCM-41 involves a highly water soluble cationic surfactant, such as cetyltrimethylammonium bromide (CTAB) that acts as a template to facilitate the formation of MSNPs. The base-assisted sol-gel reaction to form the MSNPs is ensued by the addition of a silica precursor, e.g., TEOS, resulting in the formation of these hexagonal materials with a pore size within 2.5-6 nm. This reaction typically occurs at high temperature, and the MSNPs are recovered by centrifugation. In order to remove the trapped surfactant template, an acid-assisted dialysis procedure is carried out to isolate template-free porous MSNPs. The synthetic protocol to fabricate TaO$_x$-embedded MSNPs is shown in FIG. 54 and the full synthetic procedure is detailed in Section 9 of the following "Additional Aspects of the Example" section. The use of water as the reaction solvent and the remaining steps suggest that any hydrophilic NC precursor could be easily incorporated within the MSNPs. The moderately hydrophilic TaO$_x$ NC2 was selected to be the MSNP core, as this had the highest Ta content of the hydrophilic TaO$_x$ NC variants synthesized. Briefly, to a pre-formed solution containing CTAB and TEA (base) in water, an aqueous suspension of TaO$_x$ NC2 was added, and the resulting suspension was heated to 80° C. for 1 hour. This step leads to the formation of ellipsoidal micelles with an inner core comprising a hydrophobic tail. The consequent addition of the oil-like monomer TEOS under vigorous stirring leads to the formation of an emulsion-like system. Subsequently, the reaction mixture is heated at 80° C. for 2 hours, during which the TEOS is solubilized on the hydrophobic core, resulting in micelle enlargement and a shape change from an ellipsoid to a sphere. As TEOS is hydrolyzed, positively charged, hydrophilic TEOS monomers are released into the aqueous media and to the negatively charged CTAB micelles, leading to formation of a silica shell around it.

Once the hydrolysis of TEOS is complete, the micelles decrease in size, agglomerating with nearby micelles to undergo NP growth with a mesoporous structure. Subsequent centrifugation and acid-mediated dialysis of the crude reaction mixture against water leads to isolation of TaO$_x$-embedded MSNPs. Synthesis of empty MSNPs simply omits the NCs during MSNP synthesis and is detailed in FIG. 55.

To enhance the dispersibility of the MSNPs in aqueous media, the inherent reactivity of the surface siloxane groups was employed. For example, introduction of PEG-Silane after the addition of TEOS led to the formation of TaO$_x$@MSNP-OH, which comprises surface-appended hydroxyl groups (see FIG. 56). Alternately, the addition of Phospha-Silane, a commercially available silane moiety with a phosphonate end group, resulted in the synthesis of TaO$_x$@MSNP-Phos, bearing phosphonate groups on the surface (see FIG. 57). The current methodology provides quick access to a range of functionalities that can be appended on the MSNP surface using well-established silane chemistry. A "ring opening click" reaction using various heterocyclic silanes to react with the surface hydroxyl groups of porous silica nanostructures and introduce functional groups, such as —NH$_2$ and —SH, for subsequent coupling with targeting or biocompatibility agents has been reported. Such reactions could easily be extended to the family of TaO$_x$@MSNPs, providing access to nanomaterials with a range of applications in targeted drug delivery and imaging. To further demonstrate the utility of the methodology in terms of its ability to encapsulate various types of NCs, as well as to track the cellular uptake and internalization of the resulting NPs, FITC-TaO$_x$@MSNPs comprising the fluorescent and hydrophilic FITC-labeled TaO$_x$ NC4 as the core were also fabricated by using a similar protocol. The respective reaction sequence is shown in FIG. 54 and is further detailed in FIG. 58 and in "Synthesis of MSNPs Embedded with FITC-TaO$_x$ NC4 (FITC-TaO$_x$@MSNP)" in Section 9 of the following "Additional Aspects of the Example" section.

Characterization of TaO$_x$@MSNPs: The three types of TaO$_x$@MSNPs and empty MSNPs were extensively characterized similarly as was done for the PLGA particles. All four MSNP variants formed stable suspensions in water, with Table 2 listing hydrodynamic size and zeta potential. The average size of the empty MSNPs was approximately 120-140 nm, with a PDI within 0.10-0.15. TaO$_x$@MSNPs had a decrease in average size to 85-90 nm, with a consequent increase in PDI within 0.15-0.20. As observed for the TaO$_x$@MSNP-OH particles, crude NPs prior to removal of the CTAB template registered a wide PDI within 0.3-0.4 and a smaller hydrodynamic size of 40-45 nm. On removal of CTAB and further purification using dialysis, the NP size increased to 85-90 nm, with a narrow PDI of 0.15-0.20. This trend was observed across all the three MSNP types and suggests that the removal of CTAB leads to enlargement of pores in solution that results in NP swelling and consequent increase in hydrodynamic size. There were also stark differences in the zeta potentials of the raw and clean MSNPs. For raw MSNPs, a positive zeta potential of +35 mV was noted; however, the removal of CTAB shifted the zeta potential to −27 mV. The change in zeta potential was in accordance with the alteration in surface functional groups; the presence of a positively charged ammonium bromide tail within the CTAB moiety results in positive zeta potential for raw MSNPs, whereas removal of CTAB and the presence of —OH and the phosphonate surface groups lead to negative zeta potential. The SEM and TEM (inset) characterization for all four MSNP variants showed a homogenous spherical morphology (see FIGS. 59A-59C for empty MSNPs, FIGS. 60A-60B and 61A-61C for $TaO_x$@MSNP-OH, FIGS. 60C-60D and FIGS. 62A-62C for $TaO_x$@MSNP-Phos, and FIGS. 60E-60F and FIGS. 63A-63C for FITC-$TaO_x$@MSNP) with no apparent agglomeration. The TEM images of the MSNPs offer a closer look at the intricate network of the pores within the MSNPs. For the various $TaO_x$@MSNP types, encapsulation of individual $TaO_x$ NCs within the MSNP core was clearly visible in the TEM images. It is evident upon close inspection of the NPs that the $TaO_x$ NCs acted as a core seed for the generation of a mesoporous structure around it.

Encapsulation of iron oxide, gadolinium oxide, and gold NPs within MSNPs has also been reported; however, most of these NCs are hydrophobic and require aqueous phase transfer prior to encapsulation. This strategy was initially attempted, and the phase transfer of hydrophobic NCs was carried out by heating a solution of the NCs in chloroform with a solution of CTAB in water at the boiling point of the organic phase. However, this procedure was not efficient, as incomplete phase transfer of the NCs was observed, leading to low yields and poor encapsulation within the MSNPs. The use of a partially hydrophilic $TaO_x$ NC2, as described in this example, allowed for the circumvention of the need for phase transfer, resulting in efficient encapsulation of the $TaO_x$ NCs in the MSNP matrix. Further, any excess, non-encapsulated $TaO_x$ NCs could easily be recovered during the purification step, as the MSNPs were isolated as a residue during centrifugation, leaving behind the excess NCs in the aqueous wash layer, which can be subsequently recovered following a simple dialysis step.

The EDS spectra for all MSNP types confirm the presence of Ta, Si, and P (see FIGS. 64A-64B for empty MSNPs, FIGS. 65A-65D for $TaO_x$@MSNP-OH, FIGS. 66A-66C for $TaO_x$@MSNP-Phos, and FIGS. 67A-67D for FITC-$TaO_x$@MSNP). The fluorescence spectra of the FITC-$TaO_x$@MSNP suspended in PBS matches closely with that of free FITC (see FIG. 68). The silane composition of the MSNPs, as well as the various surface chemistries, were verified by FTIR (see FIG. 69 for empty MSNPs, FIGS. 70A-70D for $TaO_x$@MSNP-OH, FIGS. 71A-71D for $TaO_x$@MSNP-Phos, and FIGS. 72A-72C for FITC-$TaO_x$@MSNP). The FTIR spectra of empty MSNPs and the three $TaO_x$@MSNP variants show the presence of Si—O—Si stretching vibration, evident by a strong and broad band at 1096 cm$^{-1}$. This band is akin to the network of Si—O—Si bonds that are fundamental to the MSNP structure (see FIGS. 69, 70A-70D, 71A-71D, and 72A-72C). Masked within that broad peak lies the sharp band at 1100 cm$^{-1}$; representative of the Si—O—Si stretching vibrations due to the PEG-Silane coating on the $TaO_x$ NCs. In addition, the characteristic P=O stretching for the Phospha-Silane precursor, at 1233 cm$^{-1}$ appears as a small, shoulder band masked by the broad Si—O—Si band for both the $TaO_x$@MSNP-Phos (see FIGS. 71A-71D) and FITC-$TaO_x$@MSNP (see FIGS. 72A-72C). A close inspection of the FTIR spectra of various $TaO_x$@MSNP variants also reveals peaks that are representative of various surface functional groups, such as a network of H-bonded hydroxyl groups (broad bands at 3300-3400 cm$^{-1}$). Further, the repeating PEG units (broad band at approximately 1100 cm$^{-1}$, superimposed with the asymmetric C—O—C stretching of the repeating —O—CH$_2$—O—CH$_2$—O— groups) and amine groups (IR peaks at approximately 1634 cm$^{-1}$, corresponding to the N—H bend) are also representative of varied surface functionalities. The $TaO_x$ NCs embedded within the MSNPs resulted in high (39-45%) Ta content, with the highest Ta content observed for $TaO_x$@MSNP-Phos NPs (see Table 2).

Dissolution of $TaO_x$ NPs under lysosomal conditions: The dissolution of various $TaO_x$ NP formulations under lysosomal and cytosolic conditions were evaluated similarly as described above for NCs (further detailed in Section 11 of the following "Additional Aspects of the Example" section). The Ta dissolution for both the NP variants at pH 7.4 was low (less than 3.5%) when compared to $TaO_x$ NCs. Similarly, low dissolution (less than 4%) was measured at pH 5.5 over the four weeks study period as shown in FIGS. 73A-73B. The low Ta dissolution can be traced back to the inert nature of the $TaO_x$ NCs that is not compromised during the encapsulation procedure.

In vitro viability and cell labeling by FITC-labeled $TaO_x$ NPs: To evaluate the cytocompatibility of various $TaO_x$ NPs, MTT colorimetric cell viability assays were carried out using RAW 264.7 macrophage cells and HEK 293 cells, following 24 hours incubation with varied NP concentrations (see Section 12 of the following "Additional Aspects of the Example" section). Two types of NPs, $TaO_x$@PLGA NPs and $TaO_x$@MSNP-OH, were selected as representative examples. Similar to $TaO_x$ NCs, high cytocompatibility, up to 1.2 mg mL$^{-1}$ Ta, was measured in both cell lines (see FIGS. 74A-74B).

In vivo CT imaging of $TaO_x$ NPs: To evaluate their CT potential in an in vivo setting mimicking the accumulation of NPs in a site such as a tumor, a series of experiments were performed where two concentrations of $TaO_x$@PLGA NPs and $TaO_x$@MSNP-Phos were injected intramuscular (IM) as a single bolus bilaterally in the right and left leg muscle in BALB/c mice (see Section 13 of the following "Additional Aspects of the Example" section). Concentrations of each NP were 27.4 mg kg$^{-1}$ in saline (50 mM Ta) or 13.7 mg kg$^{-1}$ in saline (25 mM Ta) for $TaO_x$@PLGA NPs and 36.8 mg kg$^{-1}$ in saline (50 mM Ta) or 18.4 mg kg$^{-1}$ in saline (25 mM Ta) for $TaO_x$@MSNP-Phos. Following IM injection of equimolar concentrations of $TaO_x$@PLGA NPs and $TaO_x$@MSNP-Phos, equivalent contrast enhancement is observed at the injection sites for each NP (see FIG. 75A). Different concentrations of both NP types (25 and 50 mM Ta in saline) were also injected IM as single, bolus injections bilaterally in the left and right leg, respectively (one male BALB/c mouse per NP formulation). On CT, the concentration variation at the site of injection is evident for both $TaO_x$@PLGA NPs (see FIG. 75B) and $TaO_x$@MSNP-Phos NPs (see FIG. 75C). To highlight the concentration difference, the CT images are color coded (see FIGS. 75A-75C; purple=25-mM Ta and blue=50 mM). The intelligent design and facile synthesis of the $TaO_x$-embedded NPs using inexpensive, readily available, and FDA-approved biocompatible materials serves as a stepping stone towards the development of CT Cas for dual energy and multi-color CT.

CONCLUSIONS

In summary, hydrophilic and hydrophobic fluorescently-labeled $TaO_x$ NCs with the highest Ta content reported to date have been demonstrated. Cells maintain high in vitro cell viability (up to 2.4 mg Ta mL$^{-1}$) and exhibit inconsequential Ta dissolution under both cytosolic and lysosomal conditions. Extremely hydrophilic TaO$_x$ NC1 produced high in vivo CT contrast in the vasculature following IV injection, with a prolonged blood circulation time and no significant toxicity measured for the 100 mM Ta dose. Intraductal injection into the mammary pads of TaO$_x$ NC1 provides unprecedented in vivo imaging of ductal trees in rodents. Next, TaO$_x$ NCs were successfully encapsulated within PLGA and MSNPs to form TaO$_x$@PLGA NPs and TaO$_x$@MSNPs, respectively. These NP formulations had high Ta content, and cells incubated with these NPs maintained high in vitro cell viability (up to 1.2 mg Ta mL$^{-1}$) and limited Ta dissolution. Both TaO$_x$@PLGA NPs and TaO$_x$@MSNPs produced effective CT contrast following a locally administered IM bolus in mice, mimicking the accumulation of such materials for drug delivery in a tumor, for example. The encapsulation of individual TaO$_x$ NCs in biocompatible and FDA-approved polymers detailed in this example results in NPs that can be used as versatile CAs for molecular imaging by CT.

Additional Aspects of the Example

Section 1. Synthetic Details for TaO$_x$ NCs:
General Information.

All reactions, unless otherwise stated, were performed with oven-dry glassware. All other reagents and solvents were obtained from commercial suppliers and used without further purification. Centrifugation to isolate NCs were performed on a Sorvall LYNX 4000 Superspeed centrifuge.
Synthesis of TaO$_x$ NCs Typical procedure (see FIG. 4A): In a 250 mL one neck round bottom flask fitted with a septa, IGEPAL®-CO-520 (poly(oxyethylene)nonylphenyl ether; average M$_n$ 441, ALDRICH, 23.0 g), cyclohexane (≥99%, ACS spectrophotometric grade, SIGMA-ALDRICH, 200 mL), and ethanol (200 proof, anhydrous, KOPTEC USP, 2.5 mL) were added and the contents were stirred to obtain a clear solution. To this stirring mixture, a solution of sodium hydroxide (100 mM, 2.5 mL) was added, and the micro-emulsion so obtained was sonicated in a water bath to ensure homogeneity. Next, Ta$_2$O$_5$ (99.98% trace metal basis, ALDRICH, 0.5 mL) was added in one portion and the contents so obtained were stirred at ambient temperature for 20 minutes. On addition of Ta$_2$O$_5$, the otherwise clear solution gave way to slight turbidity, indicating the formation of uncoated NCs. At this stage of the reaction, different silane end group reactants were added to form NCs with varying degree of hydrophilicity/hydrophobicity or to append fluorescent tags to the NC surface, as per requirement.
Synthesis of Extremely Hydrophilic TaO$_x$ NCs (TaO$_x$ NC1)

See the pathway leading to the generation of TaO$_x$ NC1 in FIGS. 4A and 4B. To the micro-emulsion mixture containing uncoated TaO$_x$ NCs, PEG-Silane (tech-90, MW 591-723, GELEST INC., 3.0 mL), quickly followed by APTMS (97%, ALDRICH, 0.028 mL) were added. The resulting milky white suspension solution was stirred at RT for 16 hours. The addition of reactants with silane end groups ensures a condensation reaction with the hydroxyl groups on the bare surface of TaO$_x$ NCs and ensures a protective coating around it so that a well-dispersed collection of NCs is obtained. On absence of any PEG-Silane, agglomerated NCs are obtained (see FIGS. 5A-5C). After 16 hours, the reaction mixture is diluted to three times volume using a 1:1 mixture of ethyl ether (anhydrous, Certified ACS, Fisher Scientific, 110 mL) and hexane (meets ACS specifications, VWR Chemicals, 110 mL), and the NCs were isolated via centrifugation (15,000 rpm, 10 minutes, 10° C.) as white oily residue. This residue was suspended in ethyl ether and washed using a similar centrifugation procedure twice. The supernatants were discarded and the residue pellet so obtained was suspended in 100 mL ethanol, and methoxy-poly(ethyleneglycol)-succinimidyl glutarate (m-PEG-SG-2000, Average MW 2000, LAYSAN BIO INC., 50 mg) was added to it.

The contents so obtained were stirred at RT in dark for 16 hours. After the aforementioned time, the solvent was removed on a rotary evaporator to reduce the volume to about 5 mL. This final residual solution was dissolved in water (10 mL) and transferred to dialysis membrane bags (SPECTRA/POR® 3 Dialysis Membrane, Standard RC Tubing, MWCO: 3.5 kD), clipped at both ends, and dialyzed against water, with regular change of external media after 2, 4, 16, 4, 4, and 16 hours. After extensive dialysis, the contents in the dialysis bags were lyophilized to obtain the TaO$_x$ NC1 as a white fluffy powder. Product Yield: 940 mg. Ta %=73% (calculated from ICP-OES).
Synthesis of Moderately Hydrophilic TaO$_x$ NCs (TaO$_x$ NC2)

Figure 4C:
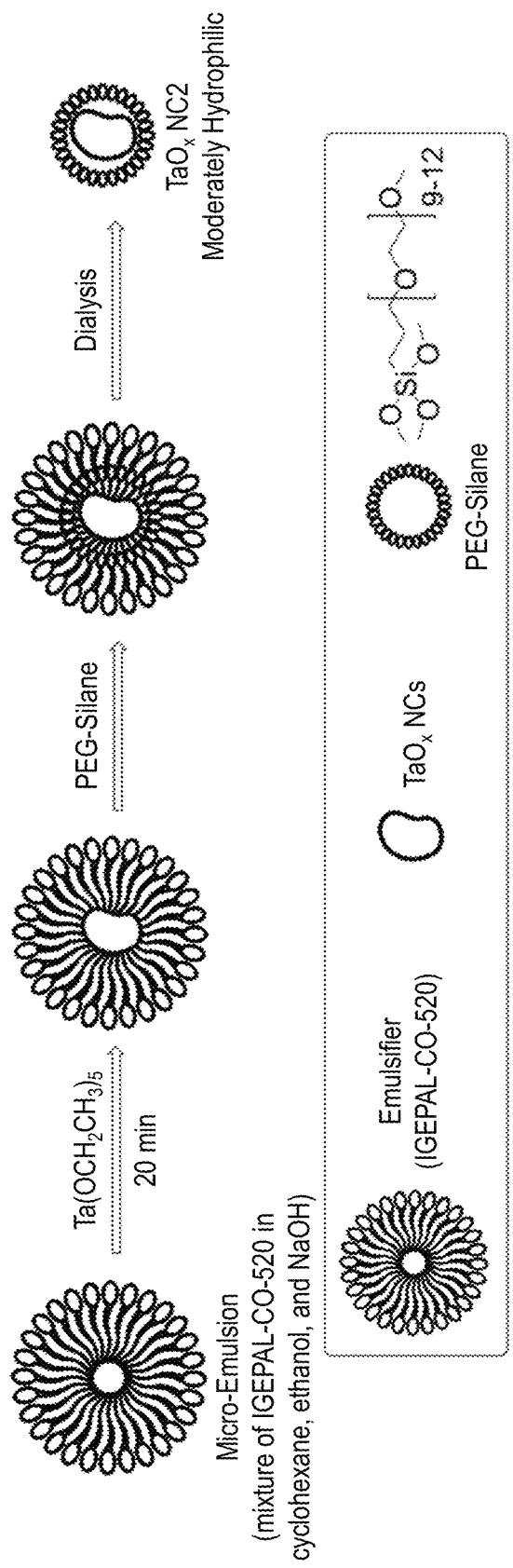
Figure 4D:
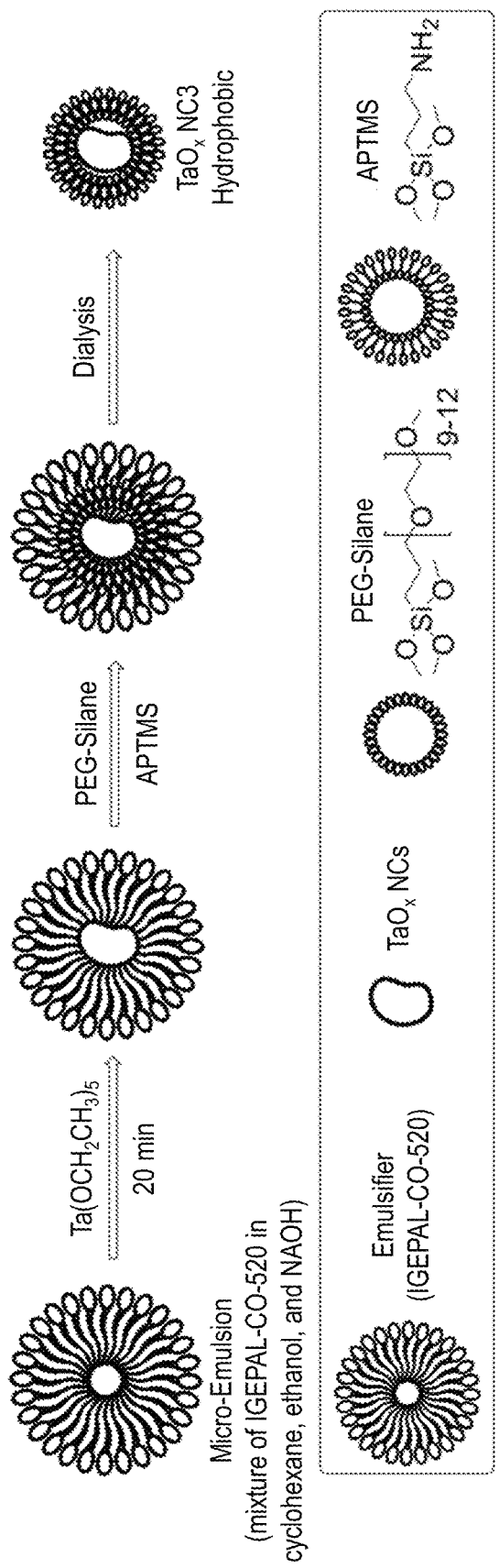

See the pathway leading to the generation of TaO$_x$ NC2 in FIGS. 4A and 4C. To the micro-emulsion mixture containing uncoated TaO$_x$ NCs, PEG-Silane (tech-90, MW 591-723, GELEST INC., 3.0 mL) was added. The resulting milky white suspension solution was stirred at RT for 16 hours. After 16 hours, the reaction mixture is diluted to three times volume using a 1:1 mixture of ethyl ether (anhydrous, Certified ACS, Fisher Scientific, 110 mL) and hexane (meets ACS specifications, VWR Chemicals, 110 mL), and the NCs were isolated via centrifugation (15,000 rpm, 10 minutes, 10° C.) as white oily residue. The residual oily pellet was dissolved in water (10 mL) and transferred to dialysis membrane bags (SPECTRA/POR® 4 Dialysis Membrane, Standard RC Tubing, MWCO: 12-14 kD), clipped at both ends, and dialyzed against water with regular change of external media after 2, 4, 16, 4, 4, and 16 hours. After extensive dialysis, the contents in the dialysis bags were lyophilized to obtain the TaO$_x$ NC2 as a white sticky powder. Product Yield: 840 mg. Ta %=78% (calculated from ICP-OES).
Synthesis of Hydrophobic TaO$_x$ NCs (TaO$_x$ NC3)

See the pathway leading to the generation of TaO$_x$ NC3 in FIGS. 4A and 4D. To the micro-emulsion mixture containing uncoated TaO$_x$ NCs, PEG-Silane (tech-90, MW 591-723, GELEST INC., 1.0 mL) followed by APTMS (97%, ALDRICH, 6.0 mL) were added in rapid succession. The resulting milky white suspension solution was stirred at RT for 16 hours. After 16 hours, the reaction mixture is diluted to three times volume using a 1:1 mixture of ethyl ether (anhydrous, Certified ACS, Fisher Scientific, 110 mL) and hexane (meets ACS specifications, VWR Chemicals, 110 mL), and the NCs were isolated via centrifugation (15,000 rpm, 10 minutes, 10° C.) as white oily residue. This residue was suspended in ethyl ether and washed using a similar centrifugation procedure twice. This residual oily pellet was dissolved in water (10 mL) and transferred to dialysis membrane bags (SPECTRA/POR® 4 Dialysis Membrane, Standard RC Tubing, MWCO: 12-14 kD), clipped at both ends, and dialyzed against water with regular change of external media after 2, 4, 16, 4, 4, and 16 hours. After extensive dialysis, the contents in the dialysis bags were lyophilized to obtain the TaO$_x$ NC3 as a white free flowing powder. Product Yield: 900 mg. Ta %=69% (calculated from ICP-OES).

Synthesis of Fluorescently-Labeled $TaO_x$ NCs

Typical procedure (see FIGS. 4A, 4E, and 4F): In a 4 dram vial, FITC (Isomer I, ≥90%, SIGMA, 20.0 mg) and APTMS (97%, ALDRICH, 0.040 mL) were taken, and ethanol (200 proof, anhydrous, KOPTEC USP, 10.0 mL) was added to it. This reaction mixture was stirred at RT in the dark for 12 hours. Separately, in a 250 ml one neck round bottom flask fitted with a septa, IGEPAL®—CO-520 (average $M_n$ 441, ALDRICH, 23.0 g), cyclohexane (≥99%, ACS spectrophotometric grade, SIGMA-ALDRICH, 200 mL), and ethanol (200 proof, anhydrous, KOPTEC USP, 2.5 mL) were added, and the contents were stirred to obtain a clear solution. To this stirring mixture, a solution of sodium hydroxide (100 mM, 2.5 mL) was added, and the micro-emulsion so obtained was sonicated in a water bath to ensure homogeneity. Next, $Ta_2O_5$ (99.98% trace metal basis, ALDRICH, 0.5 mL) was added in one portion, and the contents so obtained were stirred at ambient temperature for 20 minutes. On addition of $Ta_2O_5$, the otherwise clear solution gave way to slight turbidity, indicating the formation of uncoated NCs. At this stage of the reaction, different silane end group reactants were added to form NCs with varying degree of hydrophilicity/hydrophobicity or to append fluorescent tags to the NC surface, as per requirement.

Synthesis of FITC-Labeled Hydrophilic $TaO_x$ NCs (FITC-$TaO_x$ NC4)

Figure 4E:
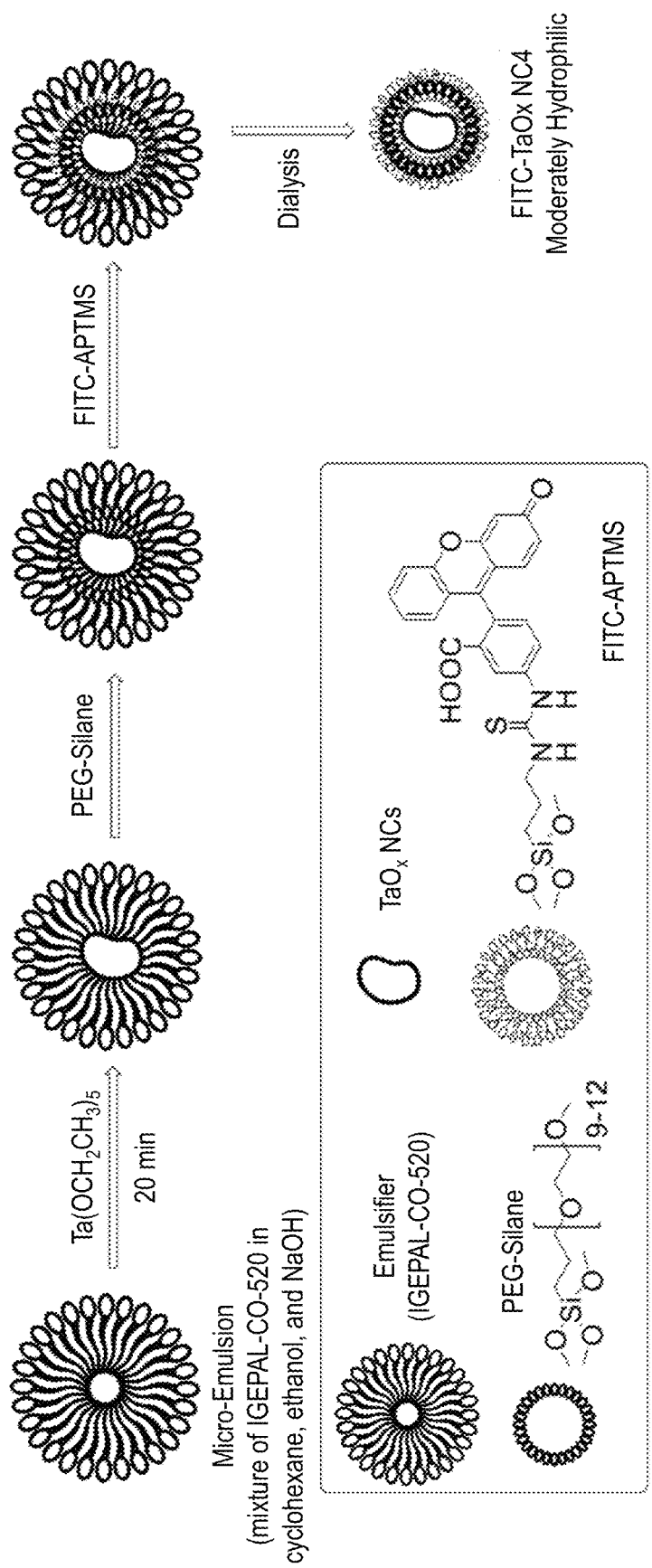
Figure 5A:
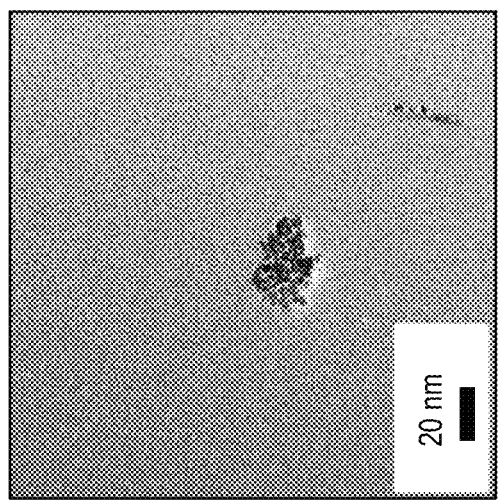
FIGS. 5A-5C are transmission electron microscopy (TEM) images of bare $TaO_x$ NCs prepared without addition of any surface coating PEG-Silane in accordance with various aspects of the current technology. The agglomeration of NCs is very evident.
Figure 5B:
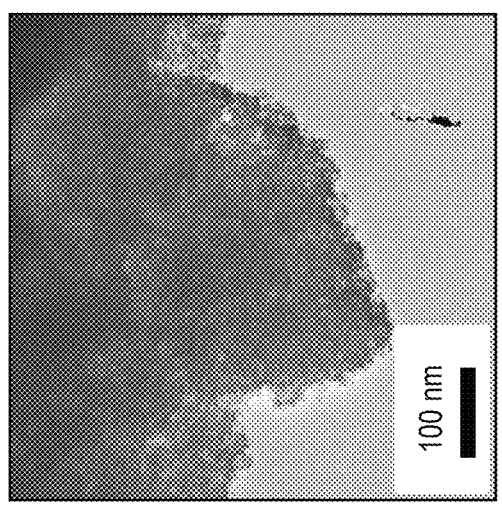
Figure 5C:
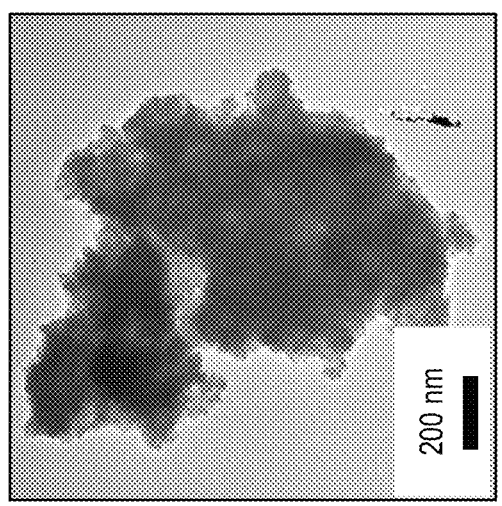

See the pathway leading to the generation of FITC-$TaO_x$ NC4 in FIGS. 4A and 4E. To the micro-emulsion mixture containing uncoated $TaO_x$ NCs, PEG-Silane (tech-90, MW 591-723, GELEST INC., 3.0 mL) followed by the mixture of APTMS-FITC prepared beforehand were added to it in quick succession. The resulting yellow colored suspension solution was stirred at RT for 16 hours in the dark. After 16 hours, the reaction mixture is diluted to three times volume using a 1:1 mixture of ethyl ether (anhydrous, Certified ACS, Fisher Scientific, 110 mL) and hexane (meets ACS specifications, VWR Chemicals, 110 mL), and the NCs were isolated via centrifugation (15,000 rpm, 10 minutes, 10° C.) as a yellow colored oily residue. The residual oily pellet was dissolved in water (10 mL) and transferred to dialysis membrane bags (SPECTRA/POR® 4 Dialysis Membrane, Standard RC Tubing, MWCO: 12-14 kD), clipped at both ends, and dialyzed against water with regular change of external media after 2, 4, 16, 4, 4, and 16 hours. After extensive dialysis, the contents in the dialysis bags were lyophilized to obtain the FITC-$TaO_x$ NC4 as a yellow-orange colored sticky powder. Product Yield: 800 mg. Ta %=61% (calculated from ICP-OES).

Synthesis of FITC-Labeled Hydrophobic $TaO_x$ NCs (FITC-$TaO_x$ NC5)

Figure 4F:
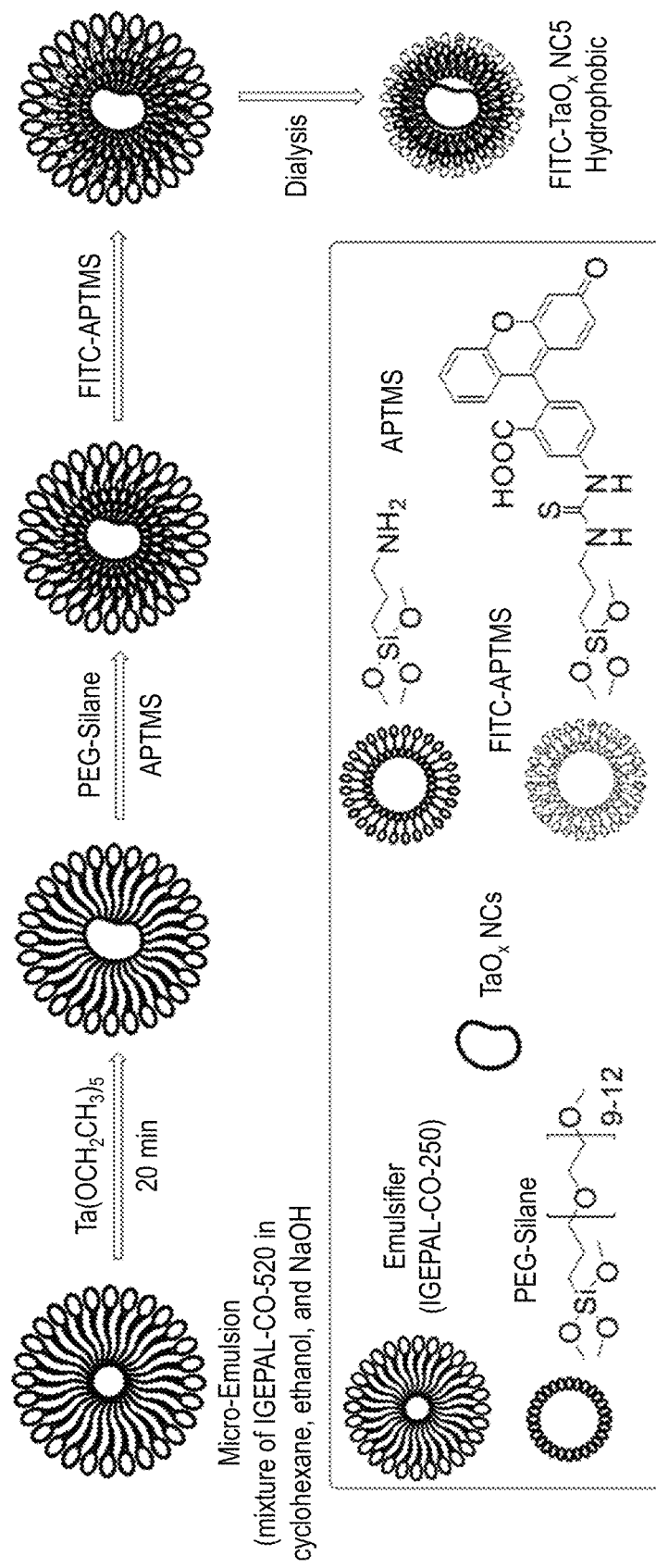

See the pathway leading to the generation of FITC-$TaO_x$ NC5 in FIGS. 4A and 4F. To the micro-emulsion mixture containing uncoated $TaO_x$ NCs, PEG-Silane (tech-90, MW 591-723, GELEST INC., 3.0 mL), APTMS (97%, ALDRICH, 6.0 mL), and the mixture of APTMS-FITC prepared beforehand were added in quick succession. The resulting yellow colored suspension solution was stirred at RT for 16 hours in the dark. After 16 hours, the reaction mixture was diluted to three times volume using a 1:1 mixture of ethyl ether (anhydrous, Certified ACS, Fisher Scientific, 110 mL) and hexane (meets ACS specifications, VWR Chemicals, 110 mL), and the NCs were isolated via centrifugation (15,000 rpm, 10 minutes, 10° C.) as yellow oily residue. The residual oily pellet was dissolved in water (10 mL) and transferred to dialysis membrane bags (SPECTRA/POR® 4 Dialysis Membrane, Standard RC Tubing, MWCO: 12-14 kD), clipped at both ends, and dialyzed against water with regular change of external media after 2, 4, 16, 4, 4, and 16 hours. After extensive dialysis, the contents in the dialysis bags were lyophilized to obtain the FITC-$TaO_x$ NC5 as a yellow-orange colored free flowing powder. Product Yield: 740 mg. Ta %=56% (calculated from ICP-OES).

Section 2. Characterization Details for $TaO_x$ NCs:

General Information—Physicochemical Characterization (for NCs and NPs)

The $TaO_x$ NCs and NPs were characterized using a variety of techniques. The surface morphology was determined using SEM (JEOL 7500F with a cold field emission emitter). For the $TaO_x$-doped MCS, surface morphology was determined by SEM carried out using a Hitachi S-3500N, operating at 20 keV and a working distance of 10 mm. Encapsulation of $TaO_x$ NCs within PLGA and mesoporous silica was observed using TEM (JEOL, 2200FS, JEOL, USA). The size of the hydrophobic $TaO_x$ NCs was determined by analyzing corresponding TEM images using Image J software. For each batch, 200 NCs were analyzed in triplicates, with images taken from different portions of a TEM grid. For hydrophilic $TaO_x$ NCs and $TaO_x$ NP formulations, hydrodynamic radii ($D_h$, nm), PDI, and zeta potential ((, mV) were determined using DLS carried out on a Zetasizer instrument (Malvern, USA). FTIR spectroscopy was performed on a Mattson Genesis 3025 FTIR spectrometer. FTIR was used to verify the surface coating of silyl groups and PEG chains on the $TaO_x$ NCs, as well as to ascertain the presence of PLGA, silica, and FITC in the different $TaO_x$ NP formulations. EDS (TEM-EDS, JEOL, 2200 FS, JEOL, USA) was used to confirm the presence of Ta and Si in the NPs. For EDS, INCA software program was employed to carry out analysis of samples prepared on a TEM grid. BET surface area and porosity analysis was performed on an ASAP 2020 Accelerated Surface Area and Porosimetry System (Micromeritics, USA). For the MCS, white light interferometry was conducted on dry 1 $cm^2$ sample, using a Zygo New View 5000. The microstructure was imaged at 640×640 $\mu m^2$ area, showing a rough surface indicative of a porous structure. To determine the molecular state of $TaO_x$, XPS of the NCs was performed using a Perkin Elmer Phi 5600 ESCA system with a Mg Kα X-ray source at a take-off angle of 45°. ICP-OES was performed to analyze the Ta content in various NCs and NP formulations.

Sample preparation for TEM and EDS: To carry out TEM analysis, square mesh carbon support film on copper grids (CF300-Cu, 300 mesh, standard thickness, Electron Microscopy Sciences, USA) were used. For hydrophobic NCs, a homogenous, semi-transparent suspension in hexane was prepared, and 10 µL was dropped on the grid. The suspension was allowed to stand for 2 minutes to allow for the crystals to settle down, following which the residual solvent was blown off and the grid was air dried prior to imaging on the electron microscope. For NPs and hydrophilic NCs, a homogenous aqueous suspension was prepared and 10 µL was gently placed on the grid. The particles were allowed to settle down over a period of 30 minutes, and the residual aqueous drop was absorbed using a kimwipe. The resulting grid was air dried prior to imaging.

Sample preparation for SEM: For SEM analysis, freeze-dried NPs were mounted on aluminum stubs using high vacuum carbon tabs. The solid samples were placed on the carbon-tabbed aluminum stubs and pressed lightly using a spatula to seat the particles. The stubs were gently tapped to remove any loose particles, thus forming a thin uniform layer of particles. For the liquid samples, NP dispersions were placed on 10 mm×10 mm silicon wafers attached on top of aluminum stubs. The solution was then allowed to dry in air. Finally, both types of sample stubs were coated with iridium with an approximate thickness of 2.7 nm. This coating was performed in a Quorum Technologies/Electron Microscopy Sciences Q150T turbo pumped sputter coater (Quorum Technologies, Laughton, East Sussex, England BN8 6BN) purged with argon. Finally, these sample stubs were dried in vacuum for 48 hours prior to imaging. For the $TaO_x$-doped MCS, hydrated scaffolds were frozen in liquid nitrogen and sectioned with a razor blade before being placed on an aluminum stub. All samples were sputter coated with gold for 4 minutes at 40 mA and imaged subsequently.

Sample preparation for FTIR: For FTIR analysis, 1 mg of the solid sample was mixed with 150 mg of dry potassium bromide (KBr, Uvasol®, Millipore Sigma) and crushed to a fine powder using a mortar pestle. About 100 mg of the ground mixture was made into a transparent or translucent disc using a die assembly and a hydraulic press. The disc so obtained was transferred to a sample holder and analyzed for signals in the IR spectrum range. For samples that were in liquid state or as an oil, a diluted sample was prepared in chloroform as the solvent. A drop of this solution was put on a sodium chloride disc for analysis in the IR spectrum range.

Explanation of peaks observed in FTIR for $TaO_x$ NCs: Typically, silanes are characterized by one or more strong infrared bands in the region of 1300-1000 cm$^{-1}$, corresponding to the Si—O—Si stretching vibration. The presence of a silane coating on all the $TaO_x$ NC variants was evident from strong IR bands centered at 1100 cm$^{-1}$. FTIR spectra of various $TaO_x$ NCs also contain peaks that are in concordance with various surface functional groups, such as a network of H-bonded hydroxyl groups (broad bands centered at 3380 cm$^{-1}$), repeating PEG units (broad band centered about 1100 cm$^{-1}$, corresponding to the asymmetric C—O—C stretching of the repeating —O—CH2-O—CH2-O— groups; superimposed with the Si—O—Si stretching vibration) and amine groups (IR peaks centered at 1634 cm$^{-1}$, corresponding to the N—H bend).

Section 3. Estimation of Ta Content and Ta Dissolution from $TaO_x$ NCs:

TA Content Estimation Using ICP-OES

To estimate the Ta content in various $TaO_x$ NCs, each dry sample was analyzed using ICP-OES. For each sample, weighed portions (about 5 mg) of various $TaO_x$ NCs were suspended in a 4:1 mixture of $HNO_3$ (concentrated, 69%) and HF (concentrated, 48%). The resulting solution was stored at RT until complete dissolution was observed. Once a clear and transparent solution with no visible debris was obtained, the solutions were diluted to a final concentration of 2% $HNO_3$ and 0.01% HF to prepare samples that were directly analyzed for Ta content using ICP-OES using a Varian 710-ES, ICP-OES instrument. All measurements were carried out in triplicates, and the mean concentrations have been reported.

In Vitro Ta Dissolution

To analyze the dissolution of various $TaO_x$ NCs in lysosomal media, an in vitro dissolution study was carried out. In a typical experimental set-up, 5 mg of each variety of NCs were taken in separate 1.8 mL centrifuge vials and suspended separately in 1 mL each of PBS (pH 7.4) and NaCit (50 mM, pH 5.5). The resulting suspensions were transferred to a rotor maintained in an oven at 37° C. After various time points (1 hour, 4 hours, 20 hours, 24 hours, 48 hours, 3 days, 4 days, 5 days, 7 days, 8 days, 9 days, 10 days, 11 days, 14 days, 21 days, and 28 days), the tubes were centrifuged and the supernatant was collected. The residue were re-suspended in the respective media, and the experiment was continued. After 4 weeks, the supernatant liquid was evaporated and the residue so obtained was digested by adding 0.8 mL concentrated $HNO_3$ (69%) and 0.2 mL concentrated HF (48%) and leaving the suspension so obtained until a clear yellow solution was obtained (48 hours).

After 48 hours, each sample was diluted to a final concentration of 2% $HNO_3$ and 0.01% HF. The Ta content in the digested samples was analyzed using ICP-OES. Each sample was analyzed in triplicate and each study was repeated thrice. For both NC types, minimal Ta dissolution was observed during the first week. During the second week, dissolution ranged between 0.8-1.2%; for the third week, dissolution within 1.5-1.8% was observed; while for the fourth week, a total of 2.6-2.9% Ta dissolution was recorded (see FIG. 76A-76B).

Section 4. Cellular Studies:

Cellular Viability Using RAW 264.7 and HEK 293 Cells

To test the cytocompatibility of various $TaO_x$ NCs, MTT assay using RAW 264.7 macrophage cells and HEK 293 cells was performed. Briefly, respective cells (100 µL, 100,000 cells per mL) suspended in DMEM supplemented with 10% FBS and 1% antibiotic penicillin-streptomycin were seeded in multiple 96-well plates and incubated for 24 hours (37° C., 5% $CO_2$). Next, 100 µL each of $TaO_x$ NP formulation suspensions in DMEM media were added to the respective wells in a range of concentrations (0.0001-2.4 mg per mL Ta concentration) and the plates were incubated for another 24 hours. After incubation for the desired period, supernatant media from the wells were aspirated out and each well was washed with 100 µL PBS (pH 7.4) thrice, following which 100 µL of fresh DMEM media was added to each well. The final MTT assay was done as described by the manufacturer's protocol.

Section 5. In Vitro Micro-CT Experiments for $TaO_x$ NCs:

For in vitro phantom measurements, solutions of $TaO_x$ NC1 in saline were prepared at various concentrations (0, 20, 50, 80, and 100 mM Ta). Phantom CT images were acquired on a Perkin Elmer Quantum GX micro-CT scanner operating at 90 kVp and 88 µA.

Section 6. In Vivo Micro-CT Experiments for $TaO_x$ NCs:

General Information

Micro-CT was used for quantifying the efficacy of $TaO_x$ NCs when used as a high Z-value radiopaque contrast agent in an in vivo model. BALB/c mice (Charles River Laboratories, Inc.; sex: male, age: approximately 3 months, body weight: approximately 25 g) were randomized into experimental groups and received either a single intravenous dose of formulated $TaO_x$ NCs in sterile saline (0.9% sodium chloride for injection, USP) at 100 mM (n=2) (296 mg kg$^{-1}$) or 200 mM (n=3) $TaO_x$ NCs (592 mg kg$^{-1}$). Animals were serially imaged via micro-CT at 0 hours (baseline), immediate post-injection, and 1, 3, 24, and 72 hours post-injection using the PerkinElmer Quantum GX micro-CT. The following image acquisition scan parameters were used at each scan interval time point: scan mode, high resolution; gantry rotation time, 14 minutes; power, 90 kVp/88 µA; Field of View (FOV), 72 mm; number of slices, 512; slice thickness, 144 µm; voxel resolution, 144 µm$^3$.

Animals were housed in MSU Small Animal Vivarium, with standard 12 hours light cycle (6 am-6 µm) at approximately 30-40 foot candles of light intensity, approximately 72° F. RT, and approximately 45% relative humidity (RH). Animals received water and a standard rodent diet (Envigo Teklad®) ad-libitum and were fasted for approximately 4-6 hours prior to each scan interval to reduce micro-CT image hyperintensity anomalies found in the GI tract.

On Day 0, animals were anesthetized via inhalant isoflurane (3-4% isoflurane in 0.8-1 LPM oxygen for induction) and maintained via inhalant isoflurane during imaging (1-3% isoflurane in 0.8-1 LPM oxygen). A lateral tail vein catheter was placed for I.V. injection, and the $TaO_x$ NC formulation was administered as a single, slow bolus injection (25 µL min$^{-1}$). Animals were fully recovered from anesthesia following each scan interval time point. On Day 3, following the 72 hours post-injection scan time point, animals were euthanized via $CO_2$ inhalation overdose, with cervical dislocation as a secondary physical method to confirm death.

ICP-OES for Ta Content, H&E Staining, and Clinical Chemistry

For ICP analysis, organ sections from the heart, liver, kidneys, and spleen were weighed to record their wet weight and then dried over a heating block. The weight of the dry tissue sections were recorded and next these were digested using a 4:1 mixture of $HNO_3$ (concentrated, 69%) and HF (concentrated, 48%). The resulting solution was stored at RT until complete dissolution was observed. Once a clear and transparent solution with no visible debris was obtained, the solutions were diluted to a final concentration of 2% $HNO_3$ and 0.01% HF to prepare samples that were directly analyzed for Ta content using ICP-OES using a Varian 710-ES, ICP-OES instrument. The Ta content in various organs of mice injected with 100 mM $TaO_x$ NC1 and 200 mM $TaO_x$ NC1 are shown in FIGS. 41A-41B.

After 72 hours scanning and following euthanasia, blood samples were collected for clinical chemistry blood serum analysis, and tissue samples (spleen, liver, heart, kidneys, and bladder) were harvested for histopathology and ICP analysis for Ta content. Various tissue sections from the respective organs of the heart, liver, kidneys, spleen, and bladder were collected and stained with H&E. The representative histological sections for mice injected with 200 mM Ta in saline are shown in FIG. 42 and clearly indicate multifocal areas of necrosis. Such sections within the spleen are characterized by pyknotic cells and karyorrhectic debris surrounded by macrophages. Sections of liver from two of the three mice in the 200 mM Ta dose group had coagulative necrosis with one mouse having a few small randomly distributed foci, while the other mouse had large confluent areas of random midzonal necrosis. These areas were characterized by swollen, hypereosinophilic cells that had lost their nuclear detail, and there was accumulation of karyorrhectic debris. One mouse had multiple acute renal cortical infarcts characterized by sharply demarcated, wedge-shaped areas of coagulative necrosis extending from the beneath the renal capsule into the outer cortex causing slight indentations. These areas were surrounded by tubules lined by swollen epithelial cells and a few infiltrating mononuclear cells. Arterioles at the tip of these infarcts were thrombosed. The histological analysis of the tissues from the bladder, kidney, and heart from mice injected with 200 mM $TaO_x$ NC1 were unremarkable. For mice injected with 100 mM $TaO_x$ NC1, no adverse observation was noted on histological analysis of tissue sections of various organs such as the liver, spleen, kidney, heart, and bladder.

Extensive clinical pathological analysis for all the sets of mice (control and test groups) was performed using a Beckman Coulter AU680U chemistry analyzer and Beckman Coulter reagents. No clinically significant differences were observed in control (saline group) and treated mice (100 mM and 200 mM $TaO_x$ NC1 groups) across a number of parameters, such as albumin, TBIL, DBIL, ALP, ALT, and AST. These findings are summarized in FIGS. 43A-43F. Minor elevation in blood glucose levels were observed in the control and treated groups; however, the differences were not clinically relevant. Further, wide range of values is typical and is affected by factors such as stress associated with collection and length of fasting prior to sample collection. However, the elevated ALT and AST activity in the 200 mM $TaO_x$ NC1 dose group as compared to the control group (saline) and 100 mM $TaO_x$ NC1 dose group supports hepatocellular damage and is consistent with the histologic findings of liver necrosis.

Section 7. Synthetic Details for $TaO_x$@PLGA NPs:

General Information

All reactions, unless otherwise stated, were performed with oven-dry glassware. PLGA (LG 50:50; acid terminated (nominal); inherent viscosity range of 0.95-1.20 dL g$^{-1}$ in HFIP, 20.0 g) was purchased from LACTEL Absorbable Polymers, DURECT Corporation, AL, USA and stored at −20° C. prior to use. All other reagents and solvents were obtained from commercial suppliers and used without further purification. For NP formulation, tip sonication was performed using a QSonica microtip sonicator probe with a tip diameter of 3 mm at varying amplitudes. Centrifugation to isolate NPs from the reaction mixture was performed on a Sorvall LYNX 4000 Superspeed centrifuge.

Synthesis of PLGA NPs Encapsulating $TaO_x$ NCs ($TaO_x$@PLGA NPs)

Prior to encapsulation in PLGA, the hydrophobic $TaO_x$ NC3 were suspended in DCM. The resulting white suspension (25 mg $TaO_x$ NCs per mL DCM) was sonicated for 20 minutes with periodic vortex to form a homogenous suspension of $TaO_x$ NCs in DCM. This suspension was further utilized for NP formulation. A stock solution of 4% PVA in DI water (w/w) was prepared by dissolving 8.0 g PVA (22 kDa, 88% hydrolyzed, SIGMA ALDRICH) in 900 mL DI water by continuous stirring at 50° C. for 2 hours. Once a clear solution was obtained with no visible residue, the volume of the solution was increased to 1000 mL by adding DI water to it. This final solution was allowed to cool down to RT, filtered (using a coarse filter paper), and stored at 4° C. prior to use. A stock solution of PLGA in DCM was prepared (50 mg PLGA polymer per mL DCM) and stored at sub-zero temperatures.

Typical procedure: In a 50 mL falcon tube, 4% PVA (3 mL) was taken. In a separate 15 mL falcon tube, 1.0 mL of the $TaO_x$ NC suspension in DCM was taken and 0.5 mL PLGA stock solution in DCM (25 mg $TaO_x$ NC:25 mg PLGA polymer) was added dropwise to it with continuous vortex. The resulting white colored suspension was sonicated for 5 minutes with periodic vortex to make it homogenous. This solution was next added dropwise to the 4% aqueous PVA solution (3 mL) in the falcon tube with rigorous and continuous vortex. Once addition was complete, the resulting white suspension was tip sonicated at 40% amplitude for 20 seconds and then transferred to an ice bath for 10 seconds. This process of tip sonication, followed by rapid cooling in an ice bath was repeated six times. After the final cycle, the white suspension was added to 10 mL 4% PVA and diluted further using 10 mL ultra-pure water. The resulting reaction mixture was stirred at RT for 3 hours to remove DCM, resulting in particle hardening and consequent NP formulation. After 3 hours, the NPs were isolated by centrifugation at 15,000 rpm for 10 minutes. The white NPs so obtained were cleaned again by repeated dispersion in aqueous media and centrifugation to isolate the NPs, until the supernatant was clear (three times). Dry NPs were isolated by lyophilization of the NP pellet. Product Yield: 34 mg, Ta %=56% (ascertained from ICP-OES).

For FITC-labeled FITC-TaO$_x$@PLGA NPs: The reaction sequence for the fluorescent, FITC-loaded variant of the TaO$_x$@PLGA NPs is shown in FIG. 45B and is similar to the one previously discussed. The only variation lies in using the previously prepared hydrophobic FITC-TaO$_x$ NC5, instead of TaO$_x$ NC3, in the oil phase together with PLGA polymer. The rest of the steps are exactly identical. In order to protect the reaction from light, all the reaction beakers and falcon tubes were covered with aluminum foil. The work up for this reaction was also identical to the non-fluorescent TaO$_x$@PLGA NPs. Dry NPs were isolated by lyophilization of the NP pellet. Product Yield: 34 mg, Ta %=45% (ascertained from ICP-OES).

In all, two different types of TaO$_x$@PLGA NPs were prepared, TaO$_x$ NC3@PLGA and FITC-TaO$_x$ NC5@PLGA (with fluorescent FITC tag). These have been characterized by TEM, SEM, EDS, IR, and ICP. As shown by the TEM images, a homogenous and efficient packing of the hydrophobic TaO$_x$ NCs in PLGA was observed (see the TEM insets of FIGS. 46A-46D, 47A-47C, and 48A-48C) for both NP types. This can be easily explained by the virtue of the procedure used for NP formation that entails the encapsulation of hydrophobic TaO$_x$ NCs within a similarly hydrophobic PLGA shell.

Section 8. Characterization Details for TaO$_x$@PLGA NPs:

General considerations for physicochemical characterization of the NPs are identical to that of the NCs. Please refer to Section 2 for specific details.

Section 9. Synthetic Details for TaO$_x$@MSNPs:

General Information

The synthesis of MSNPs is straightforward and involves a template assisted sol-gel reaction using a silica precursor. This procedure is carried out in an aqueous reaction media and henceforth the moderately hydrophilic TaO$_x$ NC2 were employed. Empty MSNPs were also synthesized.

Synthesis of Empty MSNPs

In a 100 mL four neck round bottom flask fitted with three rubber septa and a screw top temperature probe, CTAB (≥99%, SIGMA, 383 mg) and TEA (anhydrous, SIGMA, 0.060 mL) were taken and water (DI, 50 mL) was added to it. The flask was placed on a heating mantle and the temperature of the reaction mixture was increased to 80° C. On reaching the aforementioned temperature, heating was continued for 1 hour, and a clear solution was obtained. After 1 hour, TEOS (≥99%, ALDRICH, 2.0 mL) was added and heating continued for another 2 hours. Next, the reaction mixture was diluted to three times its volume using MeOH (anhydrous, ACS grade, MACRON, 200 mL), and the MSNPs were collected via centrifugation (15,000 rpm, 10 minutes) as a white colored pellet. This pellet was re-suspended in a solution of HCl (ACS grade, MACRON) in MeOH (10% v/v, 100 mL), and this suspension was heated at reflux for 24 hours. After 24 hours, the reaction mixture was concentrated to a final volume of approximately 2 mL using a rotary evaporator and diluted to approximately 10 mL using DI water. This suspension was next transferred to dialysis membrane bags (SPECTRA/POR® 4 Dialysis Membrane, Standard RC Tubing, MWCO: 12-14 kD), clipped at both ends, and dialyzed against DI water with regular change of external media after 2, 4, 16, 4, 4, and 16 hours. After extensive dialysis, the contents in the dialysis bags were lyophilized to obtain empty MSNPs as a white powder. Product Yield: 430 mg.

Synthesis of MSNPs Embedded with TaO$_x$ NC2 (TaO$_x$@MSNP-OH)

In a 500 mL four neck round bottom flask fitted with three rubber septa and a screw top temperature probe, CTAB (≥99%, SIGMA, 800 mg) and TEA (anhydrous, SIGMA, 0.5 mL) were taken and water (DI, 190 mL) was added to it. To this mixture was added a previously prepared suspension of TaO$_x$ NC2 in water (200 mg in 10 mL). The flask was placed on a heating mantle and temperature of the reaction mixture was increased to 80° C. On reaching the aforementioned temperature, heating was continued for 1 hour to obtain a white colored solution with slight turbidity. After 1 hour, TEOS (≥99%, ALDRICH, 2.0 mL) was added and heating continued for another 2 hours. Next, the reaction mixture was allowed to cool down to ambient temperatures and, following the addition of PEG-Silane (tech-90, MW 591-723, GELEST INC., 2.0 mL), the contents was stirred overnight.

Next, the reaction mixture was diluted to three times its volume using MeOH (anhydrous, ACS grade, MACRON, 200 mL) and the TaO$_x$@MSNPs were collected via centrifugation (15,000 rpm, 10 minutes) as a white colored pellet. This pellet was re-suspended in a solution of HCl (ACS grade, MACRON) in MeOH (10% v/v, 200 mL), and this suspension was heated at reflux for 24 hours. After 24 hours, the reaction mixture was concentrated to a final volume of approximately 2 mL using a rotary evaporator and diluted to approximately 10 mL using DI water. This suspension was next transferred to dialysis membrane bags (SPECTRA/POR® 4 Dialysis Membrane, Standard RC Tubing, MWCO: 12-14 kD), clipped at both ends, and dialyzed against DI water with regular change of external media after 2, 4, 16, 4, 4, and 16 hours. After extensive dialysis, the contents in the dialysis bags were lyophilized to obtain TaO$_x$@MSNP-OH as a white powder. Product Yield: 460 mg, Ta %=43% (ascertained from ICP-OES).

Synthesis of MSNPs Embedded with TaO$_x$ NC2 (TaO$_x$@MSNP-Phosphate)

In a 500 mL four neck round bottom flask fitted with three rubber septa and a screw top temperature probe, CTAB (≥99%, SIGMA, 800 mg) and TEA (anhydrous, SIGMA, 0.5 mL) were taken and water (DI, 190 mL) was added to it. To this mixture was added a previously prepared suspension of TaO$_x$ NC2 in water (200 mg in 10 mL). The flask was placed on a heating mantle and the temperature of the reaction mixture was increased to 80° C. On reaching the aforementioned temperature, heating was continued for 1 hour to obtain a white colored solution with slight turbidity. After 1 hour, TEOS (≥99%, ALDRICH, 2.0 mL) was added and heating continued for another 2 hours Next, Phospha-Silane (tech-95, GELEST INC., 2.0 mL) was added to the reaction mixture and heating continued for another 4 hours.

Next, the reaction mixture was allowed to cool down to RT, diluted to three times its volume using MeOH (anhydrous, ACS grade, MACRON, 200 mL), and the TaO$_x$@MSNPs were collected via centrifugation (15,000 rpm, 10 minutes) as a white colored pellet. This pellet was re-suspended in a solution of HCl (ACS grade, MACRON) in MeOH (10% v/v, 200 mL), and this suspension was heated at reflux for 24 hours. After 24 hours, the reaction mixture was concentrated to a final volume of approximately 2 mL using a rotary evaporator and diluted to approximately 10 mL using DI water. This suspension was next transferred to dialysis membrane bags (SPECTRA/POR® 4 Dialysis Membrane, Standard RC Tubing, MWCO: 12-14 kD), clipped at both ends, and dialyzed against DI water with regular change of external media after 2, 4, 16, 4, 4, and 16 hours. After extensive dialysis, the contents in the dialysis bags were lyophilized to obtain TaO$_x$@MSNP-Phos as a white powder. Product Yield: 450 mg, Ta %=45% (ascertained from ICP-OES).

Synthesis of MSNPs Embedded with FITC-TaO$_x$ NC4 (FITC-TaO$_x$@MSNP)

In a 500 mL four neck round bottom flask fitted with three rubber septa and a screw top temperature probe, CTAB (≥99%, SIGMA, 500 mg) and TEA (anhydrous, SIGMA, 0.6 mL) were taken and water (DI, 190 mL) was added to it. To this mixture was added a previously prepared suspension of hydrophilic FITC-TaO$_x$ NC4 in water (250 mg in 10 mL). The flask, covered with an aluminum foil, was placed on a heating mantle and the temperature of the reaction mixture was increased to 80° C. On reaching the aforementioned temperature, heating was continued for 1 hour to obtain a yellow colored solution with slight turbidity. After 1 hour, TEOS (≥99%, ALDRICH, 1.5 mL) was added and heating continued for another 2 hours. Next, Phospha-Silane (tech-95, GELEST INC., 1.5 mL), was added to the reaction mixture and heating continued for another 2 hours.

Next, the reaction mixture was allowed to cool down to RT and following the addition of PEG-Silane (tech-90, MW 591-723, GELEST INC., 2.0 mL), the contents were stirred overnight. All these procedures were carried out in the dark to protect from light. Next, the reaction mixture was diluted to three times its volume using MeOH (anhydrous, ACS grade, MACRON, 200 mL) and the FITC-TaO$_x$@MSNPs were collected via centrifugation (15,000 rpm, 10 minutes) as a white colored pellet. This pellet was re-suspended in DI water and transferred to dialysis membrane bags (SPECTRA/POR® 4 Dialysis Membrane, Standard RC Tubing, MWCO: 12-14 kD), clipped at both ends, and dialyzed in two stages. For the first stage, dialysis was carried out against a 1:1:0.01 mixture of water:ethanol:glacial acetic acid with regular change of media after 24 hours. This cycle was repeated thrice and ensured the removal of the surfactant CTAB. Next, the dialysis bags were transferred for extensive dialysis against DI water with regular change of external media after 2, 4, 16, 4, 4, and 16 hours. After extensive dialysis, the contents in the dialysis bags were lyophilized to obtain FTIC-TaO$_x$@MSNP-Phos as a yellow colored free flowing powder. Product Yield: 430 mg, Ta %=39% (ascertained from ICP-OES).

Section 10. Characterization of TaO$_x$@MSNPs:

General considerations for physicochemical characterization of the MSNPs are identical to that of the NCs. Please see Section 2 for specific details.

Section 11. Estimation of Ta Content and Ta Dissolution from TaO$_x$ NPs:

Ta Content Estimation Using ICP-OES

To estimate the Ta content in various TaO$_x$ NPs, a strategy identical to the one for NCs was adopted. All measurements were carried out in triplicates, and the mean concentrations have been reported. For specific details, refer to "Ta Content Estimation using ICP-OES" in Section 3.

In Vitro Ta Dissolution

To analyze the dissolution of various TaO$_x$ NPs in lysosomal media, an in vitro dissolution study was carried out. A similar strategy as with the NCs was adopted. For specific details, refer to "In Vitro Ta Dissolution" in Section 3. For both NP types, minimal Ta dissolution was observed during the first week. During the second week, dissolution ranged between 0.5-1%; for the third week, dissolution within 1.0-1.5% was observed; while for the fourth week, a total of 2.5-3.0% Ta dissolution was recorded (see FIGS. 73A-73B).

Section 12. Cellular Studies:

Cellular Viability Using RAW 264.7 and HEK 293 Cells

To test the cytocompatibility of various TaO$_x$ NP formulations, MTT assay using RAW 264.7 macrophage cells and HEK 293 cells was performed. For specific details, refer to "Cellular Viability using RAW 264.7 and HEK 293 Cells" in Section 4.

Section 13. In Vivo Micro-CT Experiments with TaO$_x$ NPs: General Information

Micro-CT was used for quantifying the efficacy of TaO$_x$ NPs when used as a high Z-value radiopaque contrast agent in an in vivo model. In Vivo TaO$_x$ NP X-Ray attenuation evaluation using micro-CT image acquisition and analysis was performed on BALB/c Mice (Charles River Laboratories, Inc.; sex: male, age: approximately 3 months, body weight: approximately 25 g) (n=3) by injecting a localized bolus of TaO$_x$ NPs using the same micro-CT scan parameters previously detailed for in vivo biodistribution of TaO$_x$ NCs at a single scan time point: immediate post-injection.

While under isoflurane inhalant anesthesia, a 50 µL bolus of 50 mM TaO$_x$@PLGA NPs and a 50 µL bolus of 50 mM TaO$_x$@MSNP-OH were administered bilaterally (IM) between the superficial gluteal muscle and biceps femoris muscle (n=1), a 50 µL bolus of 50 mM and a 50 µL bolus of 25 mM TaO$_x$@MSNP-OH were administered bilaterally (IM) between the gastrocnemius muscle and caudal tibial muscle (n=1), and a 50 µL bolus of 50 mM and a 50 µL bolus of 25 mM TaO$_x$@PLGA NPs were administered bilaterally (IM) between the gastrocnemius muscle and caudal tibial muscle (n=1). Following micro-CT image acquisition, animals were euthanized and carcasses discarded. No blood or tissues were collected. Micro-CT image rendering, segmentation, and analysis were performed using Caliper AnalyzeDirect® (v12.0, Biomedical Imaging Resource, Mayo Clinic, Rochester, Minn., USA).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A nanoparticle composition comprising:
   a plurality of nanoparticles, each nanoparticle of the plurality having:
   a core comprising tantalum oxide, and
   a covalent coating covalently bound to the core, the covalent coating comprising a surface modifier comprising 2-[methoxy (polyethyleneoxy)-9-12-propyl] trimethoxysilane (PEG-Silane) and hexadecyltriethoxy silane.

2. The nanoparticle composition according to claim 1, wherein the nanoparticle composition is in the form of a lyophilized powder.

3. The nanoparticle composition according to claim 1, wherein the tantalum oxide comprises TaO$_x$, where 0<x≤2.5, Ta$_2$O$_5$, or combinations thereof.

4. The nanoparticle composition according to claim 3, wherein the tantalum oxide comprises TaO, TaO$_2$, Ta$_2$O$_5$, or combinations thereof.

5. The nanoparticle composition according to claim 1, wherein the plurality of nanoparticles is a first plurality of nanoparticles, the core is a first core, the covalent coating is a first covalent coating, and the surface modifier is a first surface modifier, and the nanoparticle composition further comprises:
- a second core comprising tantalum oxide; and
- a second covalent coating covalently bound to the second core, the second covalent coating comprising a second surface modifier comprising PEG-Silane, (3-aminopropyl)trimethoxy silane (APTMS), and APTMS-methoxy-poly(ethylene-glycol)-succinimidyl glutarate (APTMS-m-PEG-glutarate),
- the second plurality of nanoparticles being hydrophilic.

6. The nanoparticle composition according to claim 1, wherein the plurality of nanoparticles is a first plurality of nanoparticles, the core is a first core, the covalent coating is a first covalent coating, and the surface modifier is a first surface modifier, and the nanoparticle composition further comprises:
- a second core comprising tantalum oxide; and
- a second covalent coating covalently bound to the second core, the second covalent coating comprising a second surface modifier comprising PEG-Silane and (3-aminopropyl)trimethoxy silane (APTMS),
- the second plurality of nanoparticles being hydrophobic.

7. The nanoparticle composition according to claim 1, wherein the plurality of nanoparticles is a first plurality of nanoparticles, the core is a first core, the covalent coating is a first covalent coating, and the surface modifier is a first surface modifier, and the nanoparticle composition further comprises:
- a second core comprising tantalum oxide; and
- a second covalent coating covalently bound to the second core, the second covalent coating comprising a second surface modifier comprising PEG-Silane and fluorescein isothiocyanate (3-aminopropyl)trimethoxy silane (FITC-APTMS),
- the second plurality of nanoparticles being hydrophilic.

8. The nanoparticle composition according to claim 1, wherein the plurality of nanoparticles is a first plurality of nanoparticles, the core is a first core, the covalent coating is a first covalent coating, and the surface modifier is a first surface modifier, and the nanoparticle composition further comprises:
- a second core comprising tantalum oxide; and
- a second covalent coating covalently bound to the second core, the second covalent coating comprising a second surface modifier comprising PEG-Silane, (3-aminopropyl)trimethoxy silane (APTMS), and fluorescein isothiocyanate (FITC)-APTMS,
- the second plurality of nanoparticles being hydrophobic.

9. The nanoparticle composition according to claim 1, further comprising:
- a non-covalent coating non-covalently associated with the hexadecyltriethoxy silane, the non-covalent coating comprising a hydrophobic polymer.

10. The nanoparticle composition according to claim 9, wherein the plurality of nanoparticles are non-covalently embedded within the hydrophobic polymer.

11. The nanoparticle composition according to claim 1, wherein each nanoparticle of the plurality of nanoparticles further comprises a mesoporous silica nanoparticle (MSNP), wherein the at least one core having the covalent coating is embedded within the MSNP.

12. The nanoparticle composition according to claim 1, further comprising:
- a pharmaceutically acceptable carrier,
- wherein the nanoparticle composition is configured to provide contrast for computed tomography (CT).

13. The nanoparticle composition according to claim 1, wherein the plurality of nanoparticles are embedded within a polymer having a predetermined shape, wherein the nanoparticle composition is configured as a biological scaffold.

14. The nanoparticle composition according to claim 1, further comprising:
- a polymer,
- wherein the plurality of nanoparticles are either dissolved in the polymer or suspended in the polymer, and
- wherein the nanoparticle composition is configured to solidify into a three-dimensional shape during a three-dimensional printing process.

15. The nanoparticle composition according to claim 1, further comprising:
- a therapeutic agent coupled to the covalent coating.

16. A method of fabricating a biological scaffold, the method comprising three-dimensional printing the biological scaffold with a bio-ink comprising the nanoparticle composition according to claim 1.

17. A method of fabricating a biological scaffold, the method comprising disposing a polymer about a mask having a predetermined shape and solidifying the polymer, wherein the polymer comprises the nanoparticle composition according to claim 1.

18. A nanoparticle composition comprising:
- a plurality of nanoparticles, each nanoparticle of the plurality comprising:
  - a core comprising tantalum oxide; and
  - a covalent coating covalently bonded to the core, the covalent coating comprising a surface modifier comprising 2-[methoxy (polyethyleneoxy)-9-12-propyl] trimethoxysilane (PEG-Silane) and hexadecyltriethoxy silane; and
- a polymer, wherein the plurality of nanoparticles are non-covalently embedded within the polymer.

19. The nanoparticle composition according to claim 18, wherein the polymer comprises poly(lactic-co-glycolic acid) (PLGA).

20. A method of synthesizing a nanoparticle composition, the method comprising:
- combining an organic solvent with an aqueous solution to form a water-in-oil micro-emulsion;
- adding a compound comprising tantalum to the micro-emulsion to form uncoated tantalum nanoparticles; and
- covalently binding a surface modifier to the uncoated tantalum nanoparticles to form the nanoparticle composition, the surface modifier comprising 2-[methoxy (polyethyleneoxy)-9-12-propyl]trimethoxysilane (PEG-Silane) and hexadecyltriethoxy silane,
- wherein the nanoparticle composition comprises:
  - a plurality of nanoparticles, each nanoparticle of the plurality having:
    - a core comprising tantalum oxide, and
    - a covalent coating, the covalent coating comprising the surface modifier covalently bound to the core.

21. The method according to claim 20, further comprising:
- embedding the plurality of nanoparticles within a polymer.

22. The method according to claim 20, further comprising:
- dialyzing the plurality of nanoparticles in water; and
- lyophilizing the plurality of nanoparticles to generate a lyophilized powder comprising the plurality of nanoparticles.

23. The nanoparticle composition according to claim 1, wherein the plurality of nanoparticles is a first plurality of nanoparticles, the core is a first core, the covalent coating is a first covalent coating, and the surface modifier is a first surface modifier, and the nanoparticle composition further comprises:

a second core comprising tantalum oxide; and
a second covalent coating covalently bound to the second core, the second covalent coating comprising a second surface modifier selected from the group consisting of (3-aminopropyl)trimethoxy silane (APTMS), (3-aminopropyl)triethoxy silane (APTES), APTMS-methoxy-poly(ethylene-glycol)-succinimidyl glutarate (APTMS-m-PEG-glutarate), APTES-methoxy-poly (ethylene-glycol)-succinimidyl glutarate (APTES-m-PEG-glutarate), 2-[methoxy (polyethyleneoxy)-9-12-propyl] trimethoxysilane (PEG-Silane), fluorescein isothiocyanate (FITC)-APTMS, FITC-APTES, hexadecyltriethoxy silane, and combinations thereof.

24. The nanoparticle composition according to claim 1, wherein the plurality of nanoparticles is a first plurality of nanoparticles, the core is a first core, the covalent coating is a first covalent coating, and the surface modifier is a first surface modifier, and the nanoparticle composition further comprises:

a second core comprising tantalum oxide; and
a second covalent coating covalently bound to the second core, the second covalent coating comprising a second surface modifier selected from the group consisting of (3-aminopropyl)triethoxy silane (APTES), APTES-methoxy-poly(ethylene-glycol)-succinimidyl glutarate (APTES-m-PEG-glutarate), fluorescein isothiocyanate (FITC)-APTES, and combinations thereof.

* * * * *